United States Patent
Zavaleta Fernandez de Cordova

(10) Patent No.: US 11,168,249 B1
(45) Date of Patent: *Nov. 9, 2021

(54) LUMINESCENT POLYDENTATE POLYCYCLIC COMPOUNDS FOR METAL IONS

(71) Applicant: Andres Zavaleta Fernandez de Cordova, Lodi, NJ (US)

(72) Inventor: Andres Zavaleta Fernandez de Cordova, Lodi, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/860,294

(22) Filed: Apr. 28, 2020

Related U.S. Application Data

(63) Continuation-in-part of application No. 15/820,146, filed on Nov. 21, 2017, now Pat. No. 10,633,586, which is a continuation-in-part of application No. 14/012,701, filed on Aug. 28, 2013, now Pat. No. 9,823,199.

(60) Provisional application No. 61/694,581, filed on Aug. 29, 2012.

(51) Int. Cl.
| | |
|---|---|
| G01N 21/78 | (2006.01) |
| G01N 31/22 | (2006.01) |
| C09K 11/06 | (2006.01) |
| C07D 471/04 | (2006.01) |
| G01N 33/18 | (2006.01) |

(52) U.S. Cl.
CPC ............ *C09K 11/06* (2013.01); *C07D 471/04* (2013.01); *G01N 21/78* (2013.01); *G01N 31/22* (2013.01); *C09K 2211/181* (2013.01); *C09K 2211/182* (2013.01); *C09K 2211/187* (2013.01); *C09K 2211/188* (2013.01); *G01N 33/1813* (2013.01)

(58) Field of Classification Search
CPC .... G01N 21/78; G01N 31/22; G01N 33/1813; C09K 2211/18; C09K 2211/181–188
See application file for complete search history.

(56) References Cited

U.S. PATENT DOCUMENTS

| | | | | |
|---|---|---|---|---|
| 5,266,700 | A | * | 11/1993 | Langhals ............... B41M 3/144 546/140 |
| 5,393,614 | A | | 2/1995 | Nakada |
| 5,648,270 | A | * | 7/1997 | Kuhn ...................... C09K 11/06 436/172 |
| 9,823,199 | B1 | | 11/2017 | Zavaleta Fernandez de Cordova |
| 10,633,586 | B1 | * | 4/2020 | Zavaleta Fernandez de Cordova ............. C07D 401/14 |
| 2011/0237776 | A1 | * | 9/2011 | Haley ................ C07D 491/056 530/323 |

FOREIGN PATENT DOCUMENTS

JP 2004091444 A 3/2004

OTHER PUBLICATIONS

Nakano, S. "Studies on 2,2-Biquinoline Derivatives. V. Copper(l) Chelate of 2,2'-Biquinoline Derivatives." Yakugaku Zasshi vol. 81 (1961), No. 9, pp. 1239-1244. (Year: 1961).*
Magdesieva, T.V. et al. "Polymeric 2,2'-biquinolyl-containing Nill complexes as catalysts for the Suzuki reaction," Russian Chemical Bulletin, International Edition, vol. 61, No. 6, p. 1193-1198, Jun. 2012 (Year: 2012).*
Kim, Y.-H. "A new anion receptor with biquinoline molecular scaffold," J Incl Phenom Macrocycl Chem (2013) 76:119-124. Online Jun. 10, 2012 (Year: 2012).*
Song et al., "Fluorogenic $Hg^{2+}$—Selective Chemodosimeter Derived from 8-Hydroxyquinoline," Org. Lett., vol. 8, No. 16, pp. 3413-3416.
Thummel et al., "Polyaza Cavity-Shaped Molecules. Annelated Derivatives of 2-(2'-Pyridyl)-1,8-naphthyridine and 2,2'-Bi-1,8-naphthyridine," J. Org. Chem. 1984, 49, pp. 2208-2212.
Williams et al., "Strong Metal Ion Size Based Selectivity of the Highly Preorganized Ligand PDA (1, 10-Phenanthroline-2,9-dicarboxylic Acid) with Trivalent Metal Ions. A Crystallographic, Fluorometric, and Thermodynamic Study," Inorg. Chem. 2009, 49, pp. 7853-7863.
Dean et al., "Affinity of the Highly Preorganized Ligand PDA (1,10-Phenanthroline-2,9-dicarboxylic acid) for Large Metal Ions of Higher Charge. A Crystallographic and Thermodynamic Study of PDA Complexes of Thorium(IV) and the Uranyl(VI) ion," Inorg. Chem. 2008, 47, pp. 2000-2010.
Gao et al., "Synthesis and Structure of a La(III) Complex of 1,10-Phenanthroline-2,9-dicarboxylate: a Three-dimensional Network via Hydrogen Bonding Interactions," Chinese J. Struct. Chem. 2008, vol. 27, No. 2, pp. 137-142.
Melton et al., "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid. A Thermodynamic and Crystallographic Study," Inorg. Chem. 2006, 45, pp. 9306-9314.
Sheshmani et al., Ion Pairing, H-bonding, and π-πInteractions in Cobalt(II) Compound Containing Guanidinium Counter Ion, Z. Anorg. Allg. Chem. 2006, 632, pp. 469-474.
Xie et al., "The synthesis and structure of the $Ni^{II}$ complex of 1,10-phenanthroline-2,9-dicarboxylate: a three-dimensional network via hydrogen bonding interactions," J. Mol. Struct. 2005, 741, pp. 249-243.

(Continued)

*Primary Examiner* — Christopher Adam Hixson
*Assistant Examiner* — Michelle Adams
(74) *Attorney, Agent, or Firm* — Fay Sharpe LLP; George Huang

(57) ABSTRACT

Polydentate polycyclic compounds of various formulas are disclosed herein. The compounds are useful for ratiometric luminescence. Significantly, the compounds will luminesce at different wavelengths/colors, depending on the analyte (metal ion, acid, or boron-containing compound) it is combined with. Thus, a single compound can provide different luminescent outputs based on the analyte, rather than requiring an entire set of structurally different compounds to detect each analyte or to generate a desired color output.

18 Claims, 18 Drawing Sheets

(14 of 18 Drawing Sheet(s) Filed in Color)

(56) References Cited

OTHER PUBLICATIONS

Moghimi et al., "First Anionic 1,10-Phenanthroline-2,9-dicarboxylate Containing Metal Complex Obtained from a Novel 1:1 Proton-Transfer Compound: Synthesis, Characterization, Crystal Structure, and Solution Studies," Inorg. Chem. 2003, 42, pp. 1616-1624.

Coates et al., "Enhancement of luminescence of europium(III) ions in water by use of synergistic chelation. Part 2. 1:1:1 Complexes," J. Chem. Soc. Perkin. Trans. 2, 1996, pp. 1283-1287.

Gudgin Templeton et al., "Spectroscopic Characterization of 1,10-Phenanthroline-2,9-Dicarboxylic Acid and Its Complexes With Europium (III): Luminescent europium chelates useful for analytical applications in aqueous solution," Journal of Luminescence 1989, 43, pp. 195-205.

Chandler et al., "Synthesis of some 2,9-Disubstituted-1,10-phenanthrolines," J. Heterocyclic Chem. 1981, 18, pp. 599-601.

Thummel et al., Incorporation of Quinoline-5,8-quinone Moiety into Polyaza Cavities, J. Org. Chem. 1993, 58, pp. 1666-1671.

Liu et al., "Synthesis of 5,8,5', 8'-Dimethoxy-3,3'-dimethylene-2,2'-biquinoline," Chinese Journal of Sythetic Chemistry, 2006, vol. 14, No. 1, pp. 97-98.

Demura et al., "Copper(II) Complex of 2,2'-Bi-8-quinolinol," Bull. Chem. Soc. Jpn., 1982, 55, pp. 2863-2865.

Palacios et al., "Hydroxyquinolines with extended fluorophores: arrays for turn-on and ratiometric sensing of cations," Chem. Commun. 2007, pp. 3708-3710.

Wang et al., "Fluorescence Sensor Array for Metal Ion Detection Based on Various Coordination Chemistries: General Performance and Potential Application," Analytical Chemistry, 2008, vol. 80, No. 19, pp. 7451-7459.

Palacios et al., "Rational Design of a Minimal Size Sensor Array for Metal Ion Detection," J. Am. Chem. Soc. 2008, 130, pp. 10307-10314.

Gonzalez-Vera et al., "Synthesis of Red-Shifted 8-Hydroxyquinoline Derivatives Using Click Chemistry and Their Incorporation into Phosphorylation Chemosensors," J. Org. Chem. 2009, 74, pp. 7309-7314.

Rosillo et al., "Tandem Enyne Metathesis—Diels-Alder Reaction of Construction of Natural Product Frameworks," J. Org. Chem. 2004, 69, pp. 2084-2093.

Andres Zavaleta and Thomas Wayne Bell, "31, Ligands for the Self Assembly of 10-Coordinate Europium Complexes," Department of Chemistry, University of Nevada, Reno, Nevada, Abstract for doctoral dissertation. 2002.

Andres Zavaleta, "I. Complexation of Metals with Pentadentate Ligands. II. Hydrogen-bonding receptors for creatinine". Aug. 2002. Thesis (Ph.D.), University of Nevada, Reno, 2002.

Zhang, Q. et al. "Novel Heteroleptic CuI Complexes with Turnable Emission Color for Efficient Phosphorescent Light-Emitting Diodes," Adv. Funct. Mater. 2007, 17, 2983-2990.

Thomas, P. "Zweizahlig koordiniertes Nitrat in Bis(cuproin)-Komplexen des Nickel(II), Kobalt(II) und Kupfer(II), "Zeitschrift fuer Chernie (1972), vol. 12, Issue: 0, Pagers 338-339.

SciFinder abstract of Thomas, P. "Metal chelates of cuproine-and-ferroin-type ligands, IV. Bidentate nitrate in bis(cuproine) complexes of nickel(II), cobalt(II), and copper(II), "Zeitschrift fuer Chernie (1972), vol. 12, Issue: 9, pp. 338-339.

* cited by examiner

Solid State Properties of D1

LUMINESCENT POLYDENTATE POLYCYCLIC COMPOUNDS FOR METAL IONS

CROSS-REFERENCE TO RELATED APPLICATIONS

This application is a continuation-in-part of U.S. patent application Ser. No. 15/820,146, filed Nov. 21, 2017, now U.S. Pat. No. 10,633,586, which is a continuation-in-part of U.S. patent application Ser. No. 14/012,701, filed Aug. 28, 2013, now U.S. Pat. No. 9,823,199, which claims priority to U.S. Provisional Patent Application Ser. No. 61/694,581, filed on Aug. 29, 2012. That application is hereby incorporated by reference in its entirety.

BACKGROUND

The present disclosure relates to various polydentate polycyclic compounds whose luminescent properties change when combined with an analyte. These compounds may be useful in light-emitting applications, metal ion detection or recognition, metal ion extraction, catalysis, development of shape-persistent macrocycles, and/or assembly of metal organic frameworks.

Luminescence is the emission of light by a substance/material that does not result from heat. Examples of luminescence include fluorescence and phosphorescence. Fluorescence occurs when a substance/material absorbs ultraviolet (UV) light, and then emits light, typically of a lower wavelength. This phenomenon can be useful in many applications. For example, in biochemistry, an antibody can be labeled with a fluorophore. The antibody will attach to its target antigen, and the fluorescence of the fluorophore can be detected to identify the location of the target antigen. Labelling multiple antibodies with different fluorophores allows visualization of multiple target antigens. For example, one fluorophore can emit a red color, a second fluorophore can emit a blue color, and a third fluorophore can emit a green color. In fluorescence, the re-emission of light occurs relatively quickly (nanoseconds), whereas in phosphorescence the re-emission of light occurs relatively slowly (milliseconds to hours).

Generally, a structurally different compound is needed for each different color. As a result, an entire set of structurally different compounds are needed in order to obtain different luminescent outputs. It would be desirable to be able to reduce the number of compounds needed to generate the same number of different luminescent outputs.

BRIEF DESCRIPTION

The present disclosure relates to various compounds or receptors that can generate different luminescent colors upon exposure to different analytes. Generally speaking, the compounds of the present disclosure incorporate the structural properties of 8-hydroxyquinoline to form a polydentate polycyclic compound. The compounds interact with analytes such as metal ions, acids, or boron-containing compounds, and luminesce at different wavelengths depending upon the analyte. This can be useful in applications such as metal ion extraction, metal ion detection, organic light emitting diodes, magnetic resonance imaging (MRI) contrast agents, catalysts, and the generation of storage devices such as metal-organic frameworks.

Disclosed in various embodiments herein is a compound having the structure of Formula (S1), or a polymer formed from a monomer having the structure of Formula (S1):

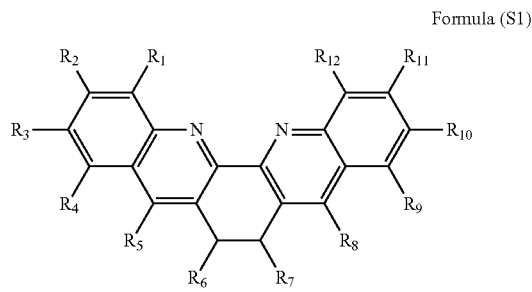

Formula (S1)

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_6$ is —OR', —SR', —COR', or —NR'$_2$;

at least one of $R_7$ to $R_{12}$ is —OR", —SR", —COR", or —NR"$_2$; and wherein R' and R" are either (a) independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound;

with the proviso that no four of $R_1$, $R_2$, $R_3$, $R_4$, $R_5$, $R_6$, $R_7$, $R_8$, $R_9$, $R_{10}$, $R_{11}$, and $R_{12}$ are alkoxy.

In some particular embodiments of (S1), R' and R" are each a chelating ligand, and each chelating ligand is selected from —CO—R, —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, —(CH$_2$)$_n$—[O—(CH$_2$)$_k$]$_m$—OR, or salts thereof; wherein k, m, and n are independently integers from 0 to 10; R, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic; and Z is sulfur or oxygen. R' and R" can be the same.

In particular embodiments, $R_4$ and $R_9$ are the same, and are not hydrogen. In others, $R_4$ and $R_9$ are halogen, aryl, substituted aryl, alkynyl, or substituted alkynyl.

The compound of Formula (S1) may have the structure of one of formulas (D1)-(D9), as described further herein. The compound of Formula (S1) may be a macrocyclic compound having the structure of Formula (S1-M) or Formulas (M1)-(M7) as described further herein.

Also disclosed are methods for making a compound of Formula (S1), comprising: reacting a 1,2-cyclohexanedione of Formula (S1a) with a first aminoaldehyde; and optionally, when R' and R" are different, reacting the resulting compound with a second different aminoaldehyde.

The reacting may occur in the presence of potassium hydroxide and ethanol until the aminoaldehyde is consumed, wherein trifluoroacetic acid is subsequently added to precipitate the compound of Formula (S1).

In particular embodiments, the method may further comprise: reducing the resulting compound with hydrobromic acid to form a dihydroxy-3,3'-dimethylene-2,2'-biquinoline; reacting the dihydroxy-3,3'-dimethylene-2,2'-biquinoline with a first reactant of the formula $L^a$-R', wherein $L^a$ is a leaving group; and wherein R' and R" are different, reacting the resulting compound with a second reactant of the formula $L^b$-R", wherein $L^b$ is a leaving group.

The reacting of the dihydroxy-3,3'-dimethylene-2,2'-biquinoline with the first and second reactants can occur in the presence of a polar solvent.

Also disclosed herein are methods for binding a metal ion in a solution, comprising: adding to the solution a compound having the structure of Formula (S1), or a polymer formed from a monomer having the structure of Formula (S1), wherein the compound or polymer forms a complex upon binding to the metal ion.

Sometimes, the methods further comprise monitoring the solution to detect a change in the color of light emitted by the compound or polymer, such a change indicating that binding has occurred. The methods can also further comprise extracting the metal ion from the solution.

Also disclosed herein are compounds or monomers having the structure of Formula (S2):

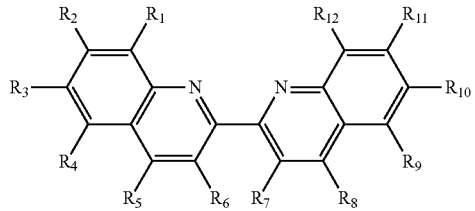

Formula (S2)

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; wherein at least one of $R_1$ to $R_6$ is —OR', —SR', —COR', or —NR'$_2$; at least one of $R_7$ to $R_{12}$ is —OR", —SR", —COR", or —NR"$_2$; and wherein R' and R" either (a) are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound.

Also disclosed herein are compounds or monomers having the structure of Formula (S3):

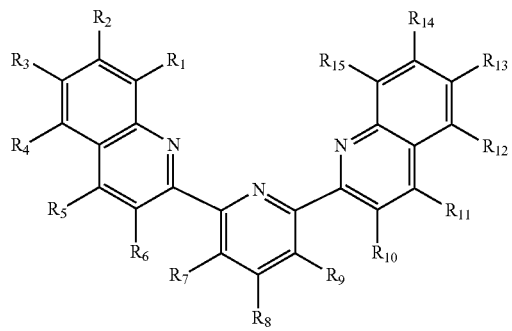

Formula (S3)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; wherein at least one of $R_1$ to $R_8$ is —OR', —SR', —COR', or —NR'"2; at least one of $R_9$ to $R_{15}$ is —OR", —SR", —COR", or —NR""2; wherein R' and R" either (a) are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound; and wherein R'" and R"" either (a) are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound.

Also disclosed herein are compounds or monomers having the structure of Formula (S4):

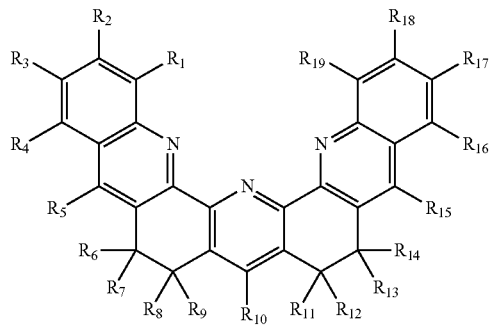

Formula (S4)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_5$ and $R_{10}$ is —OR', —SR', —COR', or —NR'"2; at least one of $R_{15}$ to $R_{19}$ is —OR", —SR", —COR", or —NR""2; wherein R' and R" either (a) are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound; and wherein R'" and R"" either (a) are independently hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound.

Sometimes, in Formula (S2), (S3), or (S4), R' and R" are each a chelating ligand, and each chelating ligand is selected from —CO—R, —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, —(CH$_2$)$_n$—[O—(CH$_2$)$_k$]$_m$—OR, or salts thereof; wherein k, m, and n are independently integers from 0 to 10 and k+m+n≥1; R, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic; and Z is sulfur or oxygen.

Sometimes, the compound of Formula (S3) has the structure of one of formulas L1, L2, or L3, as described further herein. Sometimes, the compound of Formula (S4) has the structure of formula L4 as described further herein.

Also disclosed herein are compounds having the structure of Formula (S5), or a polymer formed from a monomer having the structure of Formula (S5):

Formula (S5)

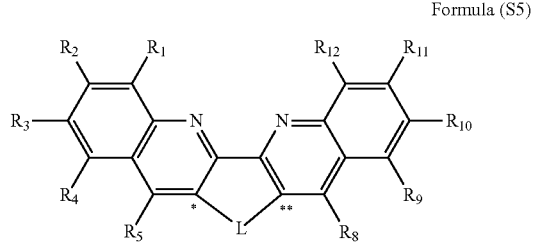

wherein $R_1$, $R_2$, $R_3$, $R_4$, $R_5$, $R_8$, $R_9$, $R_{10}$, $R_{11}$, and $R_{12}$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_5$ is —OR', —SR', —COR', or —NR'$_2$; at least one of $R_8$ to $R_{12}$ is —OR", —SR", —COR", or —NR"$_2$; and wherein R' and R" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound; and wherein L is a bridge having a backbone length of 1, 2, 3, or 4; and the backbone comprises methylene, amino, sulfur, or oxygen;

with the proviso that no four of $R_1$, $R_2$, $R_3$, $R_4$, $R_5$, $R_8$, $R_9$, $R_{10}$, $R_{11}$, and $R_{12}$ and any methylene groups in the bridge L are alkoxy.

Also disclosed herein are compounds having the structure of Formula (S6), or a polymer formed from a monomer having the structure of Formula (S6):

Formula (S6)

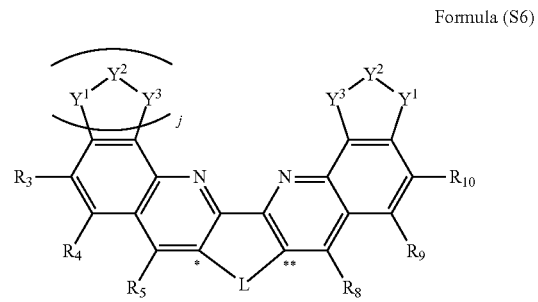

wherein $R_3$, $R_4$, $R_5$, $R_8$, $R_9$, and $R_{10}$ are independently selected from hydrogen, alkoxy, substituted alkoxy, aryloxy, substituted aryloxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

j is either 0 or 1;

$Y^1$, $Y^2$, and $Y^3$ are independently —O—, —NR'—, —BR$^2$—, —S—, —(CO)—, —(PO)—, —(PO$_2$)—, or alkylene or substituted alkylene having 1 to 3 carbon atoms, or combinations thereof, wherein R$^1$ is hydrogen, alkyl, substituted alkyl, aryl, or substituted aryl, and wherein R$^2$ is hydrogen, hydroxyl, alkyl, substituted alkyl, or halogen; and wherein L is a bridge having a backbone length of 1, 2, 3, or 4; and the backbone comprises methylene, amino, sulfur, or oxygen.

Also disclosed herein are compounds having the structure of Formula (S7), or a polymer formed from a monomer having the structure of Formula (S7):

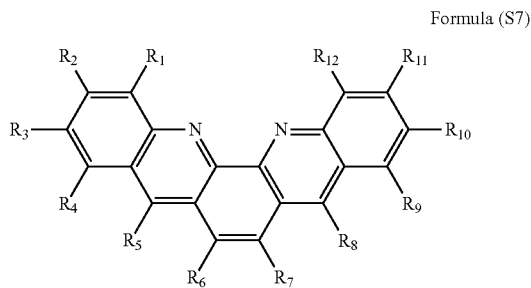

Formula (S7)

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;
wherein at least one of $R_1$ to $R_5$ is —OR', —SR', —COR', or —NR'$_2$;
wherein at least one of $R_8$ to $R_{12}$ is —OR'', —SR'', —COR'', or —NR''$_2$; and
wherein R' and R'' either (a) are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or (b) together form a linking moiety that contains at least one heteroatom, so that the compound is a macrocyclic compound.

These and other non-limiting characteristics are more particularly described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
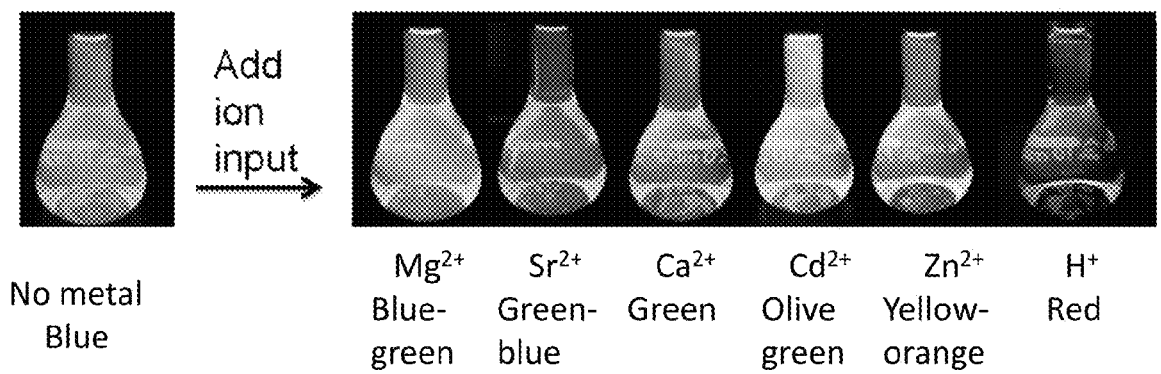
FIG. 1 is a set of pictures showing the change in color of derivative compound D1 in the absence and presence of various metal ions ($Mg^{2+}$, $Sr^{2+}$, $Ca^{2+}$, $Cd^{2+}$, $Zn^{2+}$, $H^+$) in solution. The solvent was acetonitrile, the concentration of D1 was 0.004 M, and the metal ion concentration was 0.04 M. The metal ions are added as perchlorates or acetates. The solutions were exposed to UV light having an excitation wavelength of 365 nm.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of."

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

Disclosed herein are highly preorganized C-shaped multidentate receptors for metal ions. These receptors incorporate the structural properties of 8-hydroxyquinoline, and generally possess exposed hydroxyl (—OH) groups that can be used for further functionalization, resulting in hexa-, hepta-, octa-, or even higher denticity. These receptors/compounds are generally formed from different scaffolds disclosed herein. When suitably substituted, the scaffolds for these compounds can be made into macrocycles, preorganized lariat-ether like receptors, chiral catalysts, building blocks to make molecular springs (when connected in series), metal-organic frameworks, and/or water soluble ligands that can be used with suitable metal ions. The additional chelating arms that can be attached to these hydroxyl groups may incorporate a variety of nitrogen-, oxygen-, or sulfur-containing groups, or other known fluorophores to facilitate discrimination in metal ion binding abilities and therefore metal ion selectivity. The scaffolds can also be substituted at the aromatic rings to fine-tune the optical properties of these molecules and/or for the generation of cyclic structures.

The compounds disclosed herein are highly preorganized (S1, S4) or partially pre-organized (S2, S3). The phrase highly preorganized is used to indicate that the compounds have no relevant entropic energy cost associated with metal ion binding. The compounds of the present disclosure generally adopt only one conformation. In contrast, other compounds can adopt numerous conformations and require expenditure of energy to adopt the conformation that is suitable for binding a given metal ion. The full preorganization of the present compounds leads to a cavity of fixed size, which can help discriminate between metal ions of different ionic radius, and thus provide better selectivity. Less preorganized receptors adopt multiple conformations and are therefore less selective. Generally, the fixed cavity size of the compounds of the present disclosure is suitable for metal ions with ionic radius of about 1.0 angstroms (ca. 1.0 Å).

The compounds of the present disclosure typically are at least tetradentate, and can be heptadentate, and can have even higher denticity. Higher denticity results in a more efficient binding of metal ions, as there are more "claws" to grab the ion of interest. They also possess exposed hydroxyl groups, which can be used for the attachment of a variety of ligands that can lead to increased denticity using substitution by simple Sn2 or acylation reactions. In contrast, the denticity of existing compounds is capped.

Other substitutions can lead to the synthesis of molecular coils (due to the non-planar structure of the scaffolds), macrocycles, or lariat ether-like receptors. The additional chelating ligands that can be introduced may include a variety of nitrogen-, oxygen-, or sulfur-containing groups, which permit tuning of the binding properties of the overall compound by regulating the affinity of metal ions for these additional chelating ligands.

The present disclosure thus relates to seven different scaffold compounds denoted (S1), (S2), (S3), (S4), (S5), (S6), and (S7) herein, and to several subgenera and species thereof which are generated by appropriate substitution at various locations on the scaffold compounds. The scaffold compounds can be used as molecular compounds, or can be used as monomers in linear, branched, or cyclic polymers.

For purposes of the present disclosure, the term "polymer" refers to any molecule in which two or more monomers based on a scaffold compound can be identified. It is recognized that the term "oligomer" is used to refer to molecules that contain a few monomers; however, because there is no generally recognized threshold in the number of monomers that distinguishes between an oligomer and a polymer, the term "polymer" is used herein to encompass both concepts.

Any of these scaffold compounds can form complexes with a metal ion, such as Gd(III), Fe(III), Co(III), Ni(II), Mn(II), Cu(II), Mg(II), Sr(II), Ca(II), Cd(II), Zn(II), Ba(II), $K^+$, $H^+$, Al(III), Pb(II), La(III), Co(II), Hg(II), or another paramagnetic metal ion.

Scaffold S1

The first scaffold compound (S1) can be considered as a combination of five rings: two phenyl rings at the ends to which the oxygen atoms are attached, two pyridine rings, and one cyclohexane ring. The first scaffold compound is based off of dihydroxy-3,3'-dimethylene-2,2'-biquinoline, and has the following formula:

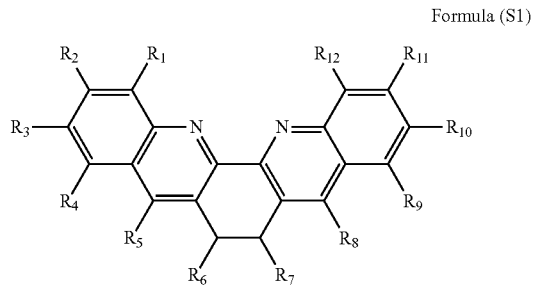

Formula (S1)

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_6$ is —OR', —SR', —COR', or —NR'$_2$; at least one of $R_7$ to $R_{12}$ is —OR", —SR", —COR", or —NR"$_2$; and wherein R' and R" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, ester, phosphate, a boron-containing group, or a chelating ligand comprising at least one linking group and at least one heteroatom, or together form a linking moiety that contains at least one heteroatom, so that the compound is a macrocyclic compound;

with the proviso that no four of $R_1$, $R_2$, $R_3$, $R_4$, $R_5$, $R_6$, $R_7$, $R_8$, $R_9$, $R_{10}$, $R_{11}$, and $R_{12}$ are alkoxy. Put another way, (S1) will not have four alkoxy substituents. For purposes of clarity, it is noted that the center ring is a cyclohexane ring, i.e. the carbon atoms to which $R^6$ and $R^7$ are bound each also have a hydrogen atom which is not illustrated.

Exemplary water-solubilizing groups include, but are not limited to, sugars, polyethers, carboxylates, and oxides (such as phenoxide). Methoxy and ethoxy groups are not considered to be water-solubilizing groups.

The term "alkyl" refers to a radical composed entirely of carbon atoms and hydrogen atoms which is fully saturated. The alkyl radical may be linear, branched, or cyclic. The alkyl radical has the ability to form a single bond to one or two different non-hydrogen atoms, depending on the context. For example, the formulas —$CH_2$—$CH_3$ and —$CH_2$—$CH_2$— should both be considered alkyl. As used herein, an alkyl group has from 1 to about 18 carbon atoms.

The term "aryl" refers to an aromatic radical composed entirely of carbon atoms, and optionally hydrogen atoms along the perimeter of the radical. The aromatic radical can take any shape. For example, the aromatic radical can be a planar radical such as phenyl or napthyl, or can be three-dimensional such as fullerene (e.g. CH) or a carbon nanotube. It is noted that these three-dimensional radicals do not have any hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms). The aryl radical has the ability to form a single bond to one or two different non-hydrogen atoms, depending on the context. For example, the radicals —$C_6H_5$ and —$C_6H_4$— could both be referred to as phenyl and should both be considered aryl radicals. As used herein, an aryl group has from 6 to about 120 carbon atoms, and in narrower embodiments has from 6 to about 10 carbon atoms.

The term "heteroaryl" refers to a cyclic radical composed of carbon atoms, hydrogen atoms, and a heteroatom within a ring of the radical, the cyclic radical being aromatic. The heteroatom may be nitrogen, sulfur, or oxygen. Exemplary heteroaryl groups include thienyl, pyridinyl, furanyl, pyrryl, indolyl, and quinolinyl. When heteroaryl is described in connection with a numerical range of carbon atoms, it should not be construed as including substituted heteroaromatic radicals. The heteroaryl radical has the ability to form a single bond to one or two different non-hydrogen atoms, depending on the context. For example, the radicals —$C_4H_3S$ and —$C_4H_2S$— could both be referred to as thienyl, and should both be considered heteroaryl radicals. As used herein, a heteroaryl group has from 5 to about 18 carbon atoms.

The term "pyridinyl" refers to a radical formed by removing one or two hydrogen atoms from the heterocyclic compound pyridine.

The term "furanyl" refers to a radical formed by removing one or two hydrogen atoms from the heterocyclic compound furan.

The term "pyrryl" refers to a radical formed by removing one or two hydrogen atoms from the heterocyclic compound pyrrole.

The term "thienyl" refers to a radical formed by removing one or two hydrogen atoms from the heterocyclic compound thiophene The term "indolyl" refers to a radical formed by removing one or two hydrogen atoms from a heterocyclic compound formed by the fusing of benzene with pyrrole (e.g. indole or isoindole).

The term "quinolinyl" refers to a radical of the formula by removing one or two hydrogen atoms from an acene having at least one carbon atom replaced with a nitrogen atom (e.g. quinoline, isoquinoline, quinoxaline, acridine, etc).

The term "heteroatom" refers to only oxygen, nitrogen, sulfur, and boron.

The term "heterocyclic" refers to a cyclic radical composed of carbon atoms, hydrogen atoms, and at least one heteroatom within the ring of the radical. The cyclic radical may be aromatic or non-aromatic. A heterocyclic group has from 5 to about 18 carbon atoms.

The term "phosphate" refers to a radical of the formula —O—(PO$_3$) or the formula —PO$_3$, depending on the context. In particular, a peroxide linkage (—O—O—) is not contemplated to occur when a phosphate group is referred to.

The term "boron-containing group" refers to a radical that contains a boron atom. Examples of such groups include —B(OH)$_2$ or —BF$_3$ or —BR$^1$R$^2$, where R$^1$ and R$^2$ are independently hydroxyl, alkoxy, alkyl, substituted alkyl, aryl, substituted aryl, alkenyl, or substituted alkenyl.

The term "chelating ligand" refers to a radical that is able to bind to a metal atom to form a coordination complex. A chelating ligand is formed from a combination of at least one linking group and at least one heteroatom. The chelating ligand may or may not possess one or more chiral centers. The chelating ligand is a linear radical, or in other words is linked to the scaffold compound via a bond at one end of the radical. The linking group can be made from any suitable combination of atoms, such as alkyl, substituted alkyl, aryl, substituted aryl, heteroaryl, substituted heteroaryl, heterocyclic, substituted heterocyclic, alkenyl, substituted alkenyl, alkynyl, substituted alkynyl, and amino. Exemplary chelating ligands are further described herein.

The term "macrocyclic compound" refers to a cyclic compound that contains multiple potential donor atoms that can coordinate to a metal center. At least one heteroatom in the linking moiety must be a potential donor atom. The linking moiety can be made from any suitable combination of atoms, such as alkyl or aryl or multiple heteroatoms.

The term "halogen" refers to fluorine, chlorine, bromine, and iodine.

The term "alkenyl" refers to a radical composed entirely of carbon atoms and hydrogen atoms which contains at least one carbon-carbon double bond that is not part of an aryl or heteroaryl structure. The alkenyl radical may be linear, branched, or cyclic. The alkenyl radical may be bonded to one or two different non-hydrogen atoms, depending on the context.

The term "alkynyl" refers to a radical composed entirely of carbon atoms and hydrogen atoms which contains at least one carbon-carbon triple bond. The alkynyl radical may be bonded to one or two different non-hydrogen atoms, depending on the context.

The term "hydroxyl" refers to the —OH radical.

The term "aldehyde" refers to a radical of the formula —CO—R, where R is hydrogen, alkyl, substituted alkyl, aryl, or substituted aryl, and also refers to the salt thereof (when R is absent and the oxygen atom has a valence of −1).

Examples of aldehyde groups include formyl (—CO—H) and acyl. The term "alkylcarbonyl" is a subset of aldehyde radicals.

The term "carboxy" refers to a radical of the formula —COOR, where R is hydrogen, alkyl, substituted alkyl, aryl, or substituted aryl, and also refers to the salt thereof. The carboxy radical bonds through the carbon atom. The term "alkoxycarbonyl" is a subset of carboxy radicals.

The term "alkoxy" refers to an alkyl radical which is attached to an oxygen atom, i.e. —O—C$_n$H$_{2n+1}$.

The term "ester" refers to a radical of the formula —O—CO—R, where R is hydrogen, alkyl, substituted alkyl, aryl, or substituted aryl, and also refers to the salt thereof. The ester radical bonds through an oxygen atom.

The term "sulfonate" refers to a radical of the formula —SO$_2$—OR, where R is hydrogen, alkyl, substituted alkyl, aryl, or substituted aryl, and also refers to the salt thereof.

The term "sulfonamide" refers to a radical of the formula —SO$_2$—NR$^1$R$^2$, where R$^1$ and R$^2$ are independently hydrogen, alkyl, substituted alkyl, aryl, or substituted aryl.

The term "carboxamide" refers to a radical of the formula —CO$_2$—NR$^1$R$^2$, where R$^1$ and R$^2$ are independently hydrogen, alkyl, substituted alkyl, aryl, or substituted aryl.

The term "amide" refers to a radical of the formula —CO—NR'R$^2$ or —NR$^1$—CO—R$^2$, where R$^1$ and R$^2$ are independently hydrogen, alkyl, substituted alkyl, aryl, or substituted aryl.

The term "amino" refers to a radical of the formula —NR$^1$R$^2$, where R$^1$ and R$^2$ are independently hydrogen, alkyl, substituted alkyl, aryl, or substituted aryl. This includes monosubstituted radicals (i.e. where R$^2$ is hydrogen) and disubstituted radicals (where neither R$^1$ nor R$^2$ are hydrogen).

The term "nitro" refers to a radical of the formula —NO$_2$.

The term "nitroso" refers to a radical of the formula —N=O.

The term "nitrile" refers to a radical of the formula —C≡N.

The term "carbonyl" refers to a radical of the formula —CO—.

The term "azo" refers to a radical containing an —(R$^1$)$_m$—N=N—(R$^2$)$_n$, where m and n are independently 0 or 1, R$^1$ is alkyl or substituted alkyl, and R$^2$ is hydrogen, alkyl, substituted alkyl, aryl, or substituted aryl.

The term "thiol" refers to a radical of the formula —SH.

The term "sulfide" refers to a radical of the formula —SR', where R$^1$ is alkyl, substituted alkyl, aryl, or substituted aryl, alkenyl, or substituted alkenyl.

The term "sugar" refers to a radical of the formula —C$_n$H$_{2n-1}$O$_n$, wherein n is between 3 and 30, and contains a number of hydroxyl groups and at least one carbonyl group. This term should be considered to include any number of saccharides covalently bonded together.

The term "polyether" refers to a radical of the formula —(CH$_2$)$_n$—[O—(CH$_2$)$_k$]$_m$—OR, wherein R is hydrogen, alkyl, substituted alkyl, aryl, or substituted aryl; wherein n is an integer from k, m, and n are independently integers from 1 to 10; and also refers to the salt thereof.

The term "substituted" refers to at least one hydrogen atom on the named radical being substituted with another functional group. An exemplary substituted alkyl group is a perhaloalkyl group, wherein one or more hydrogen atoms in an alkyl group are replaced with halogen atoms. An alkyl, alkenyl, or alkynyl group can be substituted with an aryl, substituted aryl, heteroaryl, substituted heteroaryl, heterocyclic, substituted heterocyclic, alkoxy, hydroxyl, cyano, amino, nitro, nitroso, nitrile, halogen, or azo group. An aryl or heteroaryl group can be substituted with an alkyl, substituted alkyl, alkoxy, hydroxyl, cyano, amino, nitro, nitroso, nitrile, and/or halogen group. As another example, the radical —COC(OCH$_3$)(C$_6$H$_5$)CF$_3$ could be considered a substituted alkylcarbonyl, where an ethyl radical has been substituted with three fluorine atoms on the beta carbon and with a methoxy group and a phenyl group on the alpha carbon. Please note that the functional group can itself be substituted.

The compound of Formula (S1) can be asymmetrical or symmetrical. In particular embodiments of Formula (S1), the compound is symmetrical. In specific embodiments of Formula (S1), at least one of R$_1$ to R$_6$ is —OR', and at least one of R$_7$ to R$_{12}$ is —OR". In further specific embodiments of Formula (S1), only one of R$_1$ to R$_6$ is —OR', and only one of R$_7$ to R$_{12}$ is —OR". The —OR' and —OR" groups are usually located symmetrically. In particular embodiments, the —OR' and —OR" groups are located at R$_1$ and R$_{12}$.

In more specific embodiments of Formula (S1), R' and R" are chelating ligands, and the heteroatom of the chelating ligand is present as a carbonyl group. In other embodiments, the chelating ligand is —CO—R, —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, —(CH$_2$)$_n$—[O—(CH$_2$)$_k$]$_m$—OR, or salts thereof; wherein k, m, and n are independently integers from 0 to 10 and k+m+n≥1 (i.e. greater than or equal to 1); R, R$^1$, R$^2$, and R$^3$ are independently hydrogen, alkyl, substituted alkyl, aryl, substituted aryl, heteroaryl, substituted heteroaryl, heterocyclic, or substituted heterocyclic; and Z is sulfur or oxygen. Specific examples of such chelating ligands include —CH$_2$—CO—OCH$_3$, and —CH$_2$—CO—O$^-$. It is believed that chelating ligands incorporating sulfur atoms may lead to selectivity towards Hg(II) ions. It should be noted that R' and R" are usually the same.

In some narrower embodiments of Formula (S1), R$_4$ and R$_9$ are the same, and are not hydrogen. In additional embodiments, R$_4$ and R$_9$ are not hydrogen or alkoxy. For example, in particular embodiments, R$_4$ and R$_9$ are halogen, aryl, substituted aryl, alkynyl, or substituted alkynyl. In particular embodiments, R$_2$, R$_3$, R$_5$, R$_6$, R$_7$, R$_8$, R$_{10}$, and R$_{11}$ are hydrogen, while R$_4$ and R$_9$ are the same and are not hydrogen.

In additional specific embodiments of Formula (S1), the —OR', —SR', —COR', —NR'$_2$, —OR", —SR", —COR", or —NR"$_2$ groups are located at R$_1$ and R$_{12}$. In these embodiments, R$_4$ and R$_9$ are the same, and are not hydrogen or a water-solubilizing group. Put another way, R$_4$ and R$_9$ are independently selected from halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, and sulfide.

Specific derivatives of the scaffold compound (S1) include those of formulas (D1)-(D9):

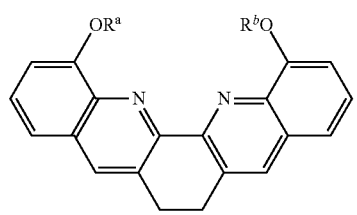
(D1)

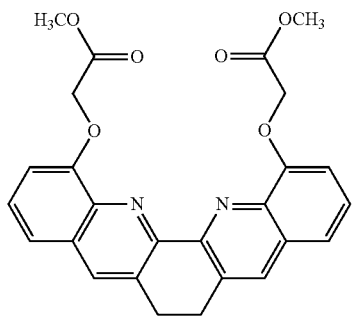
(D2)

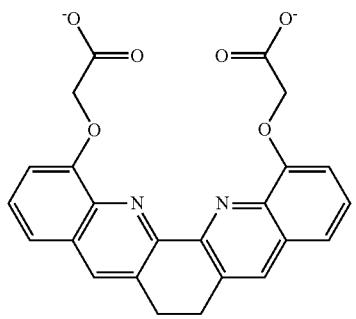
(D3)

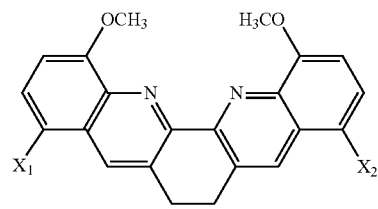
(D4)

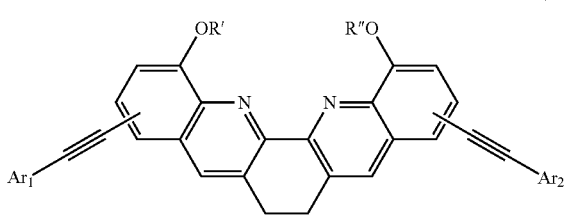
(D5)

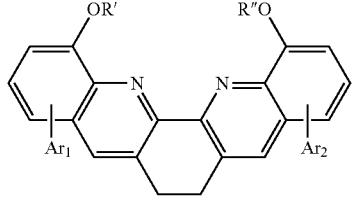
(D6)

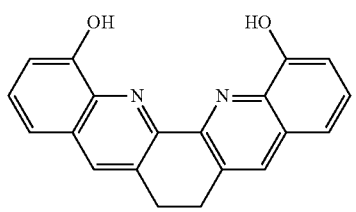
(D7)

(D8)
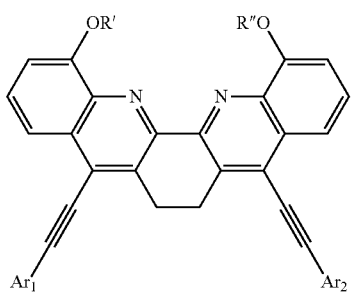

(D9)
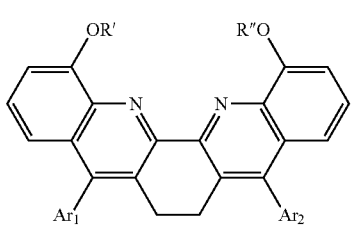

wherein $R^a$ and $R^b$ are independently alkyl, substituted alkyl, aryl, substituted aryl, heteroaryl, substituted heteroaryl, heterocyclic, or substituted heterocyclic; R' and R" are independently alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom; $X_1$ and $X_2$ are independently halogen; and $Ar_1$ and $Ar_2$ are independently aryl or substituted aryl. In some more specific embodiments of (D1), $R^a$ and $R^b$ are alkyl, and in particular embodiments are —$CH_3$. In more specific embodiments of (D5) and (D6), the linkages are connected at the $R_4$ and $R_9$ positions, i.e. para to the phenolic oxygen atoms.

Additional specific derivatives of the scaffold compound (S1) include those of formulas (D10)-(D21):

(D10)
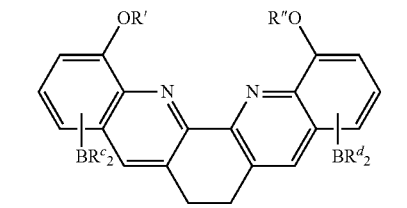

(D11)
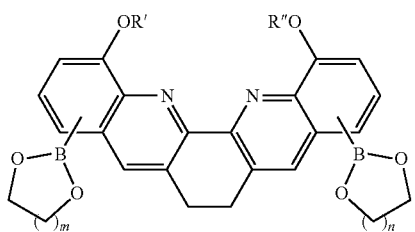

(D12)
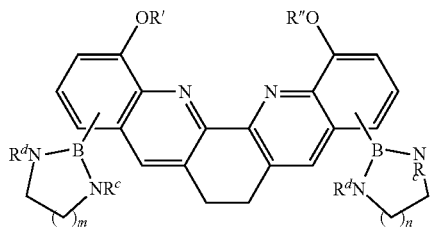

(D13)
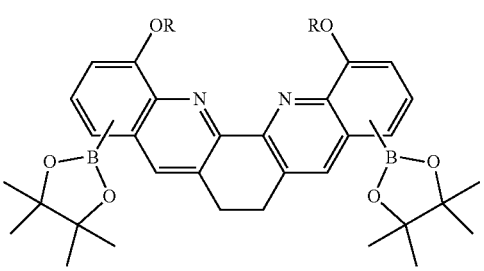

(D14)
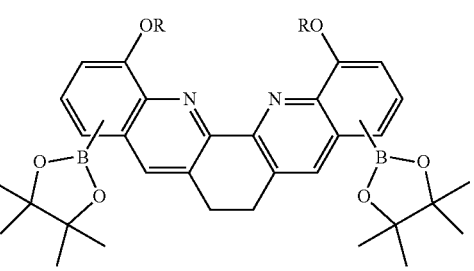

(D15)
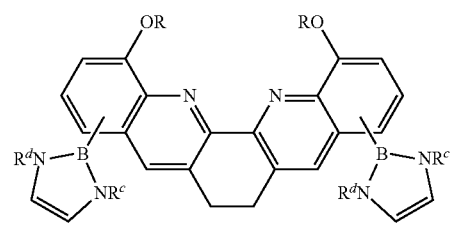

(D16)
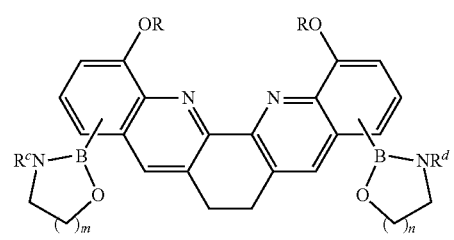

(D17)
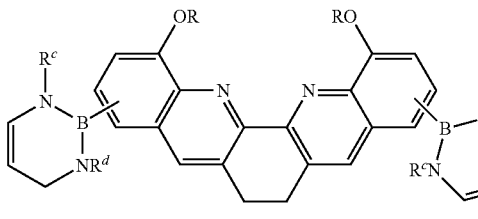

(D18)
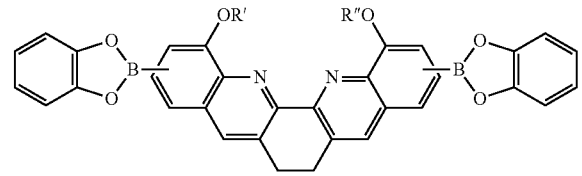

-continued

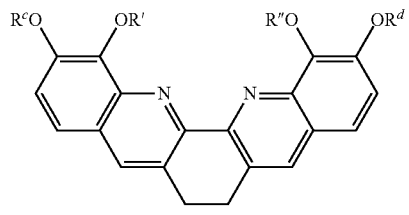
(D19)

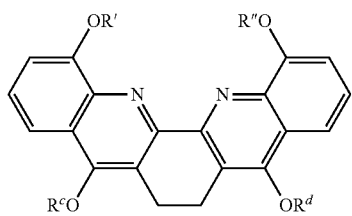
(D20)

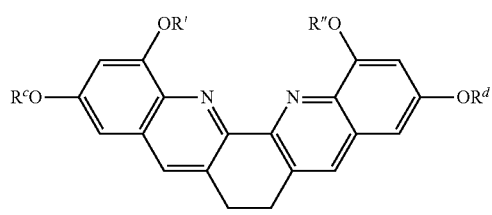
(D21)

wherein $R^c$ and $R^d$ are independently hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, or a boron-containing group; R' and R" are independently alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom; and m and n are independently integers from 1 to 3. It should be noted for clarity that the two side groups depicted in (D10) through (D18) can be located on $R_2$, $R_3$, $R_4$, $R_5$, $R_6$, $R_7$, $R_8$, $R_9$, $R_{10}$, or $R_{11}$ (one on $R_2$-$R_6$, and one on $R_7$-$R_{11}$).

In more specific embodiments of (D10)-(D21), R' and R" are independently alkyl or a chelating ligand comprising at least one linking group and at least one heteroatom.

As previously noted, macrocyclic compounds of Formula (S1) are also contemplated. In these compounds, a linking moiety connects the two oxygen atoms of the —OR' and the —OR" groups together. Macrocyclic compounds of Formula (S1) may have the general structure of Formula (S1-M):

Formula (S1-M)

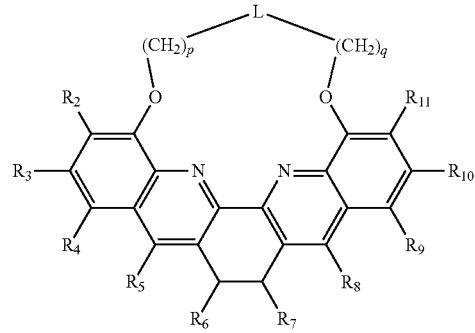

wherein $R_2$-$R_{11}$ are as defined above, p and q are independently integers from 1 to 10;

and L is a linking group. The linking group can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino.

Specific examples of exemplary macrocyclic compounds are illustrated in Formulas (M1)-(M7):

(M1)

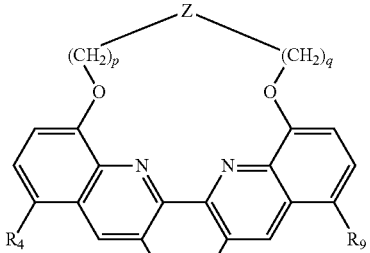

(M2)

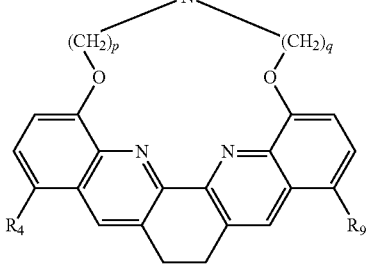

(M3)

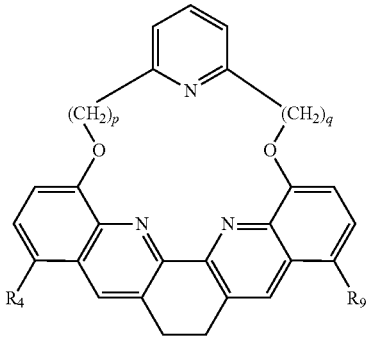

(M4)

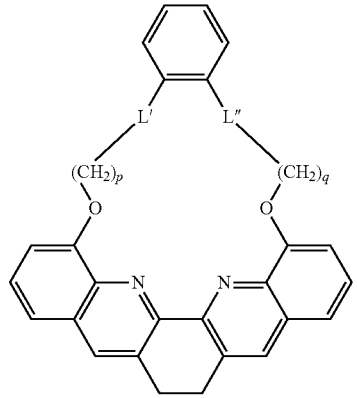

(M5)
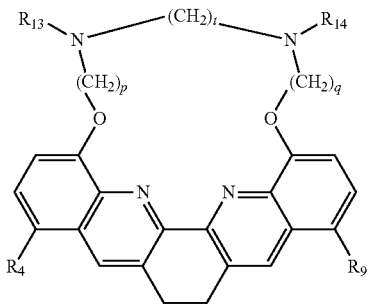

(M7)
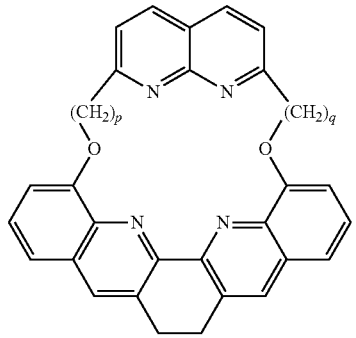

(M6)
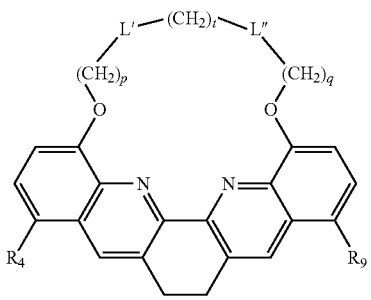

wherein p, q, and t are independently integers from 1 to 10; Z is oxygen or sulfur; L' and L" are independently O, S, or NR'; R', $R_{13}$, and $R_{14}$ are independently hydrogen, alkyl, substituted alkyl, aryl, or substituted aryl; and wherein $R_4$ and $R_9$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, and a water-solubilizing group.

Polymers using the compounds of Formula (S1) as a monomer are also contemplated. The monomers are linked through the oxygen atoms of the compound (S1), or through the carbon atoms on the phenyl rings. The polymers can be linear, cyclic, or branched. For example, the compound (D1) is used as the monomer in the polymers of Formulas (P1)-(P6) depicted below. For simplicity, the —OR' and —OR" groups are illustrated as being located at $R_1$ and $R_{12}$, though they can generally be located as described above.

Formula (P1)
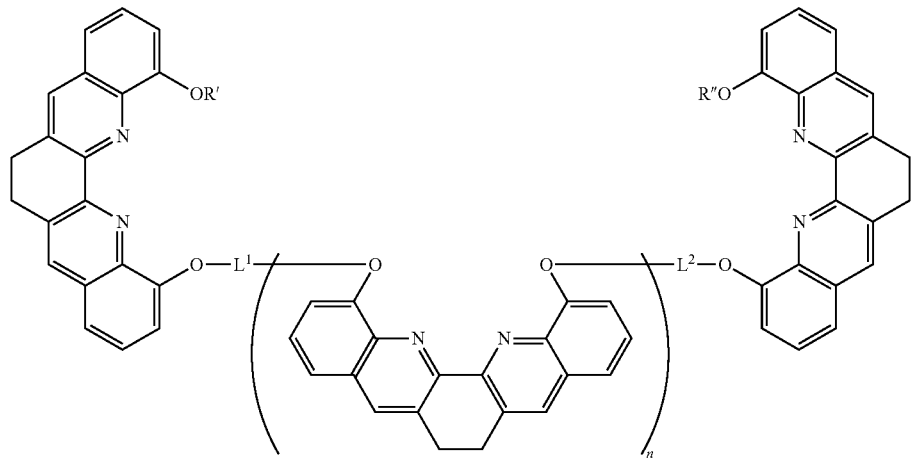

-continued
Formula (P2)
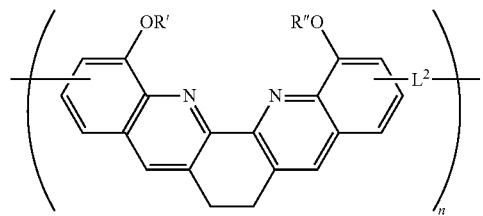
Formula (P3)
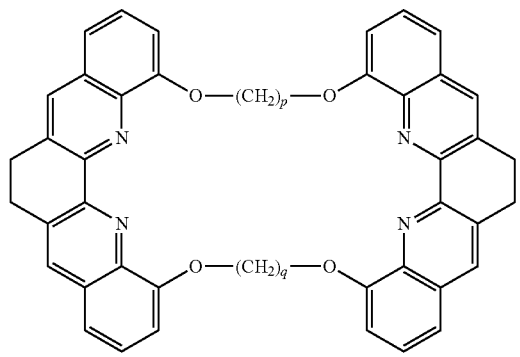
Formula (P4)
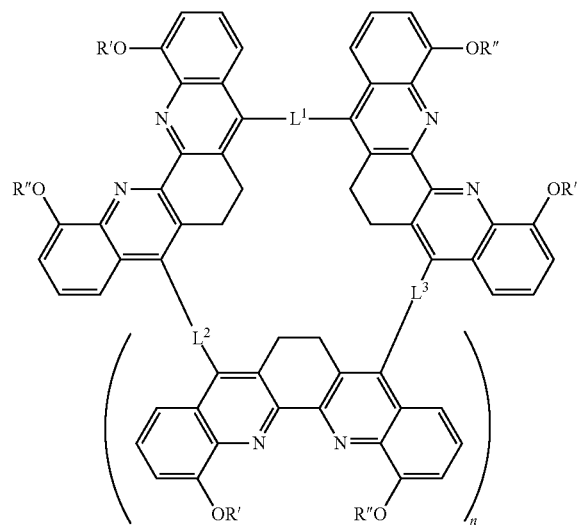
Formula (P5)
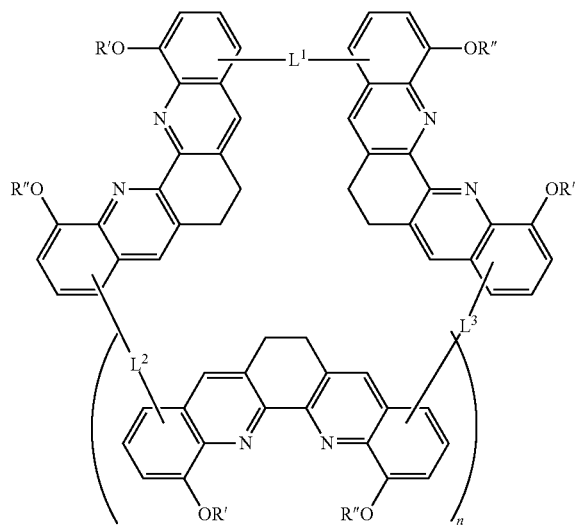

Formula (P6)

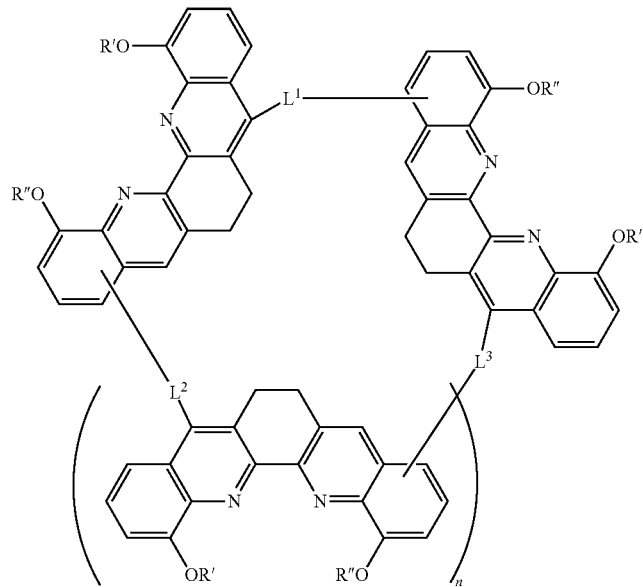

wherein $L^1$, $L^2$, and $L^3$ are independently linking groups; R' and R" are independently alkyl, substituted alkyl, aryl, substituted aryl, heteroaryl, substituted heteroaryl, heterocyclic, substituted heterocyclic, or a chelating ligand comprising at least one linking group and at least one heteroatom; and n is the degree of polymerization, and is from 0 to about 100. In (P2), w is the degree of polymerization, and is from 2 to about 100. Again, the linking groups can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino. For example, the linking groups could be alkyl. It is noted that the polymers can be homopolymers or copolymers (i.e. two or more different monomers). It is noted that (P3) is a cyclic polymer where n=2, and that (P4)-(P6) are cyclic polymers.

For clarity, it is noted that in (P4)-(P6), $L^2$ is within the repeating unit, while $L^3$ is outside the repeating unit. It should be noted that in (P5), the linkages $L^1$, $L^2$, and $L^3$ can be through any of the carbon atoms on the phenyl ring, (i.e. ortho-, meta-, or para-) depending on the identity of the linkage. It should be noted that in (P4)-(P6), depending on the location of the linkages and the number of repeating units, the various portions of the cyclic polymer can rotate so that the R' and R" groups are directed to the interior or the exterior of the cyclic polymer, whichever is more stable.

Derivatives D2 and D3 can be used as an MRI contrast agent when bound to suitable metal ions such as Gd(III), Fe(III), Co(III), Ni(II), Mn(II), or Cu(II). Other paramagnetic metal ions may also be suitable. Derivative D3 can permit the chelation of two water molecules to Gd(III), which is twice as many as in current commercial products. This is expected to lead to either increased resolution or to a reduced dose of the contrast agent. The number of water molecules can be larger.

The derivative D1 exhibits an intrinsic blue fluorescence in the solid state and in solution (i.e. acetonitrile). This fluorescence can be red-shifted to any portion of the visible spectrum by selection of an appropriate metal ion or acid. Derivative D1 can therefore serve as a ratiometric multicolor fluorescence generator and operate as a "universal" sensor that permits identification of the presence of a given metal ion based on the color of the fluorescence. D1 can also serve as an on/off switch because its intrinsic blue fluorescence can also be quenched if certain metal ions are present. That D1 binds the metal ion or acid has been confirmed by solution studies (fluorescence, $^1$H NMR spectroscopy) and X-ray crystallography.

These properties of D1 are shown in FIGS. 1-7. FIG. 1 shows D1 in solution by itself, and with various metal ions added and the resulting color listed below. With no metal, the D1 solution was blue. With $Mg^{2+}$, the solution was a blue-green color. With $Sr^{2+}$, the solution was a green-blue color. With $Ca^{2+}$, the solution was a green color. With $Cd^{2+}$, the solution was an olive green color. With $Zn^{2+}$, the solution was a yellow-orange color. With $H^+$, the solution was a red color.

Figure 2:
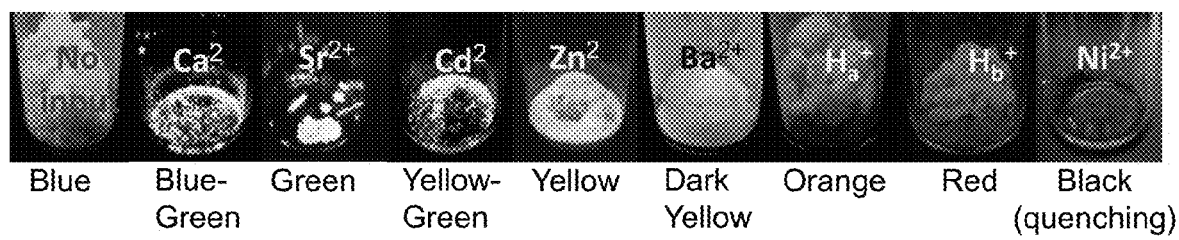
FIG. 2 is a set of pictures showing the change in color of derivative compound D1 in the absence and presence of various metal ions ($Ca^{2+}$, $Sr^{2+}$, $Cd^{2+}$, $Zn^{2+}$, $Ba^{2+}$, $Ha^+$, $H_b^+$, $Ni^{2+}$) in the solid state. The sample labeled $H_a^+$ was isolated from a KOH/ethanol solution after treatment with trifluoroacetic acid (TFA). The sample labeled $H_b^+$ was obtained by using aluminum perchlorate, which produced acid ($H^+$) due to an unexpected hydrolysis reaction with the medium.

FIG. 2 shows D1 in the solid state (i.e. powder), and with various metal ions added and the resulting color listed below. With no metal, the D1 powder was blue. With $Ca^{2+}$, the powder was a blue-green color. With $Sr^{2+}$, the powder was a green color. With $Cd^{2+}$, the powder was a yellow-green color. With $Zn^{2+}$, the powder was a yellow color. With $Ba^{2+}$, the powder was a dark yellow color. Powder isolated from an ethanolic solution of KOH treated with TFA had an orange color. Powder isolated from solutions containing $AlCl_3$ or $Al(ClO_4)_3$ was a red color. X-ray crystallography showed a protonated ligand. With $Ni^{2+}$, the powder was black (i.e. fluorescence was quenched).

Figure 3:
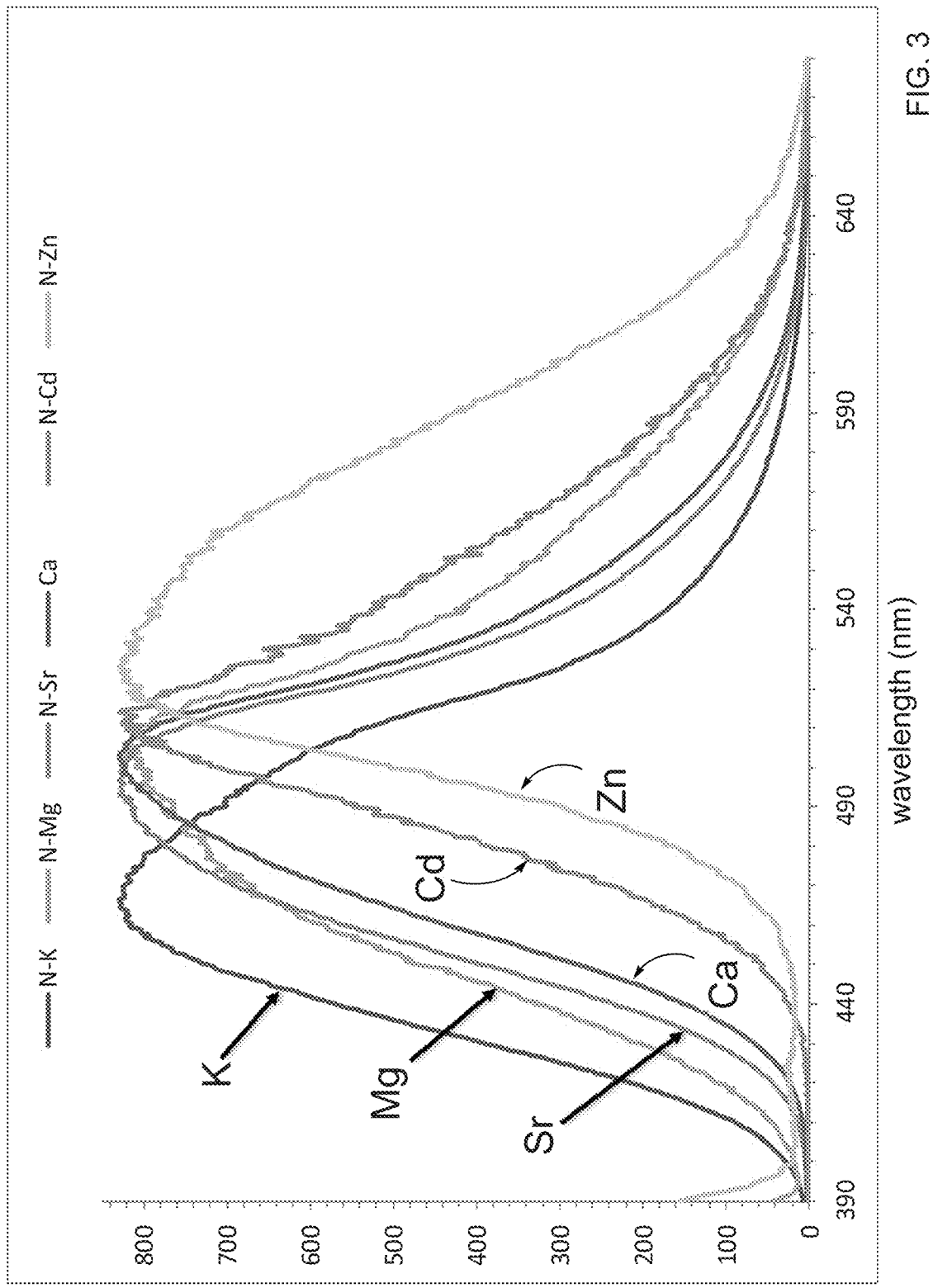
FIG. 3 shows the normalized emission spectra of D1 and some of the complexes in water-saturated acetonitrile. The concentration of D1 was 0.004 M, and the metal ion concentration was 0.04 M. The metal ions are added as perchlorates or acetates. The solutions were exposed to UV light having an excitation wavelength of 285 nm or larger. From left to right, the legend reads: $K^+$, $Mg^{2+}$, $Sr^{2+}$, $Ca^{2+}$, $Cd^{2+}$, $Zn^{2+}$.

Comparing FIG. 1 and FIG. 2, there is a clear difference in color when a metal ion is present. It is noted that the color for a given metal ion may change between the solution and the solid state. However, each color is still unique for a given metal ion. Note that nickel ($Ni^{2+}$) quenched the intrinsic blue color of FIG. 3 shows the normalized emission spectra for six complexes, indicating that the different metal ions can be distinguished from each other reasonably well.

Figure 4:
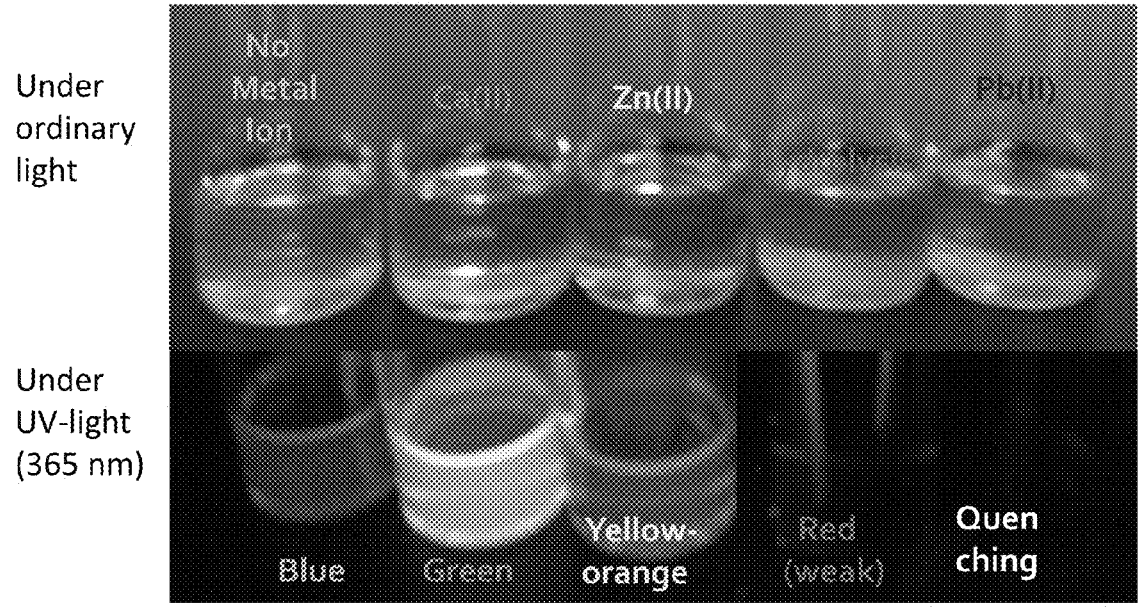
FIG. 4 is a set of pictures showing the change in color of derivative compound D1 in the absence and presence of various metal ions ($Ca^{2+}$, $Zn^{2+}$, $H^+$, $Pb^{2+}$) in solution (perchlorate salts), both under ordinary light and under UV light (365 nm). The solvent was acetonitrile, the concentration of D1 was 0.0001 M, and one equivalent of the metal perchlorate salt was added. For $H^+$, an aluminum perchlorate salt was used, which produced acid ($H^+$) that protonated the ligand.

FIG. 4 shows solutions of D1 with various metal ions in solution under both ordinary light and UV light (365 nm). Under UV light, the D1 solution alone is blue. With Ca(II), the solution is green. With Zn(II), the solution is yellow-orange. With Al(III) perchlorate, the solution is red. This red color resulted from an unexpected hydrolysis reaction that produced acid ($H^+$). The protonated ligand provided the red color. With Pb(II), the solution is black, i.e. the blue color that would other be visible has been quenched.

Figure 5:
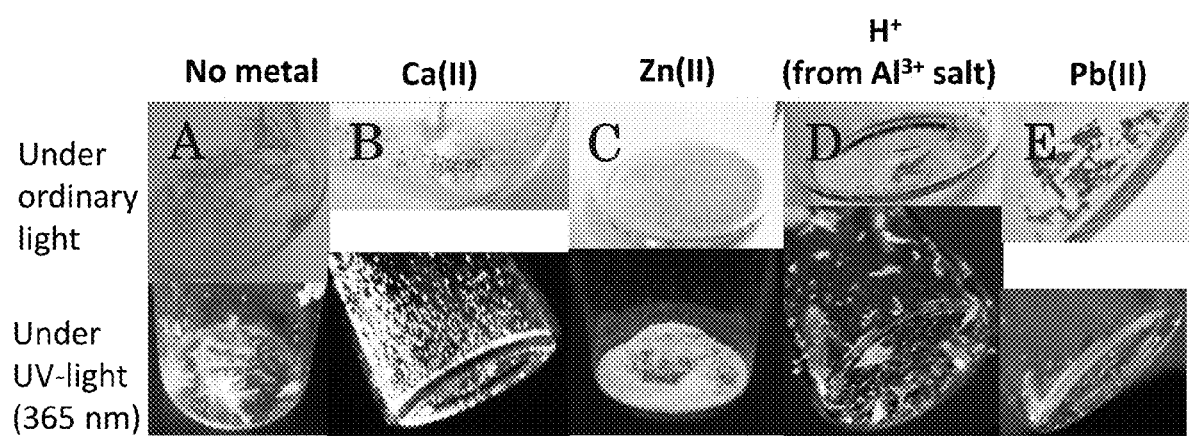
FIG. 5 is a set of pictures showing the change in color of derivative compound D1 in the absence and presence of various metal ions or acids ($Ca^{2+}$, $Zn^{2+}$, $H^+$, $Pb^{2+}$) in the solid state, both under ordinary light and under UV light (365 nm). Perchlorate salts were used. When the aluminum salt was used, an unexpected hydrolysis produced acid ($H^+$) which protonated the ligand.

FIG. 5 is a set of pictures showing fluorescence of D1 in the solid state, under ordinary light (top row) and under UV light (365 nm) (bottom row). In column A, the free ligand sample (i.e. no metal ions) is blue. In column B with Ca(II), the powder is green. In column C with Zn(II), the powder is yellow. In column D with Al(III), the powder is red. Again, this appears to be due to acid ($H^+$). In column E with Pb(II), the powder is non-fluorescent.

Figure 6:
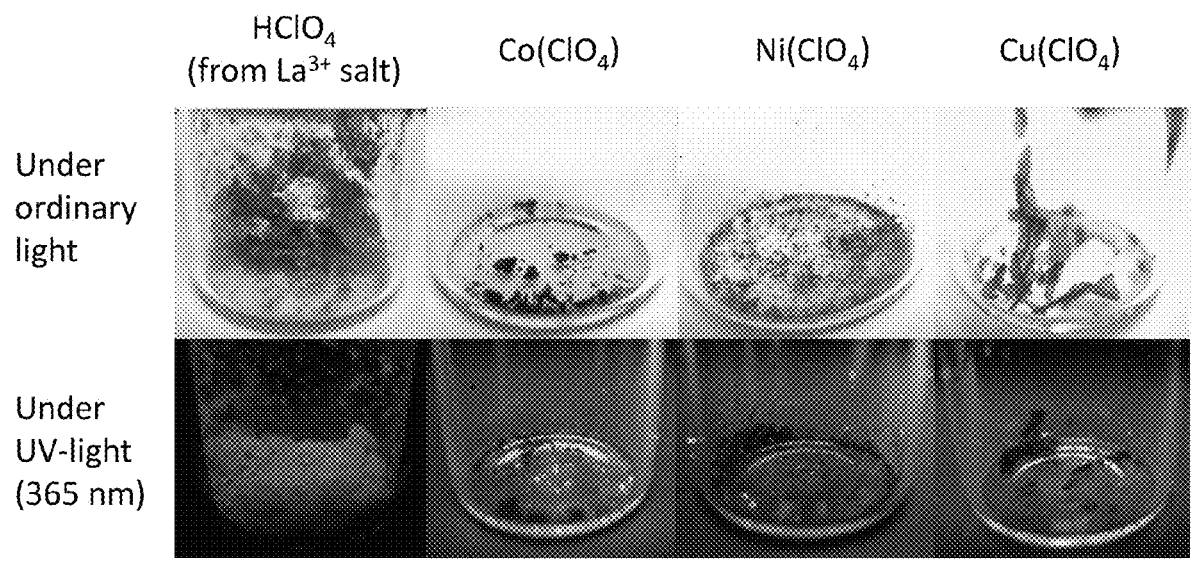
FIG. 6 is a set of pictures showing the change in color of derivative compound D1 in the absence and presence of various metal ions or acids ($H^+$, $Co^{2+}$, $Ni^{2+}$, $Cu^{2+}$) in the solid state, both under ordinary light and under UV light (365 nm). Perchlorate salts were used. The lanthanum salt produced acid ($H^+$) which protonated the ligand, as shown in the figure.

FIG. 6 is a set of pictures showing fluorescence of D1 in the solid state, under ordinary light (top row) and under UV light (365 nm) (bottom row). In the first column ligand treated with La(III) perchlorate produced a powder that fluoresces red. Again, acid ($H^+$) was produced and its X-ray crystal structure showed a protonated ligand. In the second column with Co(II), the powder is non-fluorescent. In the third column with Ni(II), the powder is non-fluorescent. In the fourth column with Cu(II), the powder is non-fluorescent.

Figure 7:
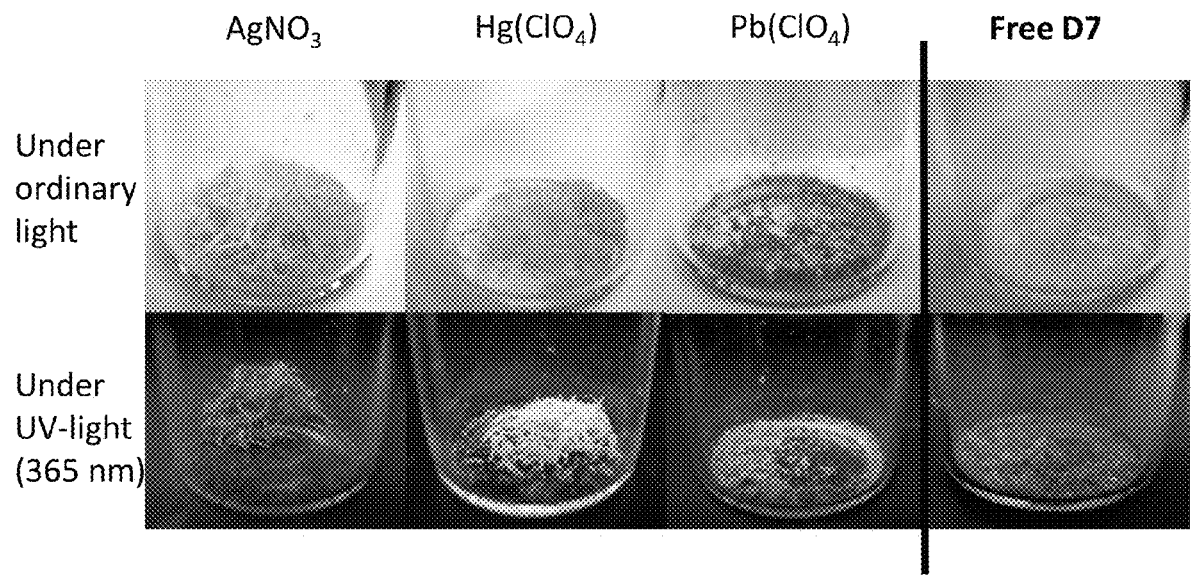
FIG. 7 is a set of pictures showing the change in color of derivative compound D1 in the absence and presence of various metal ions or acids ($AgNO_3$, $Hg^{2+}$, $Pb^{2+}$) and of the free compound D7 (no metal ion) in the solid state, both under ordinary light and under UV light (365 nm).

FIG. 7 is a set of pictures showing fluorescence of D1 in the solid state, under ordinary light (top row) and under UV light (365 nm) (bottom row). In the first column with silver nitrate ($AgNO_3$), the powder is non-fluorescent. In the second column with Hg(II), the powder barely fluoresces. In the third column with Pb(II), the powder is non-fluorescent. In the fourth column, the free compound D7 is shown, and is non-fluorescent.

Figure 22:
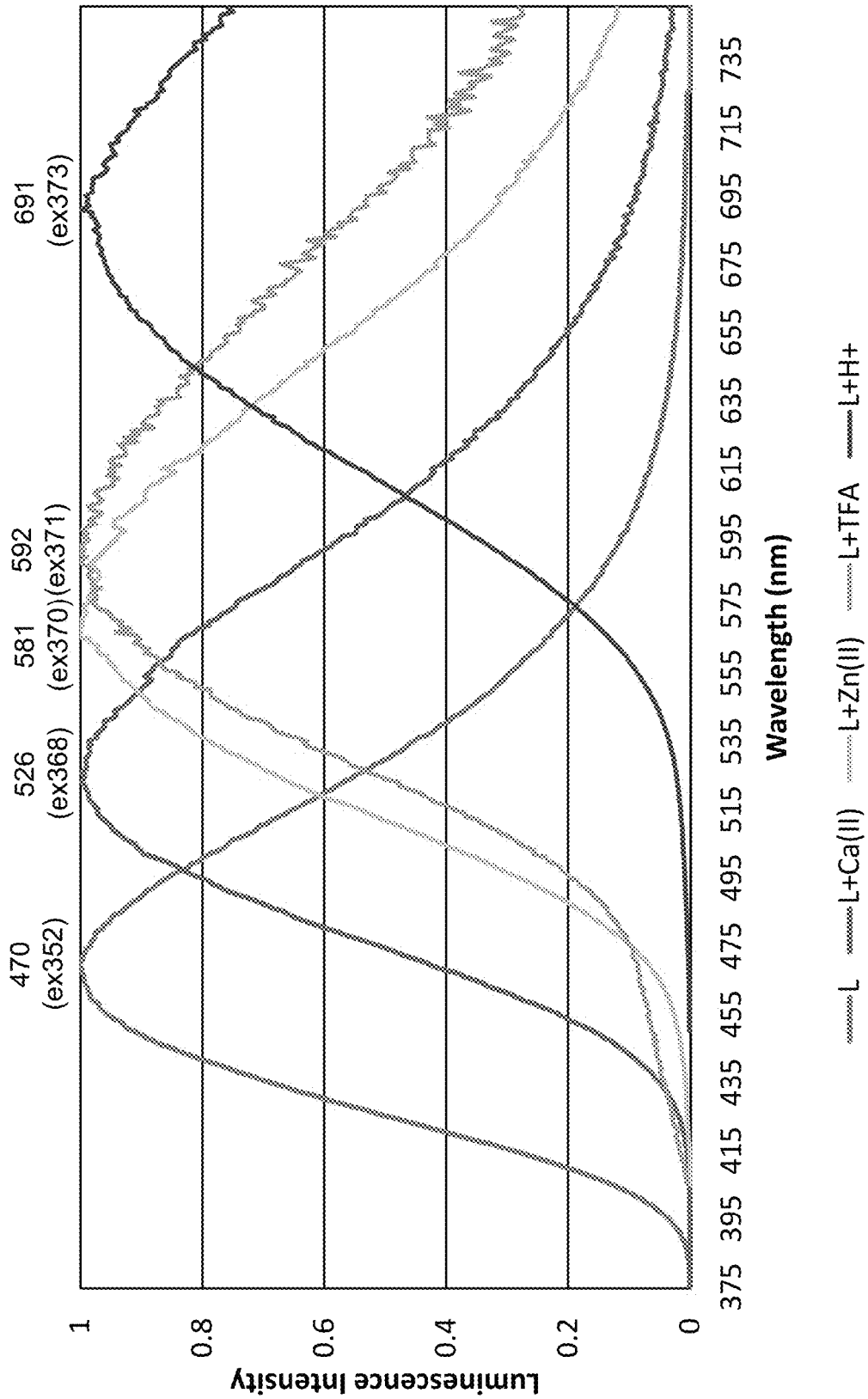
FIG. 22 shows the normalized emission spectra of D1 (marked as L) and some complexes in dry acetonitrile. The concentration of D1 was 0.00013 M, and the metal ion concentration was 0.00012 M. The metal ions are added as perchlorates or acetates. The y-axis is luminescence intensity, and the x-axis is wavelength in nanometers. The free ligand L had maximum emission at 470 nm. The L+Ca(II) complex had maximum emission at 526 nm. The L+Zn(II) complex had maximum emission at 581 nm. The L+trifluoroacetate complex had maximum emission at 592 nm. The L+H$^+$ complex had maximum emission at 691 nm. The L+H$^+$ complex was formed using aluminum chloride dissolved in TFA and diluted with dry MeCN, and it is likely that HCl was produced in situ, and that this is protonating the ligand.

FIG. 22 shows the normalized emission spectra of D1 (marked as L) alone and in four different complexes in solution. Each has a different wavelength of maximum emission, indicating that the different metal ions can be distinguished from each other reasonably well.

Figure 23:
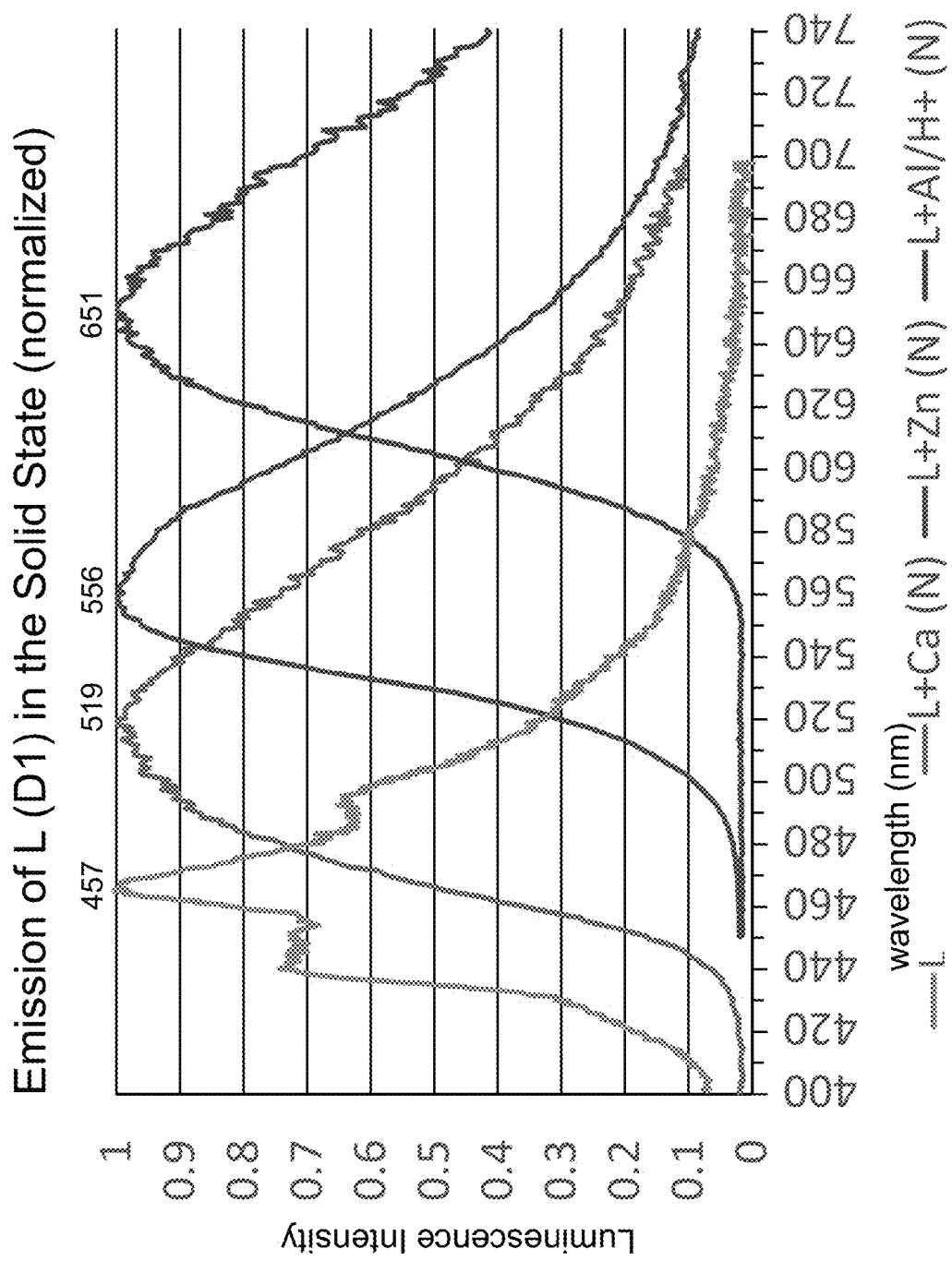
FIG. 23 shows the normalized emission spectra of D1 (marked as L) and some complexes in the solid state. The y-axis is luminescence intensity, and the x-axis is wavelength in nanometers. The free ligand L had maximum emission at 457 nm. The L+Ca complex had maximum emission at 519 nm. The L+Zn complex had maximum emission at 556 nm. Al/H$^+$ complex had maximum emission at 651 nm. This latter complex is a protonated ligand obtained by using aluminum perchlorate, which produced acid in situ.

FIG. 23 shows the normalized emission spectra of D1 (marked as L) alone and in three different complexes in the solid state. Each has a different wavelength of maximum emission, indicating that the different metal ions can be distinguished from each other reasonably well. The curve labeled Al/H+(N) was obtained by using protonated ligand obtained by treating the ligand with aluminum perchlorate.

Figure 24:
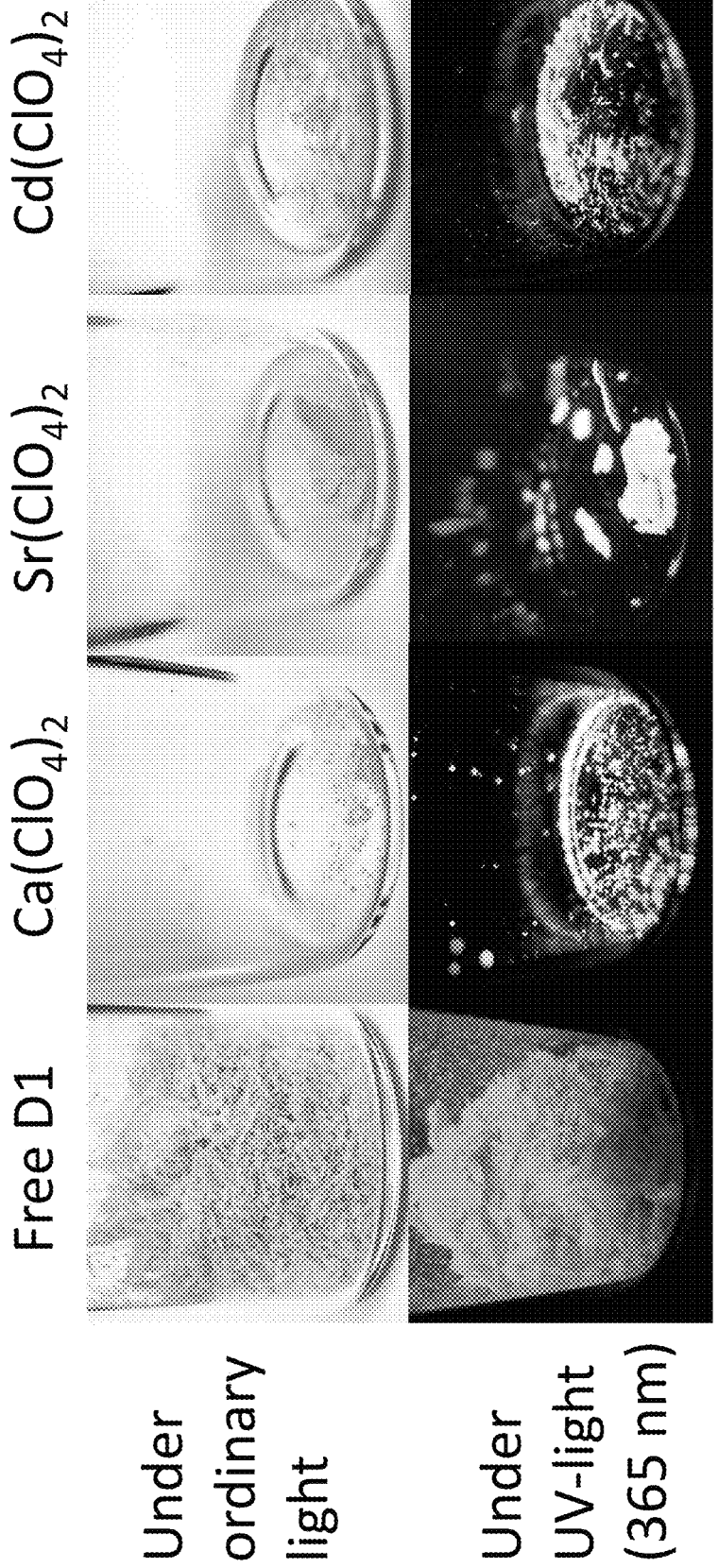
FIG. 24 is a set of pictures showing the change in color of complexes of D1 with perchlorate salts of various metal ions (Ca$^{2+}$, Sr$^{2+}$, Cd$^{2+}$) in the solid state, both under ordinary light and under UV light (365 nm).
Figure 25:
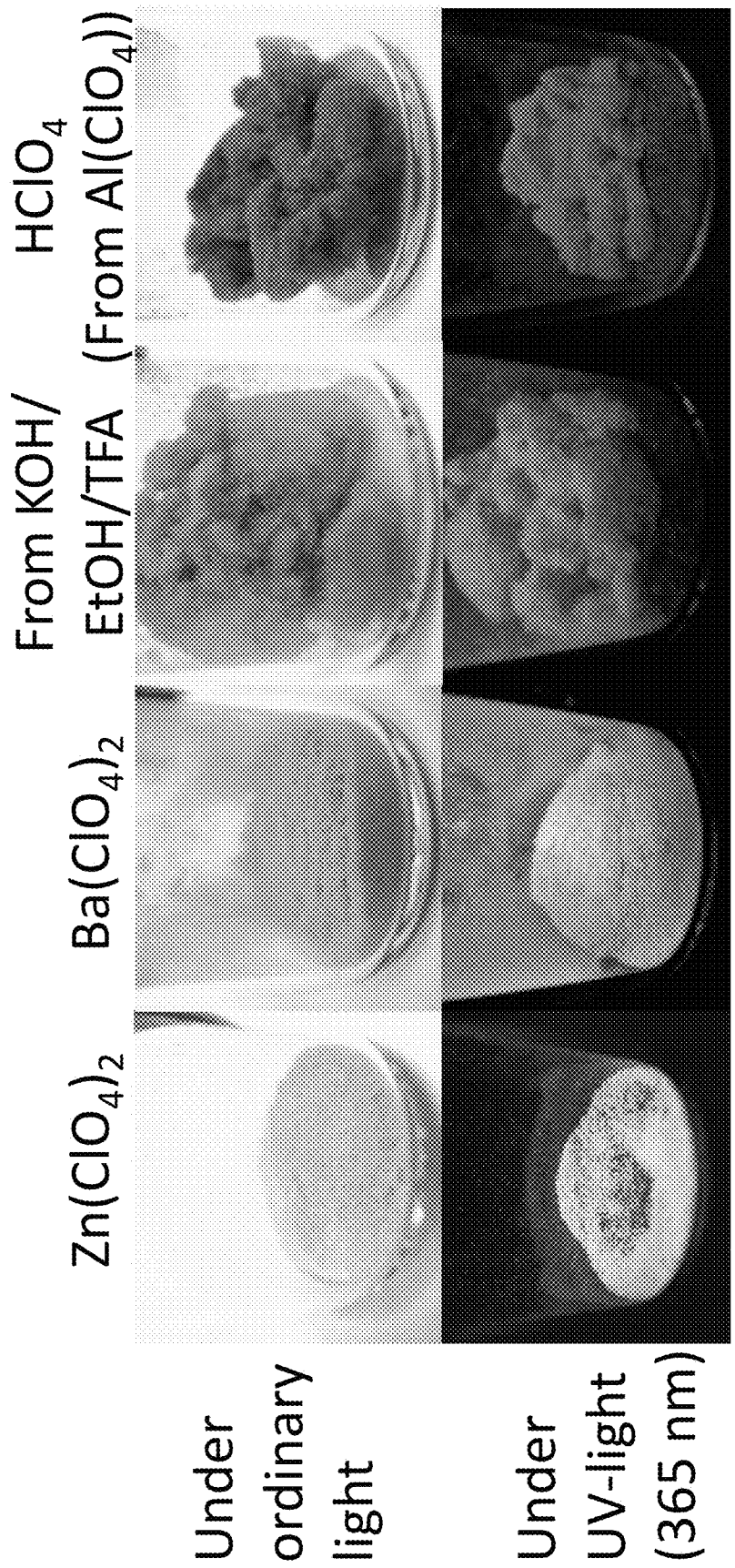
FIG. 25 is a set of pictures showing the change in color of complexes of D1 with salts of various metal ions (Zn$^{2+}$, Ba$^{2+}$, H$_a^+$, H$_b^+$) in the solid state, both under ordinary light and under UV light (365 nm). The zinc and barium are perchlorate salts. The complex labeled "From KOH/EtOH/TFA" was obtained from a solution of KOH and ethanol upon addition of TFA. It is unclear what is causing the orange color, but it is most likely acid, therefore the label "H$_a^+$". The HClO$_4$ complex was obtained by using aluminum perchlorate, which produced acid (H$^+$) that protonated the ligand.

FIG. 24 and FIG. 25 are sets of pictures showing the fluorescence of complexes of D1 with salts of various metal ions in the solid state, both under ordinary light and under UV light (365 nm).

In FIG. 24, the free ligand D1 (i.e. no metal ions) is blue. For $Ca^{2+}$, $Sr^{2+}$, and $Cd^{2+}$, the color is green.

In FIG. 25, the salt of $Zn^{2+}$ fluoresces yellow. The salt of $Ba^{2+}$ fluoresces orange. The orange sample labeled "From KOH/EtOH/TFA" was obtained from an ethanolic solution of KOH after adding TFA. It is likely that the ligand is protonated rather than binding K. The red sample labeled "$HClO_4$" was obtained by using aluminum perchlorate, which produced acid ($H^+$).

Scaffold S2

The second scaffold compound (S2) is a combination of two hydroxyquinolines, i.e. having two phenyl rings and two pyridine rings. The second scaffold compound is based off of a dimethoxy-2,2'-biquinoline, and has the following formula:

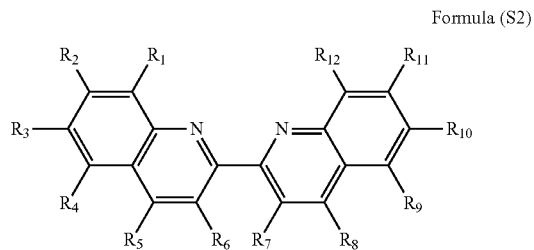

Formula (S2)

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group, and wherein $R_6$ and $R_7$ may be joined together via an alkyl or substituted alkyl linkage to form a cyclic ring;

wherein at least one of $R_1$ to $R_6$ is —OR', —SR', —COR', or —NR'$_2$;

at least one of $R_7$ to $R_{12}$ is —OR", —SR", —COR", or —NR"$_2$; and wherein R' and R" are independently alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound.

When $R_6$ and $R_7$ are not joined together, then unlike the compound of Formula (S1), the two nitrogen atoms of the pyridine rings are not fixed in position relative to each other. Thus, the cavity size of (S2) can change more readily compared to (S1). However, if $R_6$ and $R_7$ are joined together, then Formula (S2) can overlap with Formula (S1) when $R_6$ and $R_7$ are —$CH_2$—$CH_2$—.

The compound of Formula (S2) can be asymmetrical or symmetrical. In particular embodiments of Formula (S2), the compound is symmetrical. In specific embodiments of Formula (S2), at least one of $R_1$ to $R_5$ is —OR', and at least one of $R_8$ to $R_{12}$ is —OR". In further specific embodiments of Formula (S2), only one of $R_1$ to $R_5$ is —OR', and only one of $R_8$ to $R_{12}$ is —OR". The —OR' and —OR" groups are usually located symmetrically. In particular embodiments, the —OR' and —OR" groups are located at $R_1$ and $R_{12}$.

In more specific embodiments of Formula (S2), R' and R" are chelating ligands, and the heteroatom of the chelating ligand is present as a carbonyl group. In other embodiments, the chelating ligand is —CO—R, —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, —(CH$_2$)$_n$—[O—(CH$_2$)$_k$]$_m$—OR, or salts thereof; wherein k, m, and n are independently integers from 0 to 10 and k+m+n≥1 (i.e. greater than or equal to 1); R, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic; and Z is sulfur or oxygen. Specific examples of such chelating ligands include —CH$_2$—CO—OCH$_3$ and —CH$_2$—CO—O$^-$. In other specific embodiments, R' and R" are alkyl or substituted alkyl. It is believed that chelating ligands incorporating sulfur atoms may lead to selectivity towards Hg(II) ions. It should be noted that R' and R" are usually the same. It should also be noted that when $R_1$ and $R_{12}$ are hydroxyl, the resulting compound is not luminescent.

In other embodiments of Formula (S2), $R_4$ and $R_9$ are the same, and are not hydrogen. In additional embodiments, $R_4$ and $R_9$ are not hydrogen or alkoxy. For example, in particular embodiments, $R_4$ and $R_9$ are halogen, aryl, substituted aryl, alkynyl, or substituted alkynyl. In particular embodiments, $R_2$, $R_3$, $R_5$, $R_6$, $R_7$, $R_8$, $R_{10}$, and $R_{11}$ are hydrogen, while $R_4$ and $R_9$ are the same and are not hydrogen or alkoxy. In yet other embodiments, all of $R_2$-$R_{11}$ are hydrogen.

In additional specific embodiments of Formula (S2), the —OR', —SR', —COR', —NR'$_2$, —OR", —SR", —COR", or —NR"$_2$ groups are located at $R_1$ and $R_{12}$. In these embodiments, $R_4$ and $R_9$ are the same, and are not hydrogen or a water-solubilizing group. Put another way, $R_4$ and $R_9$ are independently selected from halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, and sulfide.

Specific derivatives of the scaffold compound (S2) include those of formulas (B1)-(B3):

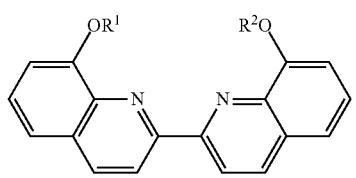

(B1)

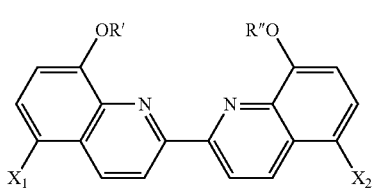

(B2)

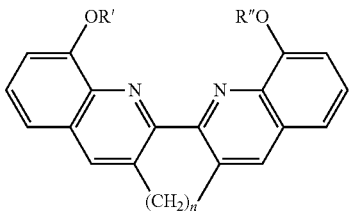

(B3)

wherein R$^1$ and R$^2$ are independently alkyl or substituted alkyl; R' and R" are independently alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom; and $X_1$ and $X_2$ are independently halogen; and n is an integer from 1 to 10 in (B3). In a specific embodiment of B1, R$^1$ and R$^2$ are —CH$_3$.

Macrocyclic compounds of Formula (S2) and polymers using the compounds of Formula (S2) as a monomer are also contemplated. In the macrocyclic compounds, a linking moiety connects the two oxygen atoms of the —OR' and the —OR" groups together. Macrocyclic compounds of Formula (S2) have the general structure of Formula (S2-M):

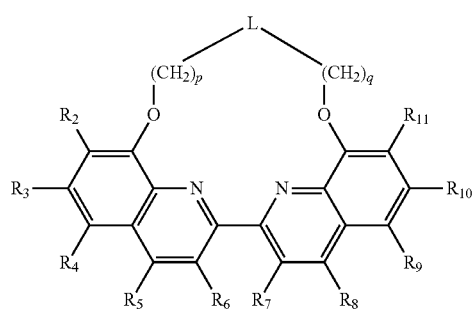

Formula (S2-M)

wherein $R_2$-$R_{11}$ are as defined above, p and q are independently integers from 1 to 10;

and L is a linking group. Again, the linking group can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino. Those linking groups illustrated in Formulas (M1)-(M7) can also apply here.

In the polymers, the monomers are linked through the oxygen atoms, or through the carbon atoms on the phenyl rings. Specific examples follow the general formula shown above with respect to Formula (S1), and are illustrated below as Formulas (P7)-(P12). Again, for simplicity, the —OR' and —OR" groups are illustrated as being located at $R_1$ and $R_{12}$, though they can generally be located as described above.

Formula (P7)
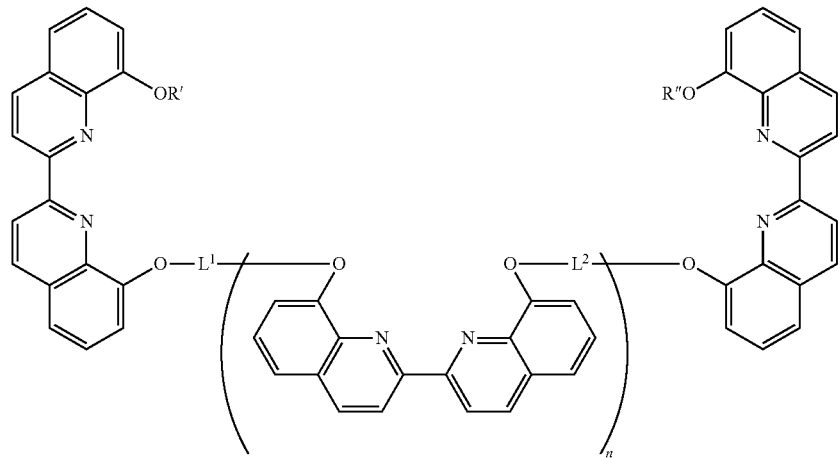
Formula (P8)
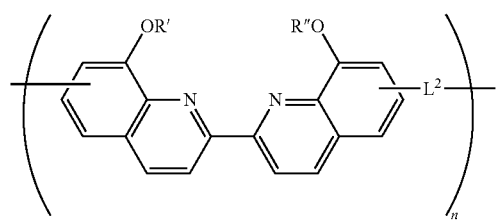
Formula (P9)
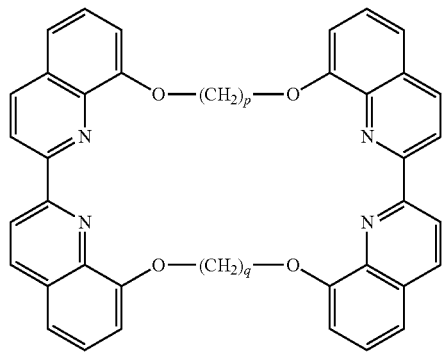
Formula (P10)
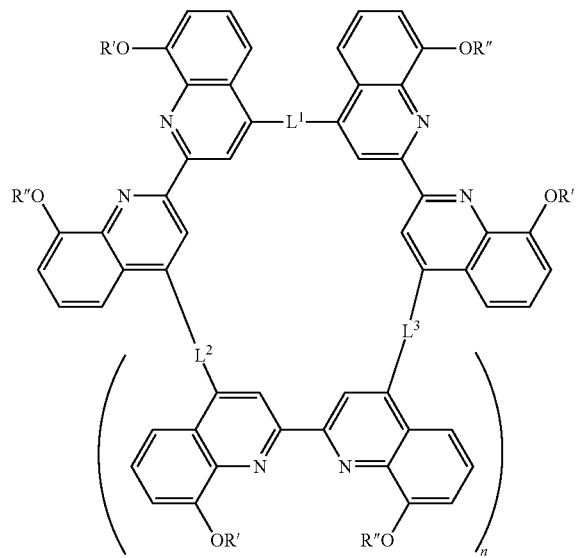
Formula (P11)
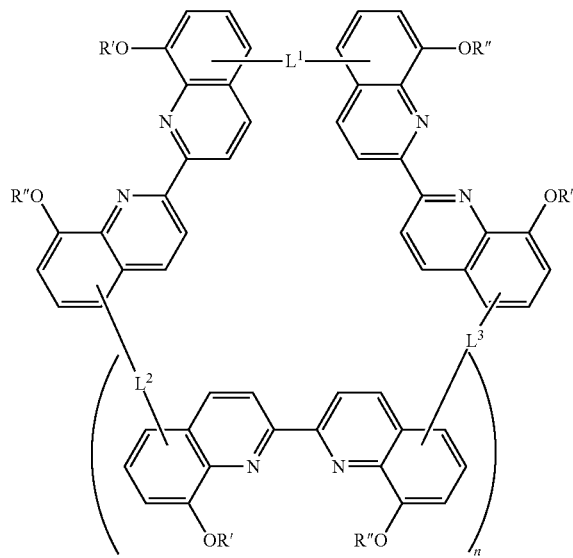

Formula (P12)

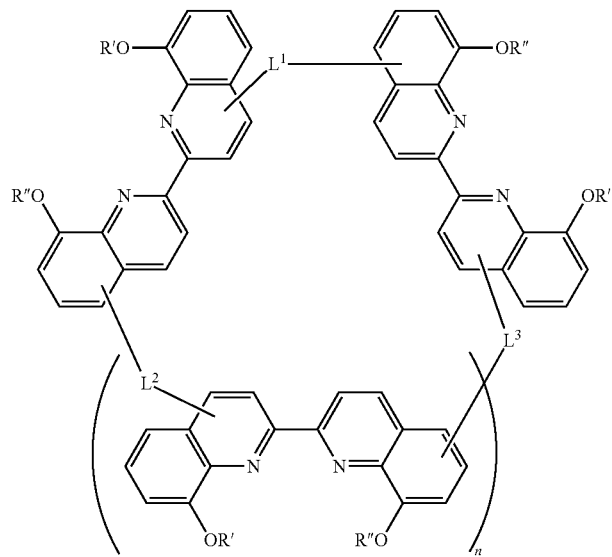

wherein $L^1$, $L^2$, and $L^3$ are independently linking groups; R' and R" are independently alkyl, substituted alkyl, aryl, substituted aryl, heteroaryl, substituted heteroaryl, heterocyclic, substituted heterocyclic, or a chelating ligand comprising at least one linking group and at least one heteroatom; and n is the degree of polymerization, and is from 0 to about 100. In (P8), w is the degree of polymerization, and is from 2 to about 100. Again, the linking groups can be made from any suitable combination of atoms, including alkyl, substituted alkyl, aryl, substituted aryl, heteroaryl, substituted heteroaryl, heterocyclic, substituted heterocyclic, polyether, and amino. For example, the linking groups could be alkyl. It is noted that the polymers can be homopolymers or copolymers (i.e. two or more different monomers).

For clarity, it is noted that in (P10)-(P12), $L^2$ is within the repeating unit, while $L^3$ is outside the repeating unit. It should be noted that in (P11) and (P12), the linkages $L^1$, $L^2$, and $L^3$ can be through any of the carbon atoms on the phenyl ring, (i.e. ortho-, meta-, or para-) depending on the identity of the linkage. It should be noted that in (P10)-(P12), depending on the location of the linkages and the number of repeating units, the various portions of the cyclic polymer can rotate so that the R' and R" groups are directed to the interior or the exterior of the cyclic polymer, whichever is more stable.

Manufacture of Scaffolds S1 and S2

The compounds of Formula (S1) and Formula (S2) can be made using a Friedlander condensation involving a diketone and at least one o-aminobenzaldehyde (depending on whether the compound is symmetric or asymmetric). When making a compound of Formula (S1), the diketone is a 1,2-cyclohexanedione. When making a compound of Formula (S2), the diketone is a 2,3-butadione.

Synthesis Scheme 1 illustrates a two-step reaction to produce a compound of Formula (51) using two aminobenzaldehydes (AA1) and (AA2) and a diketone (S1a). Synthesis Scheme 2 illustrates a two-step reaction to produce a compound of Formula (S2) using two aminobenzaldehydes (AA1) and (AA2) and a diketone (S2a). For simplicity, the —OR' and —OR" groups are illustrated below at the $R_1$ and $R_{12}$ positions. Of course, the relative locations of the amino group, the —OR'/—OR" group, and the aldehyde group will change depending on the location of the —OR'/—OR" group.

Synthesis Scheme 1:

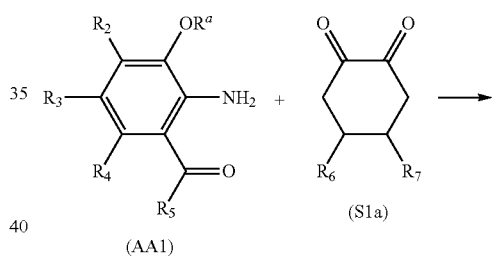

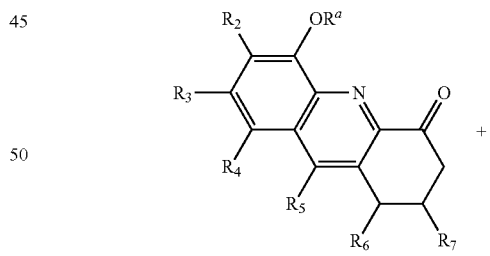

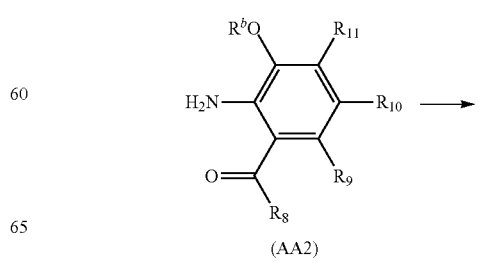

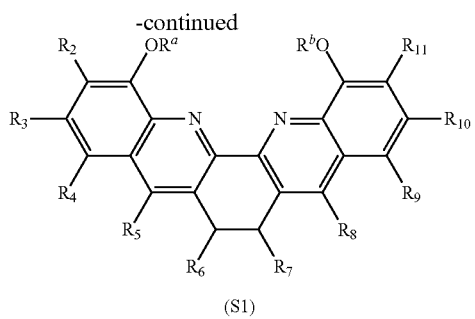

(S1)

Synthesis Scheme 2:

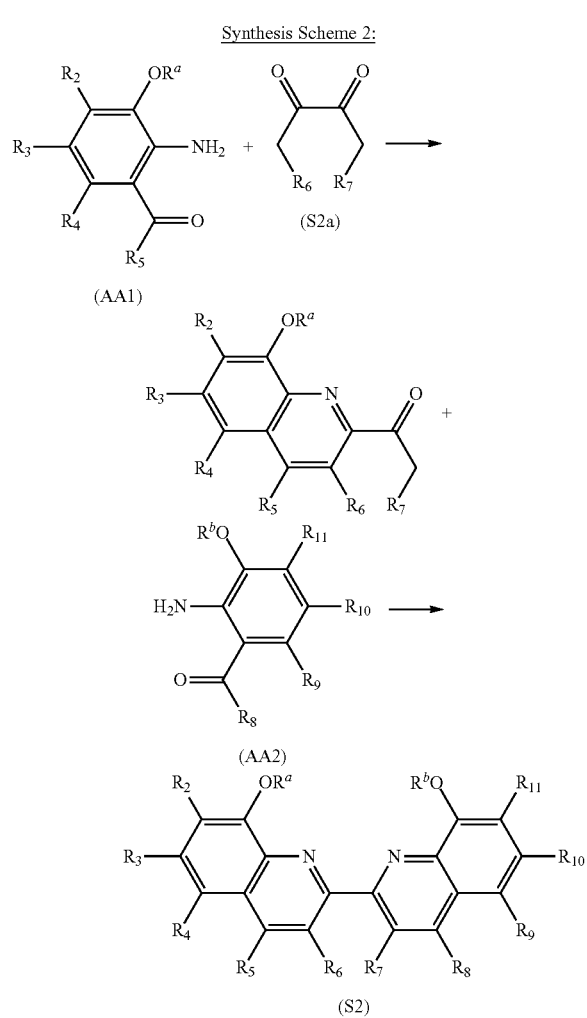

(S2)

The reaction typically occurs in the presence of a base and an alcohol, e.g. potassium hydroxide (KOH) and ethanol (EtOH). Once the aminobenzaldehyde is consumed, trifluoroacetic acid is added to dehydrate and/or precipitate the compound out of solution. The use of this dehydrating reagent is important in the synthesis of the compound.

It should be noted that the aminobenzaldehydes (AA1) and (AA2) can be the same. In this event, the reactions would be one-step reactions using two moles of the aminobenzaldehyde per mole of diketone.

The substituents $R^a$ and $R^b$ can be the final desired ligands, or can be intermediate ligands that are substituted to obtain the final desired ligands R' and R", whether to form the compounds, or to obtain macrocyclic compounds or linkers to obtain polymers. The compound containing $R^a$ and $R^b$ can be reduced with hydrobromic acid to obtain —OH groups, and then be reacted with reactants of the formula $L^a$-R' and $L^b$-R", wherein $L^a$ and $L^b$ are leaving groups known in the art, to obtain the final desired ligands.

Scaffold S3

The third scaffold compound (S3) is a combination of two quinolines (each having a phenyl ring and a pyridine ring) and one pyridine ring bridging the two quinoline rings. The third scaffold compound has the following formula:

Formula (S3)

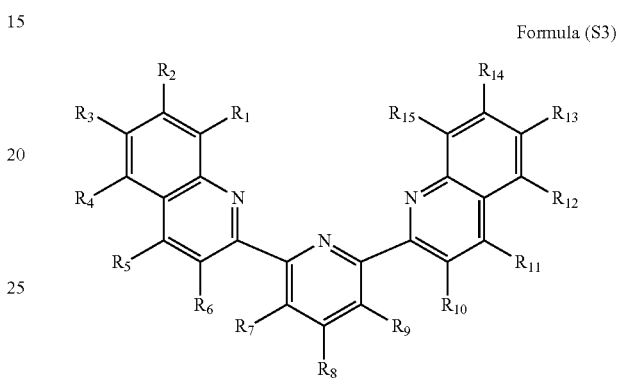

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_8$ is —OR', —SR', —COR', or —NR'''2; at least one of $R_9$ to $R_{15}$ is —OR", —SR", —COR", or —NR""2;

wherein R' and R" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound; and wherein R''' and R"" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound.

Again, it should be noted that the nitrogen atoms of the two quinoline rings can move relative to the nitrogen atom of the central pyridine ring. Thus, the cavity size can vary.

The compound of Formula (S3) can be asymmetrical or symmetrical. In particular embodiments of Formula (S3), the compound is symmetrical. In specific embodiments of Formula (S3), at least one of $R_1$ to $R_5$ is —OR', and at least one of $R_{11}$ to $R_{15}$ is —OR". In further specific embodiments of Formula (S3), only one of $R_1$ to $R_5$ is —OR', and only one of $R_{11}$ to $R_{15}$ is —OR". The —OR' and —OR" groups are usually located symmetrically. In particular embodiments, the —OR' and —OR" groups are located at $R_1$ and $R_{15}$.

In more specific embodiments of Formula (S3), R' and R" are chelating ligands, and the heteroatom of the chelating ligand is present as a carbonyl group. In other embodiments, the chelating ligand is —CO—R, —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, —(CH$_2$)$_n$—[O—(CH$_2$)$_k$]$_m$—OR, or salts thereof; wherein k, m, and n are independently integers from 0 to 10 and k+m+n≥1 (i.e. greater than or equal to 1); R, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic; and Z is sulfur or oxygen. Specific examples of such chelating ligands include —CH$_2$—CO—OCH$_3$, —CO—CH$_3$, and —CO—C(CF$_3$)(OCH$_3$)(C$_6$H$_5$). It is believed that chelating ligands incorporating sulfur atoms may lead to selectivity towards Hg(II) ions. It should be noted that R' and R" are usually the same. In particular embodiments, all of $R_2$-$R_{14}$ are hydrogen.

Also falling within the scope of formula (S3) are symmetric compounds of formula (S3-I):

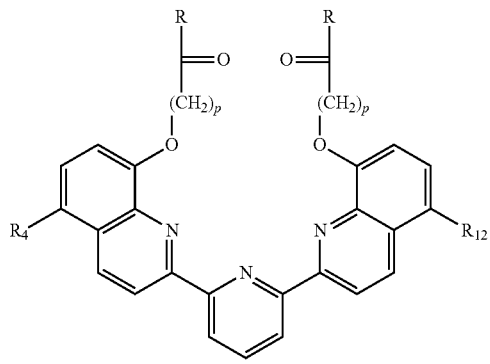

(S3-I)

wherein p is an integer from 0 to 4; R is hydrogen, hydroxyl or a salt thereof, alkyl, substituted alkyl, alkoxy, or substituted alkoxy; and $R_4$ and $R_{12}$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group. In particular embodiments of (S3-I), $R_4$ and $R_{12}$ are the same, and are not hydrogen.

Specific derivatives of the scaffold compound (S3) include those of formulas (L1), (L2), and (L3):

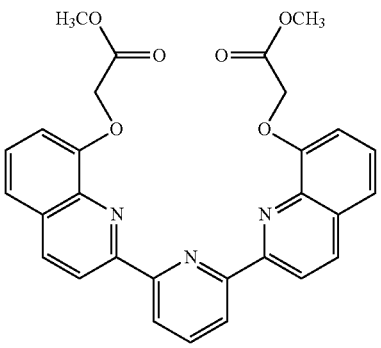

(L1)

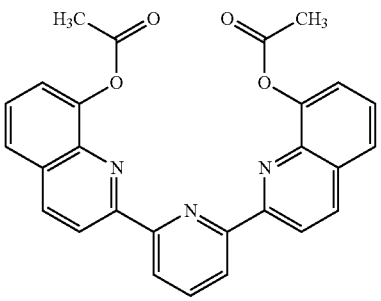

(L2)

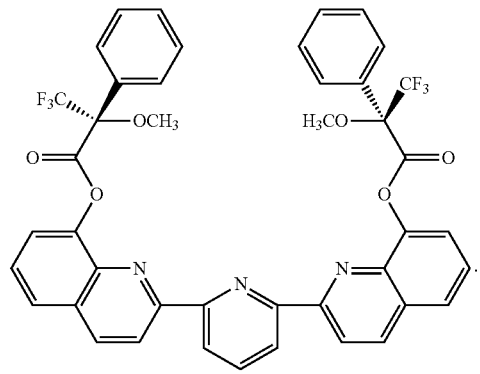

(L3)

Compound (L1) is also known as 2,6-bis[8-(methoxycarbonylmethoxy)quinolin-2-yl]pyridine. Compound (L2) is also known as 2,6-bis[8-(acetoxy)quinolin-2-yl]pyridine. Compound (L3) is also known as 2,6-bis[8-((2R)-2-trifluoromethyl-2-methoxy-2-phenylacetoxy)quinolin-2-yl]pyridine. These are heptadentate compounds.

Macrocyclic compounds of Formula (S3) and polymers using the compounds of Formula (S3) as a monomer are also contemplated. In the macrocyclic compounds, a linking moiety connects the two oxygen atoms of the —OR' and the —OR" groups together. Macrocyclic compounds of Formula (S3) may have the general structure of Formula (S3-M):

Formula (S3-M)

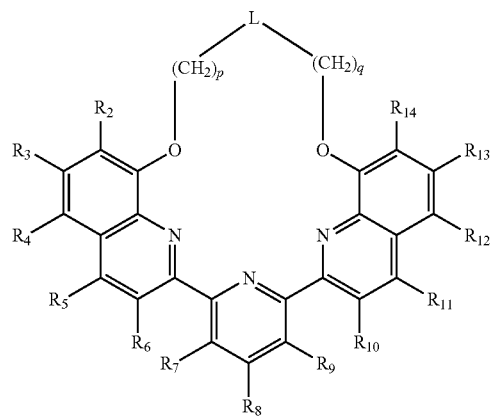

wherein $R_2$-$R_{14}$ are as defined above, p and q are independently integers from 1 to 10;

and L is a linking group. Again, the linking group can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino. Those linking groups illustrated in Formulas (M1)-(M7) can also apply here.

In the polymers, the monomers are linked through the phenolic oxygen atoms, or through the carbon atoms on the phenolic rings. Specific examples of polymers are illustrated below as Formulas (P13)-(P20). For simplicity, the —OR' and —OR" groups are illustrated as being located at $R_1$ and $R_{15}$, though they can generally be located as described above.

Formula (P13)

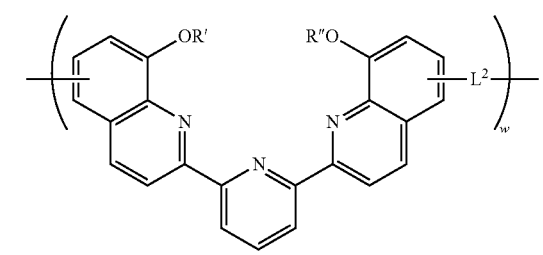

Formula (P14)

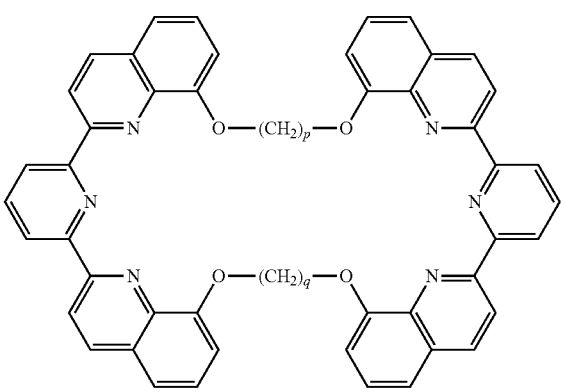

Formula (P15)

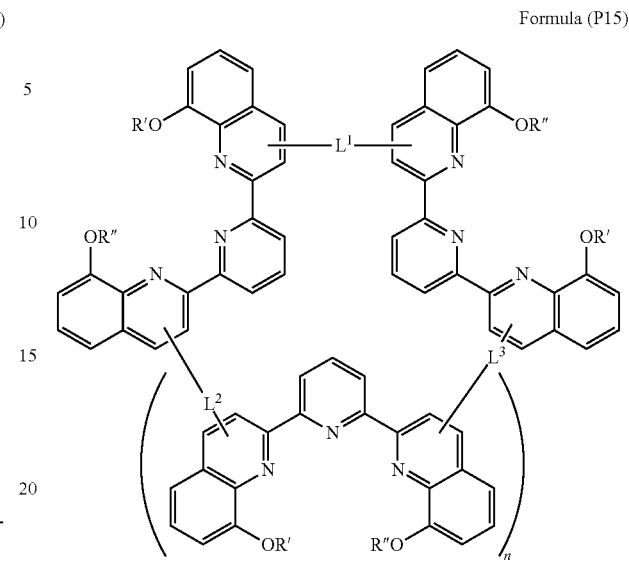

Formula (P16)

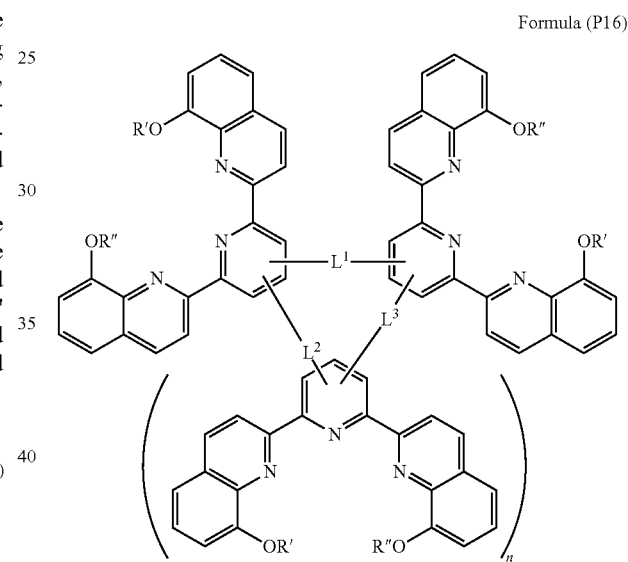

Formula (P17)

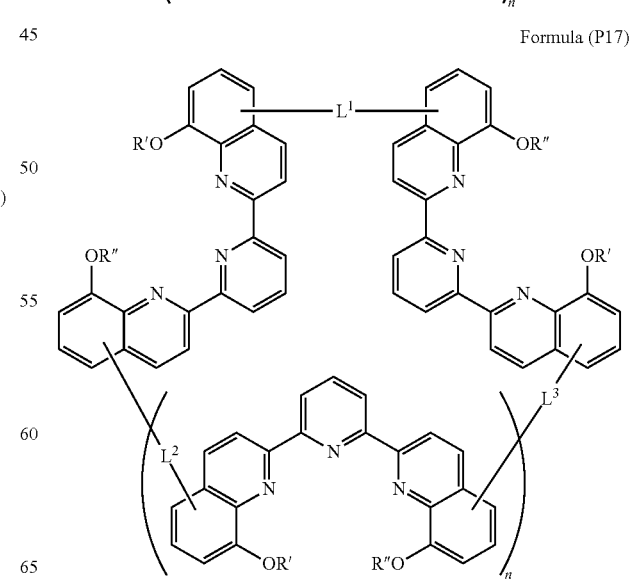

Formula (P18)

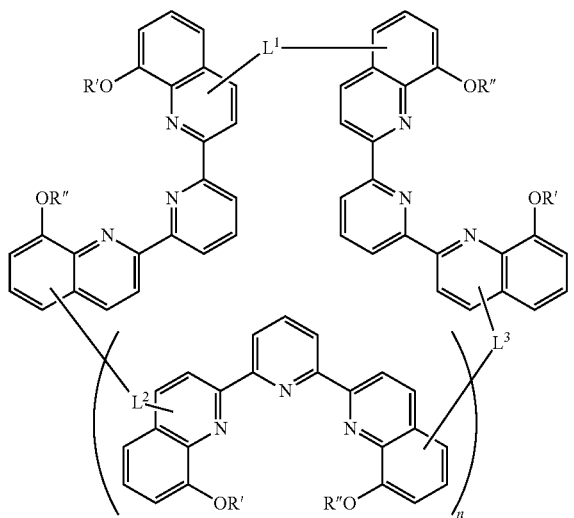

Formula (P19)

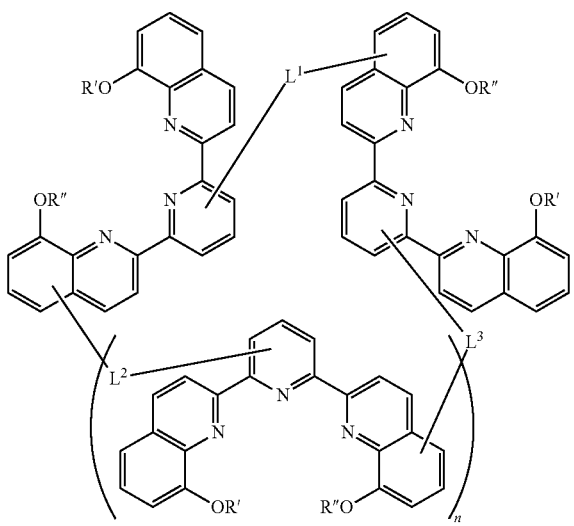

Formula (P20)

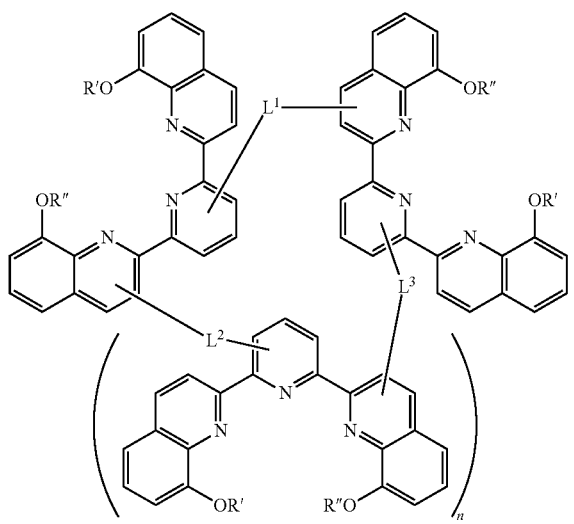

wherein $L^1$, $L^2$, and $L^3$ are independently linking groups; R' and R" are independently a chelating ligand comprising at least one linking group and at least one heteroatom; and n is the degree of polymerization, and is from 0 to about 100. In (P13), w is the degree of polymerization, and is from 2 to about 100. Again, the linking groups can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino. For example, the linking groups could be alkyl. It is noted that the polymers can be homopolymers or copolymers (i.e. two or more different monomers).

For clarity, it is noted that in (P15)-(P20), $L^2$ is within the repeating unit, while $L^3$ is outside the repeating unit. It should be noted that in (P15)-(P20), the linkages $L^1$, $L^2$, and $L^3$ can be through any of the carbon atoms on the given ring, depending on the identity of the linkage. In particular embodiments of (P16), the linkage is through the carbon atom that is meta- (either one or both) or para- to the nitrogen atom. It should be noted that in (P15)-(P20) the various portions of the cyclic polymer can rotate so that the R' and R" groups are directed to the interior or the exterior of the cyclic polymer, whichever is more stable.

Manufacture of Scaffold S3

The manufacture of the base scaffold compound (S3), where all of the R groups, R', and R" are all hydrogen, is known in the chemical literature. This base compound can be reacted with reactants of the formula $L^a$-R' and $L^b$-R", wherein $L^a$ and $L^b$ are leaving groups known in the art, to obtain the final desired ligands.

Scaffold S4

The fourth scaffold compound (S4) is a combination of two quinolines (each having a phenyl ring and a pyridine ring) attached at the opposite ends of a tetrahydroacridine. The resulting compound has a central pyridine ring, two cyclohexane rings, two flanking pyridine rings, and two terminal phenyl rings. The fourth scaffold compound has the following formula:

Formula (S4)

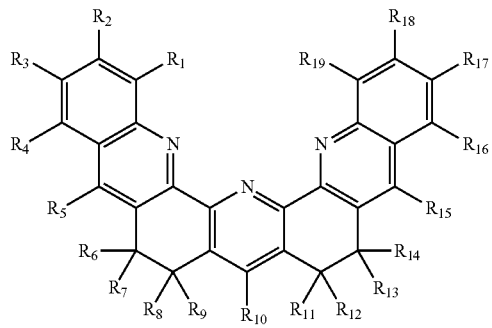

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_5$ and $R_{10}$ is —OR', —SR', —COR', or —NR'"2;

at least one of $R_{15}$ to $R_{19}$ is —OR", —SR", —COR", or —NR""2;

wherein R' and R" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound; and wherein R'" and R"" are independently hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound.

It should be noted that the three nitrogen atoms of the pyridine rings are fixed in position relative to each other. This reduces the ability of the compound to vary the cavity size.

The compound of Formula (S4) can be asymmetrical or symmetrical. In particular embodiments of Formula (S4), the compound is symmetrical. In specific embodiments of Formula (S4), at least one of $R_1$ to $R_5$ is —OR', and at least one of $R_{15}$ to $R_{19}$ is —OR". In further specific embodiments of Formula (S4), only one of $R_1$ to $R_5$ is —OR', and only one of $R_{15}$ to $R_{19}$ is —OR". The —OR' and —OR" groups are usually located symmetrically. In particular embodiments, the —OR' and —OR" groups are located at $R_1$ and $R_{19}$.

In more specific embodiments of Formula (S4), R' and R" are chelating ligands, and the heteroatom of the chelating ligand is present as a carbonyl group. In other embodiments, the chelating ligand is an alkylcarbonyl, —CO—R, —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, —(CH$_2$)$_n$—[O—(CH$_2$)$_k$]$_m$—OR, or salts thereof; wherein k, m, and n are independently integers from 0 to 10 and k+m+n≥1 (i.e. greater than or equal to 1); R, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic; and Z is sulfur or oxygen. Specific examples of such chelating ligands include —CH$_2$—CO—OCH$_3$ and —CO—CH$_3$. It is believed that chelating ligands incorporating sulfur atoms may lead to selectivity towards Hg(II) ions. It should be noted that R' and R" are usually the same.

In particular embodiments, all of $R_2$-$R_{18}$ are hydrogen. In some other embodiments, $R_{10}$ is alkyl, and $R_2$-$R_9$ and $R_{11}$-$R_{18}$ are hydrogen.

Also falling within the scope of formula (S4) are symmetric compounds of formula (S4-I):

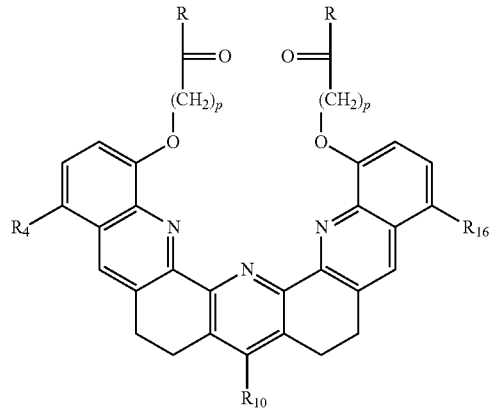

(S4-I)

wherein p is an integer from 0 to 4; R is hydrogen, hydroxyl or a salt thereof, alkyl, substituted alkyl, alkoxy, or substituted alkoxy; $R_{10}$ is alkyl; and $R_4$ and $R_{16}$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group.

One specific derivative of the scaffold compound (S4) is that of formula (L4):

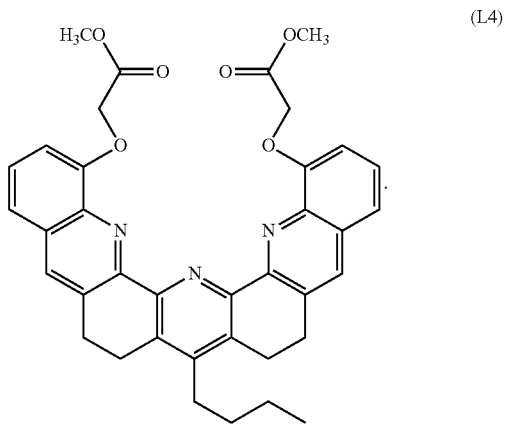 [SMILES: CCCCc1c2c(nc3c1CCc1cc4cccc(OCC(=O)OC)c4nc1-3)-c1nc3c(OCC(=O)OC)cccc3cc1CC2]

(L4)

Compound (L4) is also known as 8-butyl-1,15-bis (methoxycarbonylmethoxy)-diquinolino[2,3-c:3',2'-h]-6,7,9,10-tetrahydroacridine. This is a heptadentate compound.

Macrocyclic compounds of Formula (S4) and polymers using the compounds of Formula (S4) as a monomer are also contemplated. In the macrocyclic compounds, a linking moiety connects the two oxygen atoms of the —OR' and the —OR" groups together. Macrocyclic compounds of Formula (S4) may have the general structure of Formula (S4-M):

Formula (S4-M)

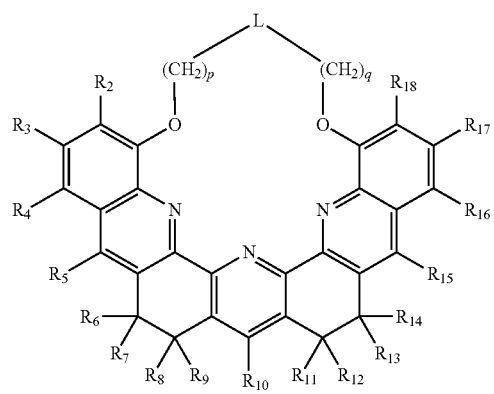

wherein $R_2$-$R_{18}$ are as defined above, p and q are independently integers from 1 to 10;

and L is a linking group. Again, the linking group can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino. Those linking groups illustrated in Formulas (M1)-(M7) can also apply here.

In the polymers, the monomers are linked through the oxygen atoms, or through the carbon atoms on the phenyl rings. Specific examples of polymers are illustrated below as Formulas (P21)-(P26). For simplicity, the —OR' and —OR" groups are illustrated as being located at $R_1$ and $R_{19}$, though they can generally be located as described above.

Formula (P21)

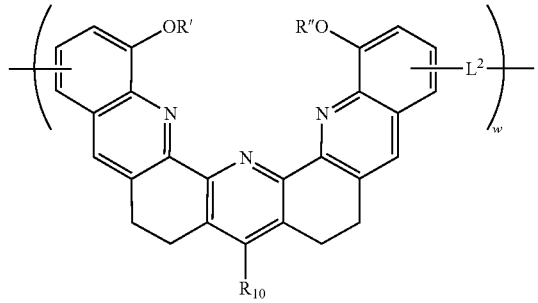

Formula (P22)

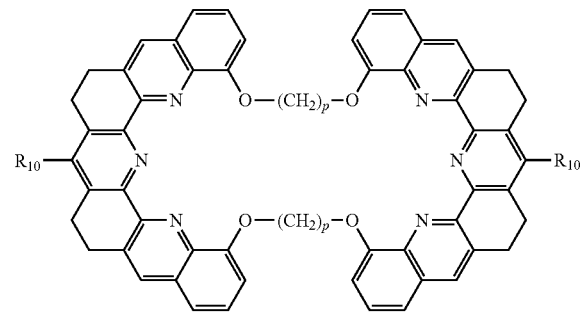

Formula (P23)

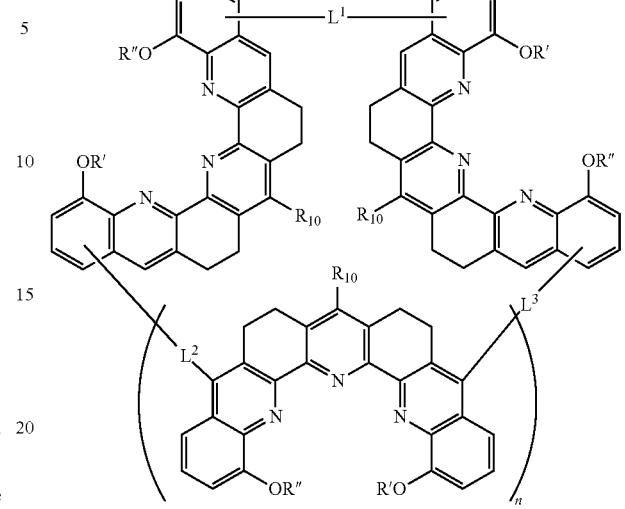

Formula (P24)

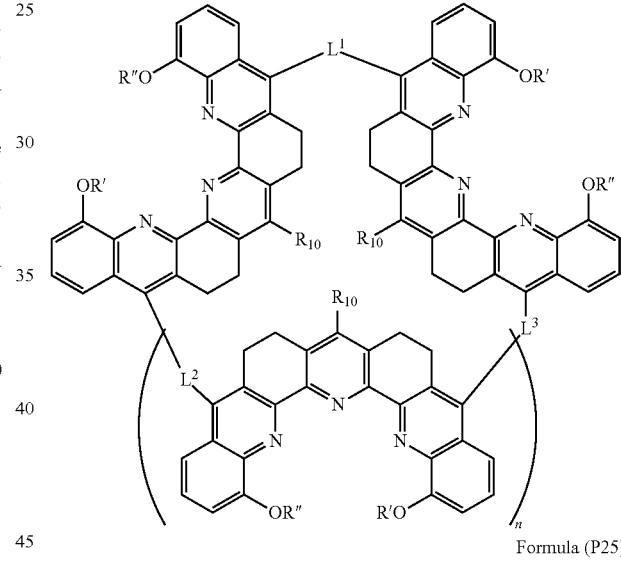

Formula (P25)

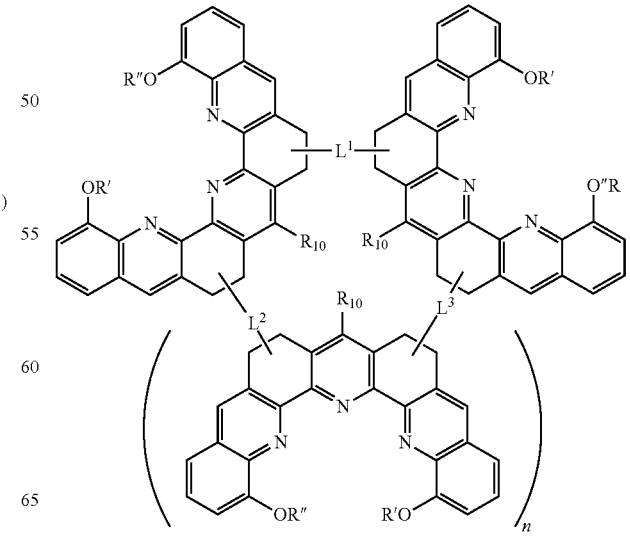

Formula (P26)

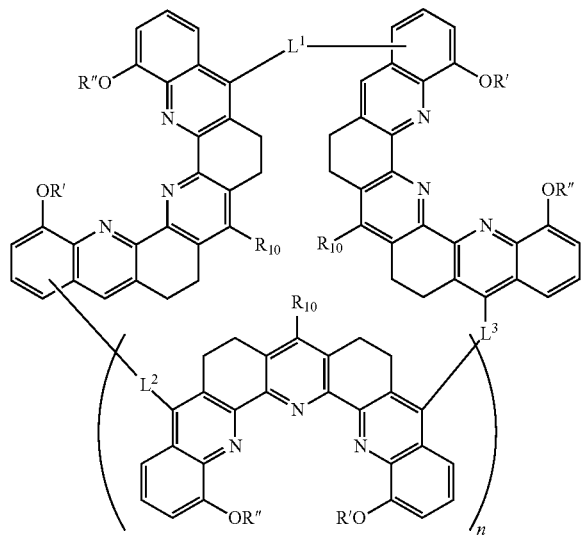

wherein $L^1$, $L^2$, and $L^3$ are independently linking groups; each $R_9$ is independently hydrogen or alkyl; R' and R" are independently a chelating ligand comprising at least one linking group and at least one heteroatom; and n is the degree of polymerization, and is from 0 to about 100. In (P21), w is the degree of polymerization, and is from 2 to about 100. Again, the linking groups can be made from any suitable combination of atoms, including alkyl, substituted alkyl, aryl, substituted aryl, heteroaryl, substituted heteroaryl, heterocyclic, substituted heterocyclic, alkenyl, substituted alkenyl, alkynyl, substituted alkynyl, polyether, and amino. For example, the linking groups could be alkyl. It is noted that the polymers can be homopolymers or copolymers (i.e. two or more different monomers).

For clarity, it is noted that in (P23)-(P26), $L^2$ is within the repeating unit, while $L^3$ is outside the repeating unit. It should be noted that in (P23), (P25), and (P26), the linkages $L^1$, $L^2$, and $L^3$ can be through any of the carbon atoms on the given ring, depending on the identity of the linkage. It should be noted that in (P23)-(P26), depending on the location of the linkages and the number of repeating units, the various portions of the cyclic polymer can rotate so that the R' and R" groups are directed to the interior or the exterior of the cyclic polymer, whichever is more stable.

Figure 8:
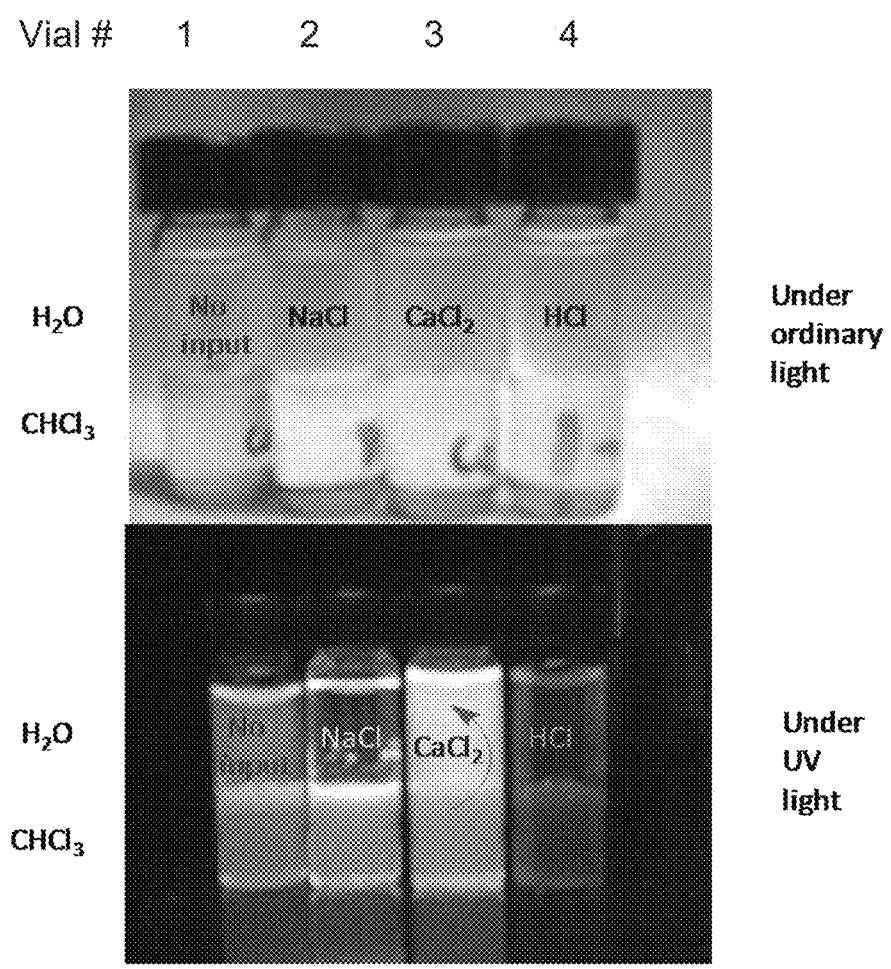
FIG. 8 is a set of pictures showing the fluorescent properties of compound L4 in two different solvents (water and chloroform) in the presence of different metal ions o and acid (NaCl, $CaCl_2$), HCl) under ordinary light and under UV light (365 nm). The concentration of L4 was 0.00032 M. Vial #2 used aqueous sodium chloride, Vial #3 included aqueous calcium chloride, and Vial #4 included dilute hydrochloric acid.

FIG. 8 is a set of pictures showing the fluorescent properties of compound L4 in two different solvents (water and chloroform) under ordinary light and under UV light (365 nm). Vial #1 contains only L4, Vial #2 contains sodium chloride, Vial #3 contains calcium chloride, and Vial #4 contains hydrochloric acid. The two layers in each vial were mixed, then allowed to separate and observed. In Vial #1, L4 is present in the chloroform layer. There is no reaction to sodium in Vial #2. In Vial #3, L4 exhibits an intense blue fluorescent response to $Ca^{2+}$. In addition, the complex in Vial #3 migrated to the water layer. It is believed that this migration will only occur with a metal ion of the proper size and sufficiently high ionic charge. Vial #4 exhibited a green fluorescence. Interference from acid is, therefore, not expected to cause false positive results.

Manufacture of Scaffold S4

The compounds of Formula (S4) can be made using a Friedlander condensation involving a 1,2,3,6,7,8-hexahydroacridine-4,5-dione and at least one o-aminobenzaldehyde (depending on whether the compound is symmetric or asymmetric). Synthesis Scheme 3 illustrates a two-step reaction to produce a compound of Formula (S4) using two aminobenzaldehydes (AA1) and (AA3) and a hexahydroacridine-4,5-dione (S4a). Again, the aminobenzaldehydes (AA1) and (AA3) could be the same, in which case the reaction would be a one-step reaction using two moles of the aminobenzaldehyde per mole of hexahydroacridine-4,5-dione. For simplicity, the —OR' and —OR" groups are illustrated below at the $R_1$ and $R_{19}$ positions.

Synthetic Scheme 3:

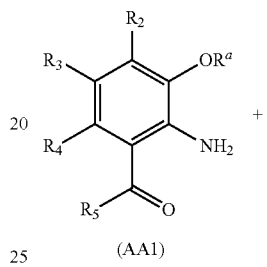

(AA1)

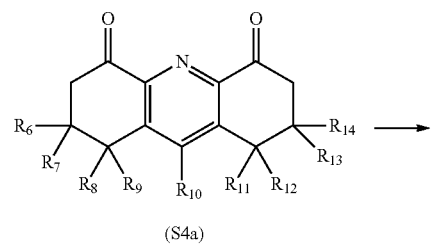

(S4a)

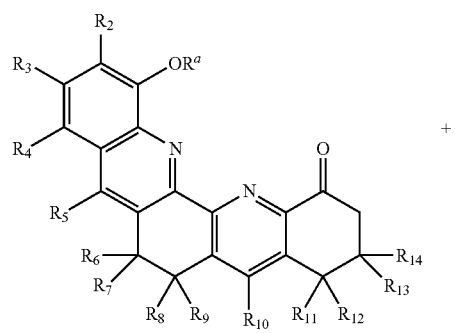

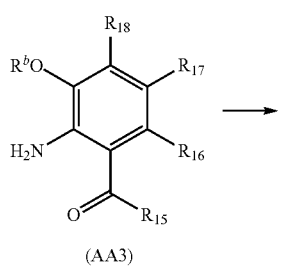

(AA3)

49

-continued

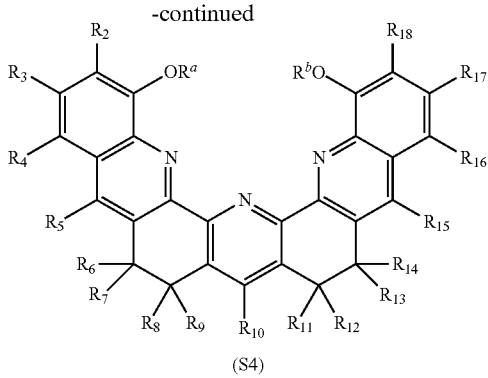

(S4)

The reaction typically occurs in the presence of a base and an alcohol, e.g. potassium hydroxide (KOH) and ethanol (EtOH). Once the aminobenzaldehyde is consumed, trifluoroacetic acid is added to precipitate the compound out of solution. The reaction also works when carried out in toluene using methanol and potassium hydroxide, but a fully aromatized product (i.e. the cyclohexane rings become aromatic) is generated as an impurity. The use of this dehydrating reagent is important in the synthesis of the compound.

The substituents $R^a$ and $R^b$ can be the final desired ligands, or can be intermediate ligands that are substituted to obtain the final desired ligands R' and R", whether to form the compounds, or to obtain macrocyclic compounds or linkers to obtain polymers. The compound containing $R^a$ and $R^b$ can be reduced with hydrobromic acid to obtain —OH groups, and then be reacted with reactants of the formula $L^a$-R' and $L^b$-R", wherein $L^a$ and $L^b$ are leaving groups known in the art, to obtain the final desired ligands.

Scaffold (S5)

Many compounds disclosed herein can be used as an MRI contrast agent when bound to suitable metal ions such as Gd(III), Fe(III), Co(III), Mn(II), Cu(II), or Ni(II). Some derivatives can permit the chelation of two water molecules to Gd(III), which is twice as many as in current commercial products. This is expected to lead to either increased resolution or to a reduced dose of the contrast agent.

Suitable scaffolds for MRI contrast agents include scaffold compound (S5), which has two quinoline units and has the following formula:

Formula (S5)

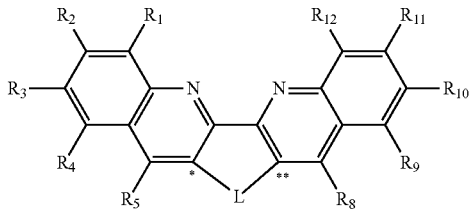

wherein $R_1$, $R_2$, $R_3$, $R_4$, $R_5$, $R_8$, $R_9$, $R_{10}$, $R_{11}$, and $R_{12}$ are independently selected from hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

50 wherein at least one of $R_1$ to $R_5$ is —OR', —SR', —COR', or —NR'$_2$;

at least one of $R_8$ to $R_{12}$ is —OR", —SR", —COR", or —NR"$_2$; and wherein R' and R" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom, or together form a linking moiety that contains at least one heteroatom, so that the compound is a macrocyclic compound;

and wherein L is a bridge having a backbone length of 1, 2, 3, or 4; and the backbone comprises methylene, amino, sulfur, or oxygen; and with the proviso that no four of $R_1$, $R_2$, $R_3$, $R_4$, $R_5$, $R_8$, $R_9$, $R_{10}$, $R_{11}$, and $R_{12}$ and any methylene groups in the bridge L are alkoxy.

The term "backbone" refers to the shortest series of covalently bonded atoms that runs between the two carbon atoms identified with asterisks (*), (**) in Formula (S5), with the backbone length being measured by the number of atoms running directly between the two carbon atoms in that shortest series of covalently bonded atoms. For purposes of clarity, the backbone will not contain any double bonds.

For purposes of Formula (S5), the term "methylene" refers to a radical of the formula —CR$^1$R$^2$—, wherein R$^1$ and R$^2$ are independently hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group.

For purposes of Formula (S5), the term "amino" refers to a radical of the formula —NR$^1$R$^2$ and also to a radical of the formula —NR'—, where R$^1$ and R$^2$ are independently hydrogen, alkyl, substituted alkyl, aryl, or substituted aryl.

The proviso that no four of $R_1$, $R_2$, $R_3$, $R_4$, $R_5$, $R_8$, $R_9$, $R_{10}$, $R_{11}$, and $R_{12}$ and any methylene groups in the bridge L are alkoxy means that there can be a maximum of three alkoxy substituents directly attached to the scaffold.

With respect to the bridge L of the fifth scaffold compound (S5), please note that (S5) encompasses scaffold compounds (S1), and does not encompass (S2). The scaffold of Formula (S1) is an example where the bridge L has a backbone length of two (2) atoms. The scaffold of Formula (S5-a) is an example where the bridge L has a backbone length of one (1) atom, and the scaffold of Formula (S5-b) is an example where the bridge L has a backbone length of three (3) atoms, as illustrated below:

Formula (S5-a)

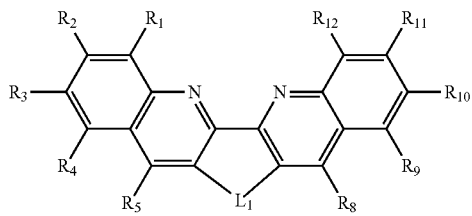

Formula (S5-b)

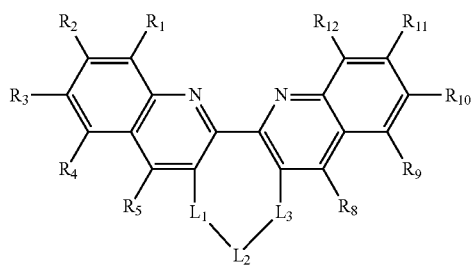

wherein $R_1$, $R_2$, $R_3$, $R_4$, $R_5$, $R_8$, $R_9$, $R_{10}$, $R_{11}$, and $R_{12}$ are as described above in Formula (S5); and $L_1$, $L_2$, and $L_3$ are independently methylene, amino, sulfur, or oxygen.

Examples of bridges that are contemplated for Formula (S5-b) include —$CH_2$—O—$CH_2$—; —$CH_2$—S—$CH_2$—; —O—$CH_2$—O—; —O—$CH_2$—$CH_2$—O—; and —NR—$CH_2$—NR—.

In specific embodiments of Formula (S5), only one of $R_1$ to $R_5$ is —OR', and only one of $R_8$ to $R_{12}$ is —OR". The —OR' and —OR" groups are usually located symmetrically. In particular embodiments, the —OR' and —OR" groups are located at $R_1$ and $R_{12}$.

In more specific embodiments of Formula (S5), R' and R" are chelating ligands, and the heteroatom of the chelating ligand is present as a carbonyl group. Suitable chelating ligands are discussed above with respect to Formula (S1).

In some narrower embodiments of Formula (S5), $R_4$ and $R_9$ are the same, and are not hydrogen or alkoxy. In particular embodiments, $R_2$, $R_3$, $R_5$, $R_6$, $R_8$, $R_{10}$, and $R_{11}$ are hydrogen, while $R_4$ and $R_9$ are the same and are not hydrogen or alkoxy.

The —OR', —SR', —COR', —NR'$_2$, —OR", —SR", —COR", or —NR"$_2$ groups (also referred to as "arms") are usually located at $R_1$ and $R_{12}$ in the compounds of Formula (S5). The arms should have a negative charge somewhere, and preferably near the chelating core. Formulas (D2) and (D3), previously described, are examples of good scaffolds for MRI contrast agents. More generally, the arms should have a chelating ligand that contains an anionic charge. Examples of groups that can provide such an anionic charge include generally any group including an O⁻ charge, such as pyridine-N-oxide or anionic phenol; a group including a carboxyl group, such as hydroxypyridinone or phenol or a phenol derivative; phosphate ($PO_4$); imide; nitrate ($NO_3$); pyridinone or piperidinone; and oxazole. Some examples of compounds that are derivatives of (S5) are illustrated below:

Formula (S5-A)

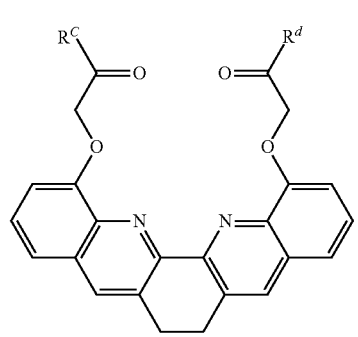

Formula (S5-B)

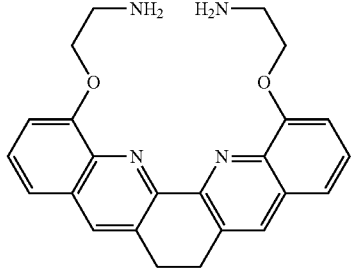

Formula (S5-C)

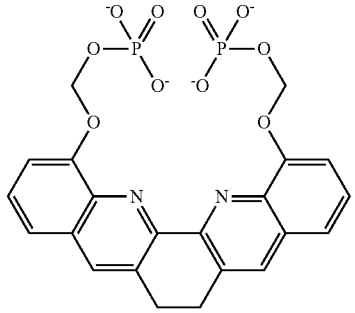

Formula (S5-D)

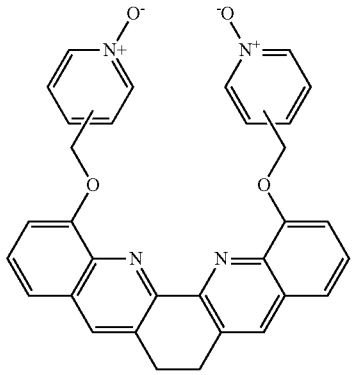

Formula (S5-E)

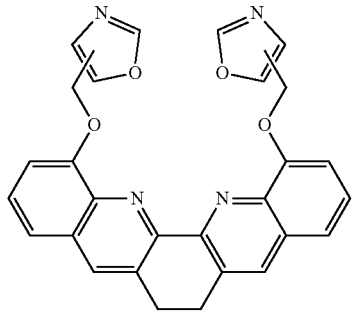

Formula (S5-F)

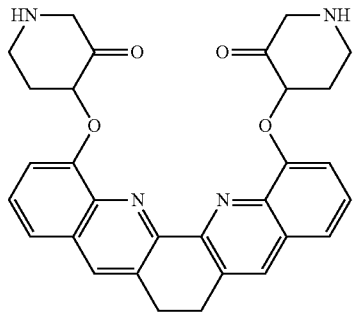

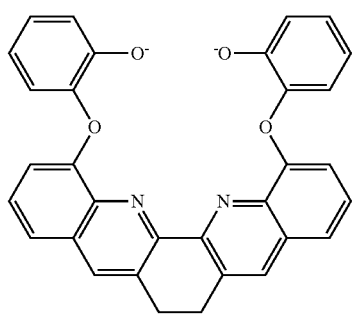

Formula (S5-G)

In Formula (S5-A), $R^c$ and $R^d$ can be alkoxy or amino (i.e. to form a carboxy or amide group). Formula (S5-B) is an example where the chelating ligand ends in an amino group. Formula (S5-C) is an example where the chelating ligand ends in a phosphate group. Formula (S5-D) is an example where the chelating ligand ends in a pyridine-N-oxide group. Formula (S5-E) is an example where the chelating ligand ends in an oxazole group. Formula (S5-F) is an example where the chelating ligand ends in a pyridinone group. Formula (S5-G) is an example where the chelating ligand ends in an anionic phenol group.

The compounds of Formula (S5) can also be used to bind metal ions in solution. Selectivity towards certain metal ions can be tailored by appropriate selection of sulfur, oxygen, and nitrogen atoms in the chelating arms. For example, chelating arms containing sulfur will favor binding to mercury (Hg) ions. It is particularly contemplated that when binding of metal ions is desired, that in Formula (S5), two of $R_1$ to $R_5$ are —OR', —SR', —COR', or —NR'$_2$ groups; and two of $R_8$ to $R_{12}$ are —OR", —SR", —COR", or —NR"$_2$ groups.

It should be noted that one or both of the nitrogen atoms of the scaffold of Formula (S5) may be oxidized. An example of such an oxidized compound is illustrated in Formula (S5-H):

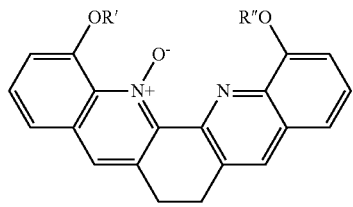

Formula (S5-H)

Macrocyclic compounds of Formula (S5) and polymers using the compounds of Formula (S5) as a monomer are also contemplated.

Manufacture of Scaffold S5

Figure 18:
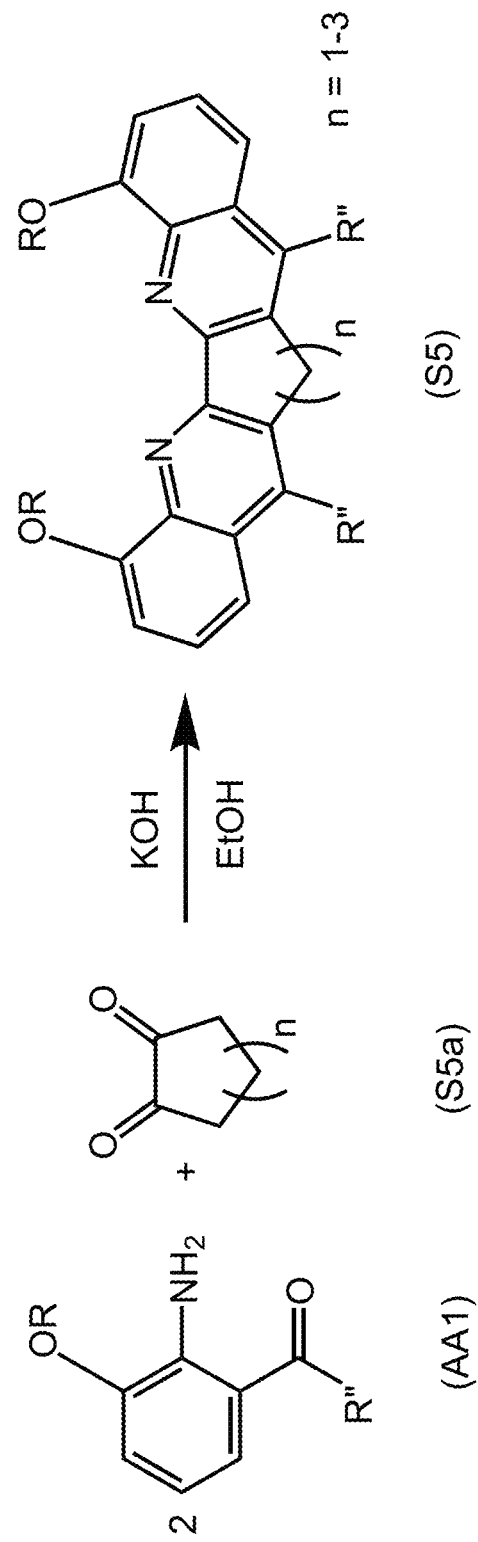
FIG. 18 shows a chemical synthesis scheme for preparing the scaffold compound of Formula (S5).

The compounds of Formula (S5) can generally be made as described above with respect to the compounds of Formula (S1). FIG. 18 shows a general synthesis scheme for compounds of Formula (S5). An o-aminobenzaldehyde (AA1) is reacted with a diketone (S5a) to produce the compound of Formula (S5). The reaction occurs in the presence of a base and an alcohol, e.g. potassium hydroxide (KOH) and ethanol (EtOH). Once the aminobenzaldehyde is consumed, trifluoroacetic acid (TFA) is added to dehydrate and/or precipitate the compound out of solution. The use of this dehydrating reagent is important in the synthesis of the compound.

Figure 19:
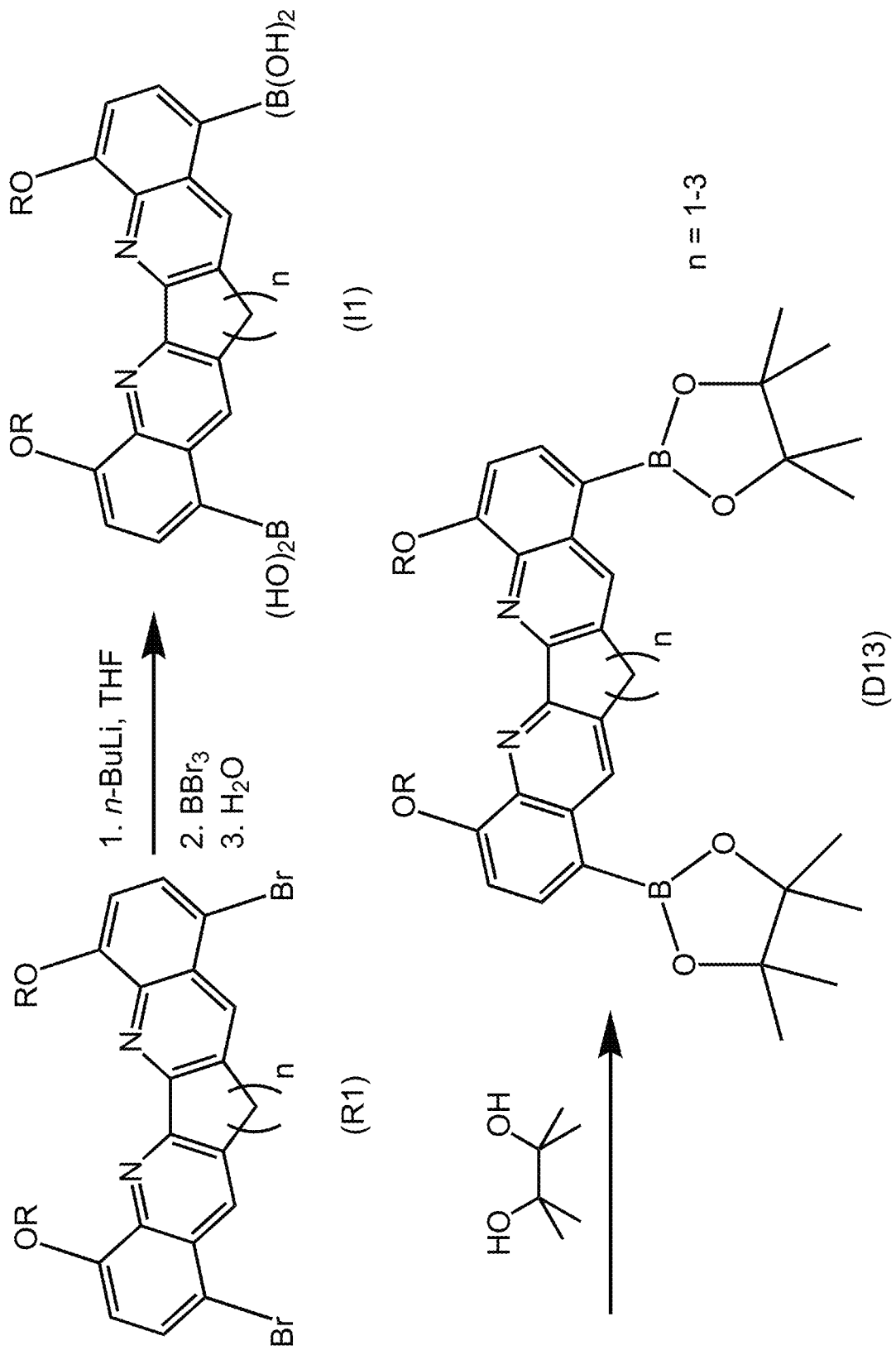
FIG. 19 shows a chemical synthesis scheme for preparing compounds of Formula (D13).

FIG. 19 shows a synthesis scheme for compound (D13), which includes two pinacolatoboron groups. The starting reactant ($R_1$) includes two bromide groups. Borylation is performed using n-butyl lithium in THF, boron tribromide, and water to obtain —B(OH)$_2$ groups in place of the bromide groups on the intermediate (11). The —B(OH)$_2$ groups are then reacted with pinacol to obtain the pinacolatoboron groups on the final compound (D13). In this figure n=1, 2, or 3.

Scaffold (S6)

Also contemplated is scaffold compound (S6), which is similar to scaffolds (S1) and (S5), but includes one or two additional rings at the end(s) of the compound, and does not have chelating arms. Scaffold compound (S6) has the following formula:

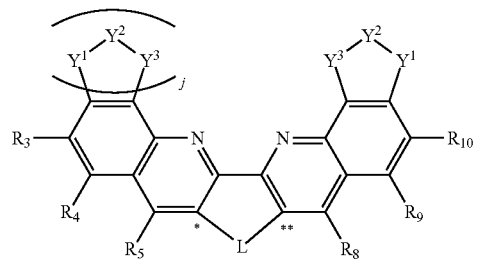

Formula (S6)

wherein $R_3$, $R_4$, $R_5$, $R_8$, $R_9$, and $R_{10}$ are independently selected from hydrogen, alkoxy, substituted alkoxy, aryloxy, substituted aryloxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

j is either 0 or 1;

$Y^1$, $Y^2$, and $Y^3$ are independently —O—, —NR'—, —BR$^2$—, —S—, —(CO)—, —(PO)—, —(PO$_2$)—, or alkylene or substituted alkylene having 1 to 3 carbon atoms, or combinations thereof, wherein $R^1$ is hydrogen, alkyl, substituted alkyl, aryl, or substituted aryl, and wherein $R^2$ is hydrogen, hydroxyl, alkyl, substituted alkyl, or halogen; and wherein L is a bridge having a backbone length of 1, 2, 3 or 4; and the backbone comprises methylene, amino, sulfur, or oxygen.

The term "backbone" refers to the shortest series of covalently bonded atoms that runs between the two carbon atoms identified with asterisks (*), (**) in Formula (S6), with the backbone length being measured by the number of atoms running directly between the two carbon atoms in that shortest series of covalently bonded atoms. For purposes of clarity, the backbone will not contain any double bonds.

For purposes of Formula (S6), the term "methylene" refers to a radical of the formula —CR$^1$R$^2$—, wherein $R^1$ and $R^2$ are independently hydrogen, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, or a water-solubilizing group.

For purposes of Formula (S6), the term "amino" refers to a radical of the formula —NR$^1$R$^2$ and also to a radical of the formula —NR'—, where R$^1$ and R$^2$ are independently hydrogen, alkyl, substituted alkyl, aryl, or substituted aryl.

In addition, when j is zero, the two carbon atoms should be treated as having R$_1$ and R$_2$ (as in scaffold S5), which can be selected from the same groups as R$_3$. Also, Y', Y$^2$, and Y$^3$ are always present, or in other words the end ring is a minimum of a five-membered ring, and can also be a six-membered ring, or larger. In addition, it is contemplated that the -Y$^1$-Y$^2$-Y$^3$- bridge may contain double bonds. Again, it should be noted that one or both of the nitrogen atoms of the scaffold of Formula (S6) may be oxidized.

Examples of -Y$^1$-Y$^2$-Y$^3$- bridges that are contemplated for Formula (S6) include —CH$_2$—O—CH$_2$—; —CH$_2$—S—CH$_2$—; —O—CH$_2$—O—; —O—CH$_2$—CH$_2$—O—; and —NR$^1$—CH$_2$—NR$^1$—.

Additional examples of -Y$^1$-Y$^2$-Y$^3$- bridges that contain oxygen include: —CH$_2$—CH$_2$—CH$_2$—O—; —CH$_2$—CH$_2$—(CO)—O—; —(CO)—CH$_2$—CH$_2$—O—; —(CO)—CH$_2$—(CO)—O—; —(CO)—NR$^1$—CH$_2$—O—; —(CO)—NR$^1$—(CO)—O—; —(CO)—NR'—CH$_2$—O—; —CH$_2$—CH=CH—O—; —CH=CH—CH$_2$—O—; —O—CH=CH—O—; —NR$^1$—(CO)—CH$_2$—O—; —CH$_2$—CH$_2$—O—; —CH$_2$—(CO)—O—; —(CO)—CH$_2$—O—; —NR$^1$—(CO)—O—; and —O—CH$_2$—O—.

Additional examples of -Y$^1$-Y$^2$-Y$^3$- bridges that contain nitrogen include: —CH$_2$—CH$_2$—CH$_2$—NR$^1$—; —CH$_2$—CH$_2$—(CO)—NR$^1$—; —(CO)—CH$_2$—CH$_2$—NR$^1$—; —(CO)—CH$_2$—(CO)—NR$^1$—; —(CO)—NR$^1$—CH$_2$—NR$^1$—; —(CO)—NR$^1$—(CO)—NR$^1$—; —(CO)—NR$^1$—CH$_2$—NR$^1$—; —CH$_2$—CH=CH—NR$^1$—; —CH=CH—CH$_2$—NR$^1$—; —O—CH=CH—NR$^1$—; —NR$^1$—(CO)—CH$_2$—NR$^1$—; —CH$_2$—CH$_2$—NR$^1$—; —CH$_2$—(CO)—NR$^1$—; —(CO)—CH$_2$—NR$^1$—; —NR$^1$—(CO)—NR$^1$—; —NR$^1$—CH$_2$—NR$^1$—; —NR$^1$—CH$_2$—O—; and —O—CH$_2$—NR$^1$—

Additional examples of -Y$^1$-Y$^2$-Y$^3$- bridges that contain sulfur include: —CH$_2$—CH$_2$—CH$_2$—S—; —CH$_2$—CH$_2$—(CO)—S—; —(CO)—CH$_2$—CH$_2$—S—; —(CO)—CH$_2$—(CO)—S—; —(CO)—NR$^1$—CH$_2$—S—; —(CO)—NR$^1$—(CO)—S—; —(CO)—NR$^1$—CH$_2$—S—; —CH$_2$—CH=CH—S—; —CH=CH—CH$_2$—S—; —O—CH=CH—S—; —NR$^1$—(CO)—CH$_2$—S—; —(CO)—O—CH$_2$—S—; —(CO)—S—CH$_2$—S—; —(CO)—NR$^1$—CH$_2$—S—; —CH$_2$—CH$_2$—S—; —CH$_2$—(C)—S—; —(CO)—CH$_2$—S—; —NR$_1$—(CO)—S—; —O—(CO)—S—; —S—(CO)—S—; —S—CH$_2$—S—; —NR$_1$—CH$_2$—S—; —O—CH$_2$—S—; and —S—CH$_2$—O—.

Additional examples of -Y$^1$-Y$^2$-Y$^3$- bridges that contain boron include: —CH$_2$—CH$_2$—CH$_2$—B(OH)—; —CH$_2$—CH$_2$—B(OH)—; —CH$_2$—CH$_2$—BF—; and —CH$_2$—CH$_2$—CH$_2$—BF—; —CH$_2$—O—B(OH)—O—; —CH$_2$—O—B(OH)—; —O—B(OH)—O—; —CH$_2$—O—(PO$_2$)—O—; and —O—(PO)—O—.

A particular derivative of the scaffold compound (S6) is that of formula (S6-a):

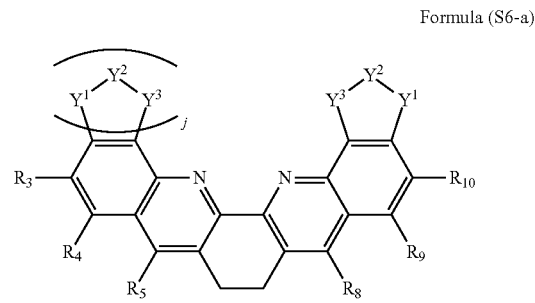

Formula (S6-a)

wherein R$_3$, R$_4$, R$_5$, R$_8$, R$_9$, and R$_{10}$ are as described above in Formula (S6). In particular embodiments, R$_3$, R$_4$, R$_5$, R$_8$, R$_9$, and R$_{10}$ are all hydrogen.

Specific derivatives of the scaffold compound (S6) include those of formulas (S6-A)-(S6-J):

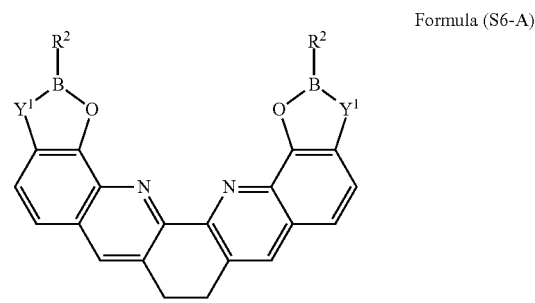

Formula (S6-A)

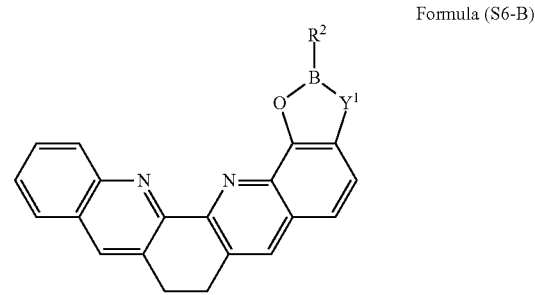

Formula (S6-B)

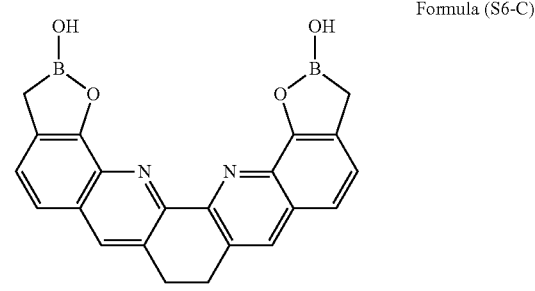

Formula (S6-C)

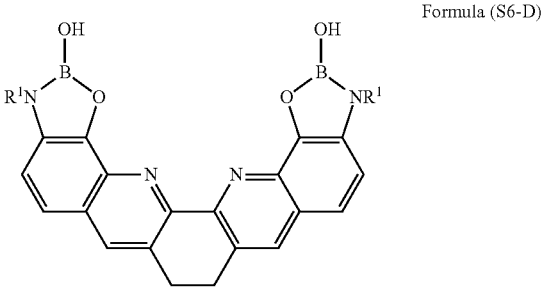

Formula (S6-D)

-continued

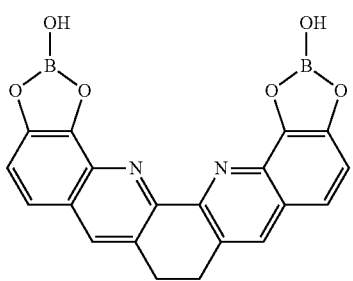
Formula (S6-E)

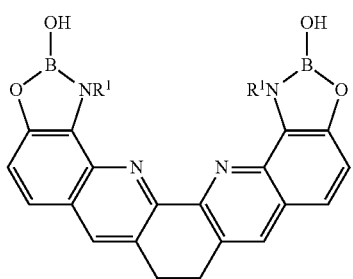
Formula (S6-F)

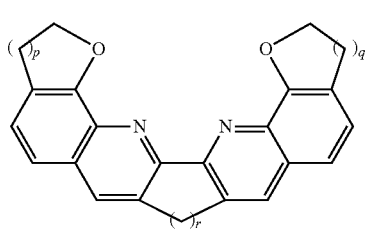
Formula (S6-G)

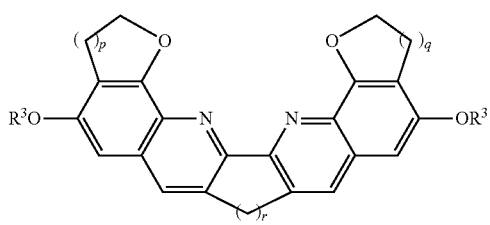
Formula (S6-H)

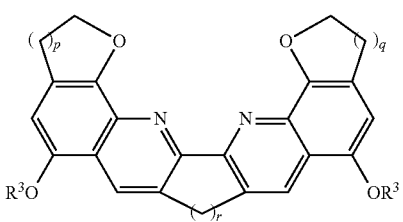
Formula (S6-I)

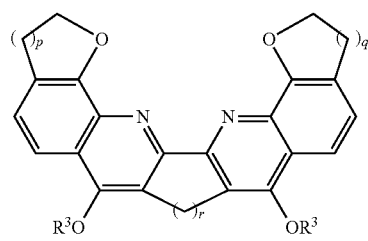
Formula (S6-J)

wherein $Y^1$, $R^1$, and $R^2$ are as defined above for Formula (S6); p, q, and r are independently integers from 1 to 3; and $R^3$ is hydrogen, alkyl, substituted alkyl, aryl, or substituted aryl.

Manufacture of Scaffold S6

Figure 20:
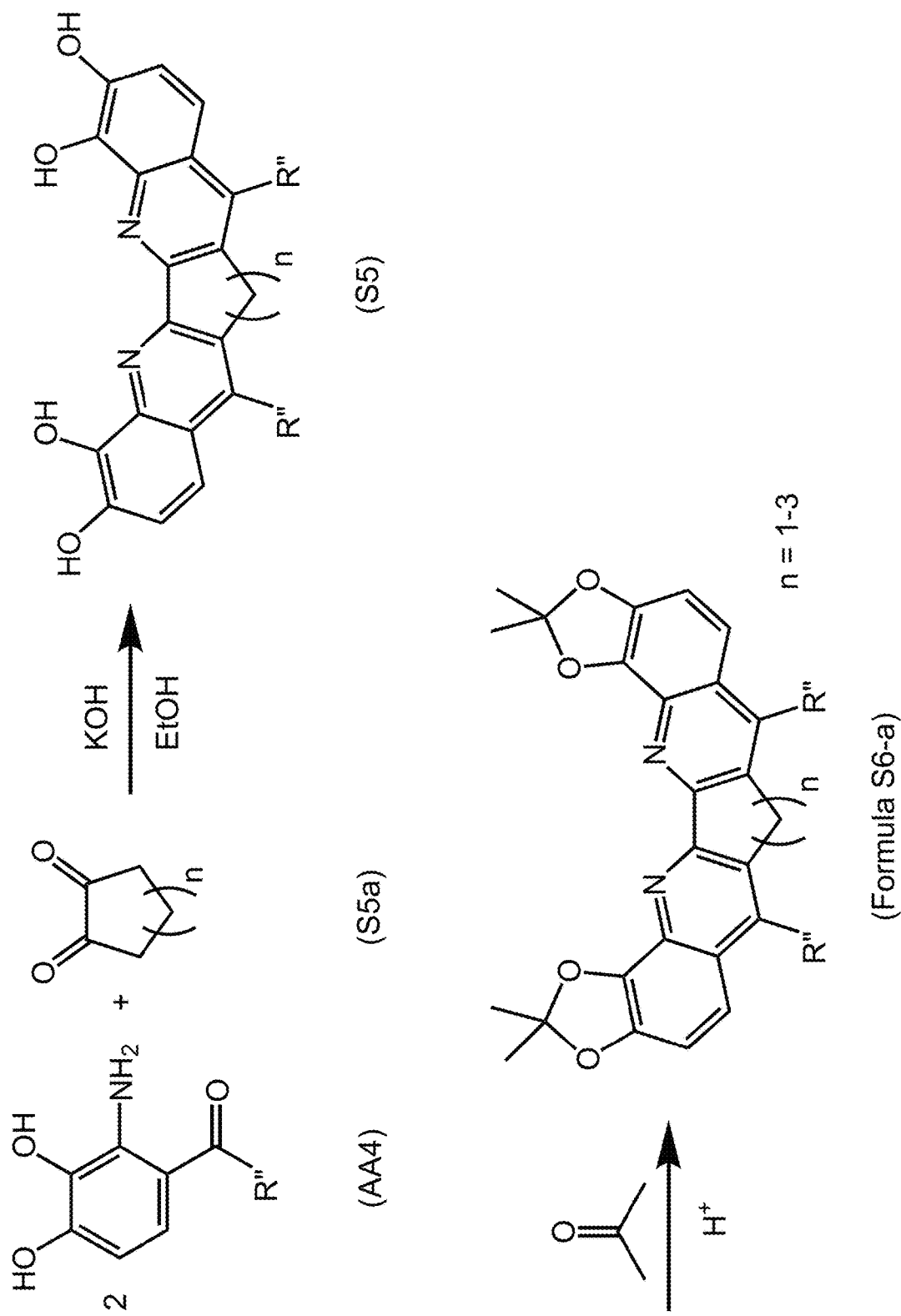
FIG. 20 shows a chemical synthesis scheme for preparing compounds of Formula (S6).

The compounds of Formula (S6) can be made according to the example synthesis scheme illustrated in FIG. 20. A dihydroxy-o-aminobenzaldehyde (for compounds of Formula (S5). An o-aminobenzaldehyde (AA4) is reacted with a diketone (S5a) to produce an intermediate compound (12) that also falls within the scope of Formula (S5). The reaction occurs in the presence of a base and an alcohol, e.g. potassium hydroxide (KOH) and ethanol (EtOH). Next, the intermediate (12) is reacted with acetone in an acidic solution to obtain a compound of Formula (S6-a), where $Y^1=Y^3$=oxygen, and $Y^2$ is a —C(CH$_3$)$_2$— group, i.e. substituted methylene. The reaction typically occurs in the presence of a base and an alcohol, e.g. potassium hydroxide (KOH) and ethanol (EtOH). It is possible that trifluoroacetic acid is useful for precipitating the compound out of solution.

Scaffold (S7)

Also contemplated is scaffold compound (S7), which is similar to scaffold (S1), but has a cyclohexene ring in the center instead of a cyclohexane ring. Scaffold compound (S7) has the following formula:

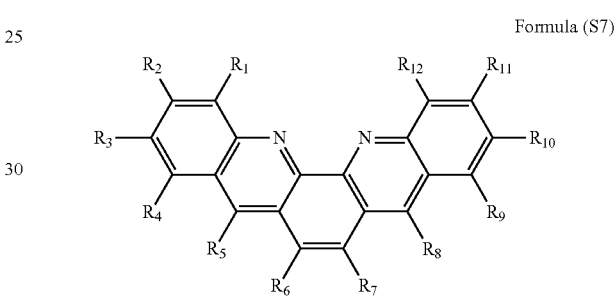
Formula (S7)

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group;

wherein at least one of $R_1$ to $R_6$ is —OR', —SR', —COR', or —NR'$_2$;

wherein at least one of $R_7$ to $R_{12}$ is —OR", —SR", —COR", or —NR"$_2$; and wherein R' and R" are independently selected from hydrogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, or a chelating ligand comprising at least one linking group and at least one heteroatom, or together form a linking moiety that contains at least one heteroatom, so that the compound is a macrocyclic compound.

In particular embodiments of Formula (S7), the compound is symmetrical. In specific embodiments of Formula (S7), one of $R_1$ to $R_6$ is —OR', and one of $R_7$ to $R_{12}$ is —OR". The —OR' and —OR" groups are usually located symmetrically. In particular embodiments, the —OR' and —OR" groups are located at $R_1$ and $R_{12}$.

In more specific embodiments of Formula (S7), R' and R" are chelating ligands, and the heteroatom of the chelating ligand is present as a carbonyl group. The chelating ligand is selected from those described above with respect to Formula (S1). It should be noted that R' and R" are usually the same.

In some narrow embodiments of Formula (S7), the $R_1$-$R_{12}$ groups cannot be alkoxy. Of course, one of $R_1$ to $R_6$ is —OR', —SR', —COR', or —NR'$_2$; and one of $R_7$ to $R_{12}$ is —OR", —SR", —COR", or —NR"$_2$, as previously described.

In some narrower embodiments of Formula (S7), $R_4$ and $R_9$ are the same, and are not hydrogen. In additional embodiments, $R_4$ and $R_9$ are not hydrogen or alkoxy. For example, in particular embodiments, $R_4$ and $R_9$ are halogen, aryl, substituted aryl, alkynyl, or substituted alkynyl. In particular embodiments, $R_2$, $R_3$, $R_5$, $R_6$, $R_8$, $R_{10}$, and $R_{11}$ are hydrogen, while $R_4$ and $R_9$ are the same and are not hydrogen.

In additional specific embodiments of Formula (S7), the —OR', —SR', —COR', —NR'$_2$, —OR", —SR", —COR", or —NR"$_2$ groups are located at $R_1$ and $R_{12}$. In these embodiments, $R_4$ and $R_9$ are the same, and are not hydrogen or a water-solubilizing group. Put another way, $R_4$ and $R_9$ are independently selected from halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, and sulfide.

Manufacture of Scaffold S7

Figure 21:
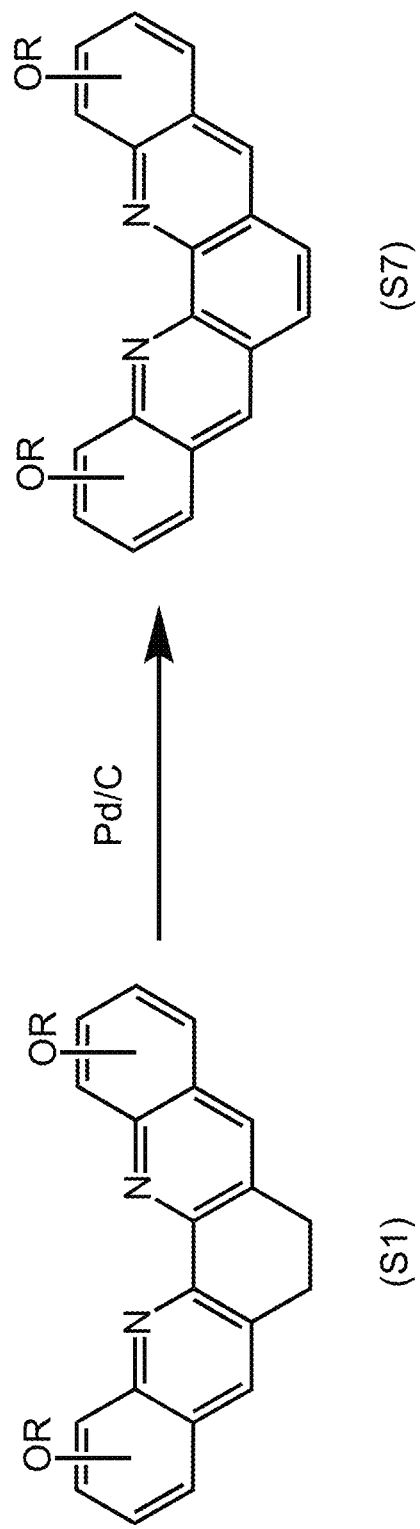
FIG. 21 shows a chemical synthesis scheme for preparing compounds of Formula (S7).

The compounds of Formula (S7) can be made according to the example synthesis scheme illustrated in FIG. 21. The reactant, which is a compound of Formula (S1), is dehydrogenated, for example using palladium on carbon, to obtain the compound of Formula (S7).

Referring again to all compounds of the present disclosure, these compounds luminesce ratiometrically, i.e. they emit light at one wavelength (i.e. color) in the absence of metal ions and at a different wavelength/color in the presence of certain metal ions, the different wavelength depending on the identity of the metal ion. In a compound that luminesces ratiometrically, the addition of a metal ion results in a simultaneous decrease in the size of the original fluorescent band of the free compound and the appearance of a new band at a different wavelength. The size of the new luminescent band increases with increasing concentration of the metal ion at the expense of the original band, which eventually disappears. This type of behavior provides an internal reference point against which to measure optical changes, which is desirable. In contrast, other molecules typically act only as on/off sensors—their luminescence is either triggered or quenched when metal ions are present. It is noted that with certain other metal ions, an on-off behavior is observed with the compounds of the present disclosure. Complexes with lanthanides such as Eu(III) may be used to sensitize the luminescence of the metal ion.

Appropriate substitutions can also lead to increased water solubility for the present compounds, which is useful in practical applications. No structural changes to the scaffolds are needed to change the solubility of these molecules.

The incorporation of chiral groups may lead to chiral catalysts for asymmetric synthesis. It is also contemplated that the optical properties and luminescent quantum yield of the compounds can also be tuned by substitution on the phenolic rings of the scaffolds.

The compounds of the present disclosure can be immobilized on polymer surfaces or embedded into a polymer matrix for final applications without any modification of the scaffold, as linkers can be attached through the hydroxy groups or any of the rings. Immobilization is a useful feature, and typically requires major modifications in the synthetic protocol of conventional receptors. Some of the scaffolds of the present disclosure already have a protocol for permitting immobilization, which facilitates final applications.

Metal complexes can be formed between the scaffold compounds (S1)-(S7) and one or more metal ions. A metal complex is generally formed by combining or contacting a scaffold compound with a metal ion. This can be done in aqueous solution or slurry, i.e. a solution/slurry containing the metal ion is added to a solution/slurry containing the scaffold compound, or vice versa. The metal ion can be provided in the form of a metal salt or a metal acid. Alternatively, a solid form of the scaffold compound (e.g. powder) can be mixed into a solution containing the metal ion, or vice versa. Another method would be to expose the scaffold compound to acid vapors. Still another method is to mix a solid form of the scaffold compound with a solid form of the metal ion or metal acid. The resulting metal complex can be in the form of a coordination complex or an acid-base complex (for example when chelating ligands are protonated), each formed between the scaffold compound and the metal ion.

The following examples are provided to illustrate various aspects of the compounds of the present disclosure. The examples are merely illustrative and are not intended to limit the disclosure to the materials, conditions, or process parameters set forth therein.

EXAMPLES

General

NMR spectra was acquired using Bruker DPX-250, Bruker Avance DMX-600, or Bruker Avance DRX-800 spectrometers. Solvents used were CDCl$_3$ with 0.05% TMS, DMSO-d$_6$, or CF$_3$COOD. All chemical shifts (δ) were reported in ppm units relative to trimethylsilane (TMS) internal reference ($\delta_{TMS}$=0, $^1$H), CDCl$_3$ (δ 77.23, $^{13}$C), DMSO-d$_6$ (δ 2.54, $^1$H; 40.45, $^{13}$C), or TFA (δ 11.5, $^1$H; 162.4, $^{13}$C). The assignment of carbon atoms was done by means of an attached proton test (APT) experiment. Melting points were measured in open glass capillary tubes on a Mel-Temp apparatus and are uncorrected. Infrared spectra (IR) were obtained on a Spectrum RXI Perkin Elmer FT-IR spectrometer and the frequencies reported in wavenumbers (cm$^{-1}$). High resolution MS was performed using a sodium iodide matrix.

Example 1

8,8'-Dimethoxy-3,3'-dimethylene-2,2'-biquinoline (D1) was prepared according to the following scheme:

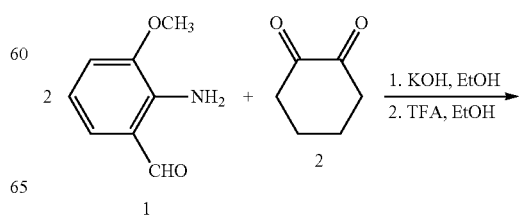

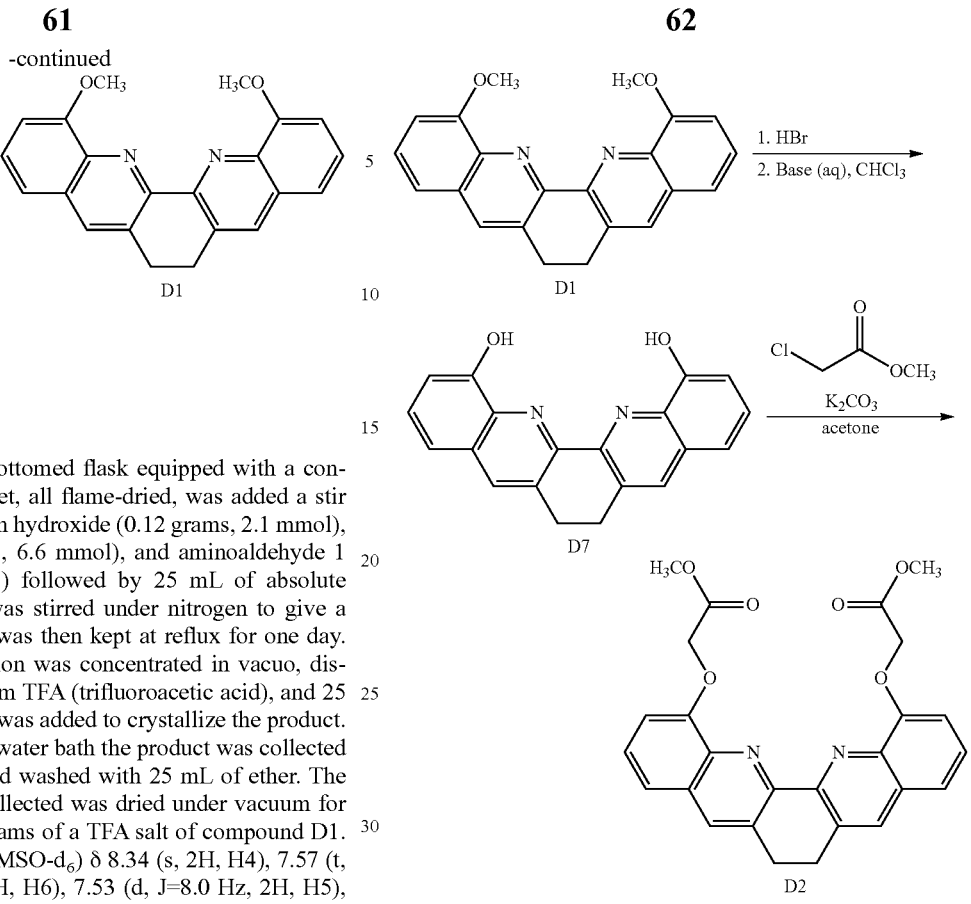

To a 50 mL round-bottomed flask equipped with a condenser and nitrogen inlet, all flame-dried, was added a stir bar, powdered potassium hydroxide (0.12 grams, 2.1 mmol), diketone 2 (0.74 grams, 6.6 mmol), and aminoaldehyde 1 (1.97 grams, 13 mmol) followed by 25 mL of absolute ethanol. The mixture was stirred under nitrogen to give a yellow solution which was then kept at reflux for one day. The resulting red solution was concentrated in vacuo, dissolved in 25 mL of warm TFA (trifluoroacetic acid), and 25 mL of absolute ethanol was added to crystallize the product. After cooling in an ice-water bath the product was collected by vacuum filtration and washed with 25 mL of ether. The red powder that was collected was dried under vacuum for one day to give 2.17 grams of a TFA salt of compound D1. $^1$H NMR (800 MHz, DMSO-$d_6$) δ 8.34 (s, 2H, H4), 7.57 (t, J=7.2 Hz, J'=8.0 Hz, 2H, H6), 7.53 (d, J=8.0 Hz, 2H, H5), 7.19 (d, J=7.2 Hz, 2H, H7), 3.97 (s, 6H, 2xOCH$_3$), 3.19 (s, 4H, 2xCH$_2$).

The red powder was dissolved in 250 mL of chloroform and washed with 0.03M aqueous tris(hydroxymethyl)aminomethane (2×45 mL, 1×20 mL) and brine (50 mL). After drying the organic layer over magnesium sulfate and after drying agent and solvent removal (rotavap), and overnight drying under reduced pressure, 1.97 grams (87%) of neutral compound D1 was collected. Crystals of D1 were obtained by recrystallization from ethyl acetate and hexane and after storing the solution near 2° C. for 2 days. Compound D1 crystallized as brown prismatic crystals, mp. 209.4-209.8° C. after dehydration of solvent molecules at 108.8-114.0° C. $^1$H NMR (600 MHz, CDCl$_3$) δ 3.23 (s, 4H, CH$_2$), 4.13 (s, 6H, OCH$_3$), 7.00 (d, J=7.7 Hz, 2H, H3), 7.34 (d, J=8.1 Hz, 2H, H5), 7.46 (t, J=7.7 Hz, 2H, H4), 8.00 (s, 2H, H6). $^{13}$C NMR (150 MHz, CDCl$_3$) δ 156.5 (C), 151.6 (C), 140.5 (C), 134.6 (CH), 133.5 (C), 129.7 (C), 127.8 (CH), 118.9 (CH), 107.3 (CH), 77.36 (CHCl$_3$), 56.0 (OCH$_3$), 28.9 (ArCH$_2$). IR (KBr) 3435.8 (OH, s), 2942.3 (s), 2840.1 (s), 1629.8 (s), 1554.8 (s), 1490.6 (s), 1466.4 (s), 1381.8 (s), 1353.1 (s), 1266.4 (s), 1173.6 (s), 1154.1 (s), 1092.2 (s), 1024.0 (s), 916.1 (m), 765.0 (s), 738.6 (s), 714.6 (s). HRMS M+Na$^+$ (abundance/ppm); calculated for [C$_{22}$H$_{18}$N$_2$NaO$_2$]$^+$: 365.1266; measured: 365.1255 (3.0).

Example 2

8,8'-Bis(methoxycarbonylmethoxy)-3,3'-dimethylene-2,2'-biquinoline (D2) was prepared using two different methods, both of which proceeded according to the following scheme:

First, 8,8'-dihydroxy-3,3'-dimethylene-2,2'-biquinoline (D7) was prepared by the reduction of compound D1. A solution of 01 (0.40 grams, 1.2 mmol) in 25 mL of 48% aqueous hydrobromic acid was kept in reflux for 28.5 hours. The resulting mixture was then allowed to cool down to room temperature overnight and the precipitate collected by vacuum filtration. After washing it with 5 mL of water, it was dried under vacuum overnight to give 0.32 grams of a bright orange-red powder. $^1$H NMR (800 MHz, DMSO-$d_6$) δ 11.26 (br s, 2H, OH), 8.72 (s, 2H, H5), 7.69 (t, J=7.7 Hz, 2 h, H3), 7.59 (d, J=7.9 Hz, 2H, H4), 7.35 (d, J=7.4 Hz, 2H, H2, H2), 3.39 (s, 4H, CH$_2$). This sample was dissolved in 55 mL of methanol and 190 mL of chloroform and washed with 0.07 M aqueous tris(hydroxymethyl)aminomethane (2×75 mL), dried over magnesium sulfate, filtered, the solvent removed using a rotavap, and the residue dried under vacuum overnight. This afforded 0.26 grams (71%) of product D7 as a yellow solid. The compound can be recrystallized from a small volume of chloroform. This gives the product as shiny greenish-yellow needles, mp. 294-297° C. $^1$H NMR (600 MHz, CDCl$_3$) δ 3.28 (s, 4H, CH$_2$), 7.14 (dd, J=8.1 Hz, J'=0.8 Hz, 2H, H3), 7.30 (d, J=8.1 Hz, 2H, H5), 7.45 (t, J=7.8 Hz, 2H, H4), 8.06 (s, 2H, H6). $^{13}$C NMR (150 MHz, CDCl$_3$) δ 153.7 (C), 150.1 (C), 138.5 (C), 135.3 (CH), 133.4 (C), 129.3 (C), 129.1 (CH), 117.5 (CH), 110.9 (CH), 77.36 (CHCl$_3$), 28.8 (ArCH$_2$). IR (KBr) 3448.3 (s), 3307.5 (s), 1607.2 (m), 1561.1 (m), 1494.1 (s), 1466.0 (s), 1333.4 (s), 1313.5 (s), 1211.2 (s), 1151.0 (s), 759.6 (s), 538.5 (m). HRMS M+Na$^+$ (abundance/ppm); calculated for [C$_{20}$D$_{74}$N$_2$NaO$_2$]$^+$: 337.0953; measured: 337.0948 (1.5).

From D7, two methods were used to obtain D2.

Method 1. Crude scaffold D7 (0.15 grams, 0.48 mmol), cesium carbonate (0.16 grams, 0.48 mmol), and methyl chloroacetate (0.11 grams, 1.0 mmol) were stirred under nitrogen at room temperature in 25 mL of anhydrous DMF for 2 days. During this period, additional drops of methyl chloroacetate were added until scaffold D7 was no longer detected by TLC (silica gel, MeCN:NH₄OH, 9:1, v/v). The mixture was then vacuum filtered, the precipitate washed with a few milliliters of a solution of hexane/chloroform (9:1), and the filtrate concentrated in vacuo. This gave crude compound D2 as a black solid (quantitative yield). $^1$H NMR (600 MHz, TFA-d) δ 9.11 (s, 2H, H5), 7.97 (t, J=8.2 Hz, J'=8.0 Hz, 2H, H3), 7.92 (d, J=8.3 Hz, 2H, H4), 7.57 (d, J=7.7 Hz, 2H, H2), 5.26 (s, 4H, CH₂), 3.93 (s, 6H, OCH₃), 3.62 (s, 4H, ArCH₂). HRMS, M+Na⁺ (abundance/ppm); calculated for [C₂₆H₂₂N₂NaO₆]⁺: 481.1376; measured: 481.1374 (0.42).

Method 2. Compound D7.HBr (4.25 grams, 10.8 mmol), methyl chloroacetate (2.62 grams, 23.9 mmol), and potassium carbonate (1.78 grams, 12.9 mmol) were stirred at room temperature in 450 mL of acetone for one day. After this, additional methyl chloroacetate (1.12 grams, 10.2 mmol) and potassium carbonate (2.76 grams, 20.0 mmol) were added over 3 days while following the reaction by TLC. Insoluble material was removed by gravity filtration and the light orange filtrate (which also exhibits intense blue fluorescence, $\lambda_{ex}$=365 nm) was concentrated in vacuo. The residue was briefly boiled in fresh acetone and filtered to collect a powder which was dried under vacuum. This afforded 0.52 grams (11%) of D2 as a tan powder. Additional material (1.48 grams) of lower purity may be obtained from the filtrate. $^1$H NMR (600 MHz, DMSO-d₆) δ 8.25 (s, 2H, H5), 7.54 (d, J=8.1 Hz, 2H, H4), 7.50 (t, J=8.8 Hz, 2H, H3), 7.07 (d, J=7.4 Hz, 2H, H2), 4.99 (s, 4H, OCH₂), 3.69 (s, 6H, OCH₃), 3.11 (s, 4H, ArCH₂). $^{13}$C NMR (150 MHz, DMSO-d₆) δ 169.3 (C=O), 153.0 (C), 150.4 (C), 138.5 (C), 135.0 (CH), 133.2 (C), 129.2 (C), 127.6 (CH), 120.0 (CH), 109.5 (CH), 65.1 (CH₂), 52.0 (OCH₃), 27.1 (ArCH₂). IR (KBr) 3360 (m), 2949 (m), 1751 (s), 1606 (m), 1441 (s), 1241 (s), 1111 (s), 760 (s).

Example 3

Crude compound D2 (0.10 grams, 0.22 mmol) was dissolved in 11 mL of methanol, and then lithium hydroxide (0.12 grams, 2.9 mmol) was added and stirred at room temperature for four days. The resulting mixture was vacuum filtered on a Hirsh funnel and washed with cold methanol. This gave 58 mg of Li₂.D3 as a yellow powder. $^1$H NMR (600 MHz, DMSO) δ 8.41 (s, 2H, H5), 7.55-7.65 (m, 4H, H3, H4), 7.28 (br m, 2H, H2), 4.7-4.9 (br m, 4H, OCH₂), 3.33 (s, 4H, CH₂).

Example 4

8,8'-Dimethoxy-2,2'-biquinoline (B3) was prepared according to the following scheme:

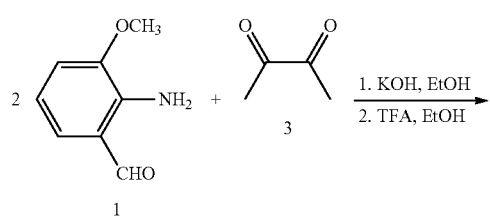

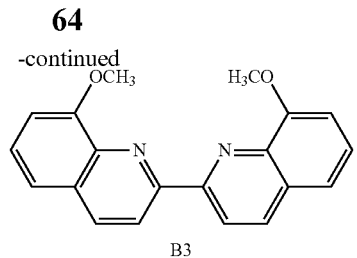

Aminobenzaldehyde 1 (1.51 grams, 10.0 mmol), 2,3-butadione 3 (0.43 grams, 4.96 mmol), and potassium hydroxide (0.59 grams, 11 mmol) were refluxed in 36 mL of absolute ethanol for six days, adding more 3 (0.43 grams, 4.9 mmol) in short increments during this time. The solution was allowed to cool to room temperature and 4 mL of TFA was added under strong stirring, then the solution was stored at −12° C. for two days. Next, the precipitated product was collected by vacuum filtration and washed consecutively with ice-cold ethanol and ether. After drying, a TFA salt of compound B3 (1.61 g, 39%) was obtained as brown, shiny flakes. $^1$H NMR (600 MHz, DMSO-d₆) δ 8.77 (d, J=Hz, 2H), 8.51 (d, J=Hz, 2H), 7.58 (m, 4H), 7.28 (m, 2H), 4.06 (s, 6H).

Example 5

5,5'-Dibromo-8,8'-dimethoxy-3,3'-dimethylene-2,2'-biquinoline (D4) was prepared according to the following scheme:

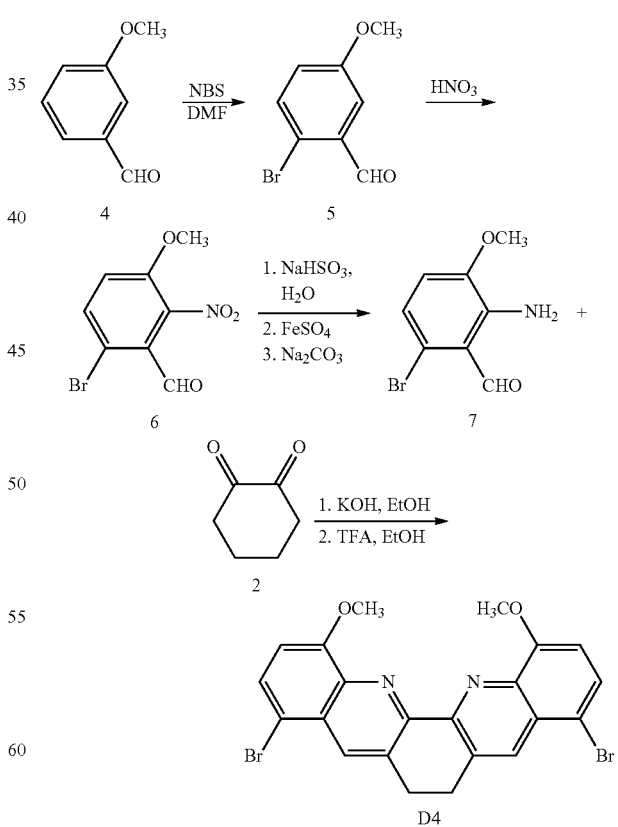

First, 6-bromo-3-methoxybenzaldehyde (5) was prepared. m-Anisaldehyde (20.03 grams, 0.15 mol), NBS (28.92 grams, 0.16 mol) and 200 mL of anhydrous DMF were stirred for 22 hours at room temperature under nitrogen in a flame-dried round-bottomed flask. The resulting orange solution was carefully poured into 1.5 L of water, being vigorously stirred, in order to precipitate the product. The mixture was stirred for an additional 15 minutes, vacuum filtered, washed with water, and dried under vacuum. This gave 26.00 grams (82%) of compound 5 as a white powder. This product is completely pure by NMR spectroscopy and may be used in the next step, but it can be recrystallized in methyl ethyl ketone. After storing the solution at 0° C. for several days, the product crystallizes as white needles, mp 71.8-72.6° C. $^1$H NMR (600 MHz, CDCl$_3$) δ 3.84 (s, 3H, OCH$_3$), 7.03 (dd, J=8.8 Hz, J'=3.2 Hz, 1H, H4), 7.41 (d, J=3.0 Hz, 1H, H2), 7.52 (d, J=8.8 Hz, 1H, H5), 10.31 (s, 1H, CHO). $^{13}$C NMR (150 MHz, CDCl$_3$) δ 55.9 (OCH$_3$), 112.7 (CH), 118.2 (C), 123.4 (CH), 134.0 (C), 134.7 (CH), 159.4 (C), 192.0 (C=O), IR (KBr, cm$^{-1}$) 2843 (m), 2746 (m), 1677 (s), 1598 (s), 1571 (s), 1474 (s), 1278 (s), 1243 (s), 1060 (s).

Next, 6-bromo-2-nitro-3-methoxybenzaldehyde (6) was prepared. The intermediate 5 (10.07 grams, 46.8 mmol) in powder form was added over 6 minutes to a solution of 70% nitric acid (50 mL) and concentrated sulfuric acid (20 mL) cooled in an ice water-bath to 0° C. with strong stirring. The yellow mixture was allowed to cool to 10° C. and then stirred at room temperature for an additional 29 minutes. The mixture was poured into 350 mL of ice-water, vacuum filtered, washed with ice-water (20 mL). The crude powder collected (9.34 grams, yellow powder) was recrystallized from toluene several times. This gave 8.24 grams (68%) of nitro derivative 6 as light yellow crystals, mp 164.2-165.2° C. $^1$H NMR (600 MHz, CDCl$_3$) δ 3.93 (s, 3H, OCH$_3$), 7.19 (d, J=9.0 Hz, 1H, H4), 7.74 (d, J=9.1 Hz, 1H, H5), 10.25 (s, 1H, CHO). $^{13}$C NMR (150 MHz, CDCl$_3$) δ 57.2 (OCH$_3$), 116.4 (C), 119.3 (CH), 125.3 (C), 136.2 (CH), 140.0 (C), 150.7 (C), 188.5 (C=O). IR (KBr) 2849 (w), 2768 (w), 1705 (s), 1593 (s), 1548 (s), 1466 (s), 1367 (s), 1228 (s), 1082 (s), 647 (s). HRMS, M+Na$^+$ (abundance/ppm); calculated for [C$_8$H$_6$BrNNaO$_4$]$^+$: 281.9378; measured: 281.9373 (1.8).

Then, 2-amino-6-bromo-3-methoxybenzaldehyde (7) was prepared. Crystals of compound 6 (2.2 grams, 8.6 mmol) were pulverized using a mortar and added to a 3-necked, 3-L round bottomed flask equipped with an Allihn condenser, a thermometer, and a mechanical stirrer. Next, sodium bisulfite (35.87 grams, 0.34 mol) was added followed by 1.5 L of water. The mixture was vigorously stirred and heated to boiling point using a Bunsen burner in order to obtain a solution (light yellow-green color). This solution was allowed to cool down to room temperature, iron(II)sulfate heptahydrate (20.1 grams, 72.3 mmol) was added, and the solution was stirred for 5 minutes until it all dissolved. The resulting orange solution was heated to boiling point over 26 minutes using a Bunsen burner, upon which it turned cloudy. The resulting mixture was allowed to cool down below boiling point (ca. 7 minutes) and then to it was carefully and slowly added 200 mL of saturated aqueous sodium bicarbonate through the condenser under vigorous stirring. The new mixture was heated to boiling point under a flame over 14 minutes, when it turned brown. The mixture was immediately vacuum filtered into a filter flask immersed in an ice-water bath. The iron hydroxide byproduct collected was dried under aspirator pressure and washed with ether (4×200 mL). Each of these fractions was subsequently used to extract the filtrate, which contains some crystallized product. The combined organic layers were dried over anhydrous sodium sulfate, gravity filtered, and the solvent removed in a rotavap. After drying under reduced pressure over drierite, 1.40 grams (71%) of product 7 was obtained as an orange powder, mp 73.8-74.4° C. $^1$H NMR (600 MHz, DMSO-d$_6$) δ 3.83 (s, 3H, OCH$_3$), 6.81 (d, J=8.4 Hz, 1H, H4), 6.89 (d, J=8.2 Hz, 1H, H5), 7.39 (br s, 2H, NH2, 10.19 (s, 1H, CHO). $^{13}$C NMR (150 MHz, CDCl$_3$) δ 56.0 (OCH$_3$), 113.8 (CH), 113.9 (C), 118.5 (C), 119.2 (CH), 143.8 (C), 146.7 (C), 195.6 (C=O). IR (KBr) 3419 (s), 3306 (s), 2872 (w), 2776 (w), 1648 (s), 1622 (s), 1579 (s), 1553 (s), 1459 (s), 1246 (s), 1052 (m), 664 (w). HRMS, M+H$^+$ (abundance/ppm); calculated for [C$_8$H$_9$BrNO$_2$]$^+$: 229.9817; measured: 229.9812 (2.2).

5,5'-Dibromo-8,8'-dimethoxy-3,3'-dimethylene-2,2'-biquinoline (D4) was then prepared. 1,2-Cyclohexadienone (0.12 grams, 1.1 mmol), 2-amino-6-bromo-3-methoxybenzaldehyde 7 (0.51 grams, 2.2 mmol), potassium hydroxide (0.032 grams, 0.6 mmol), and 25 mL of absolute ethanol were stirred under nitrogen in a flame dried round-bottomed flask equipped with a condenser until a yellow solution was obtained. This was kept in reflux for 25 hours. Part of the product precipitated and was collected by vacuum filtration to afford 0.30 grams of light olive green flakes. The filtrate was concentrated in vacuo and treated with 5 mL of TFA and then 15 L of ethanol to precipitate the product. After cooling and vacuum filtration, 0.17 grams of a bright red powder was obtained. Both product samples were combined, added 150 mL of chloroform and washed with a 0.03 M aqueous solution of tris(hydroxymethyl) aminomethane (2×45 mL), brine (45 mL), dried over magnesium sulfate, filtered, and the solvent removed in a rotavap. After drying under reduced pressure over drierite, 0.41 grams (76%) of a light yellow powder was collected. The compound is sufficiently pure for further reactions but if desired it can be recrystallized from chloroform and hexane and stored at 2° C. to induce crystallization. This gave 0.13 grams (25%) of compound D4 as yellow needles. $^1$H NMR (600 MHz, CDCl$_3$) δ 8.36 (s, 2H, H5), 7.72 (d, J=8.2 Hz, 2H, H3), 6.91 (d, J=8.3 Hz, 2H, H2), 4.13 (s, 3H, OCH$_3$), 3.32 (s, 4H, ArCH$_2$). $^{13}$C NMR (150 MHz, CDCl$_3$) δ 156.2 (C), 151.3 (C), 141.0 (C), 134.6 (C), 134.4 (CH), 131.1 (CH), 128.4 (C), 111.0 (C), 107.9 (CH), 56.0 (OCH$_3$), 28.6 (CH$_2$). IR (KBr) 3418.8 (s), 3306.4 (s), 1648.0 (s), 1578.7.5 (s), 1553.0 (s), 1245.9 (s), 1052.3 (m), 663.9 (w). HRMS, M+H$^+$ (abundance/ppm); calculated for [C$_{16}$H$_{22}$Br$_2$N$_2$NaO$_2$]$^+$: 520.9476; measured: 520.9490 (2.7).

Example 6

2,6-bis[8-(methoxycarbonylmethoxy)quinolin-2-yl]pyridine (1:1) was prepared according to the following scheme:

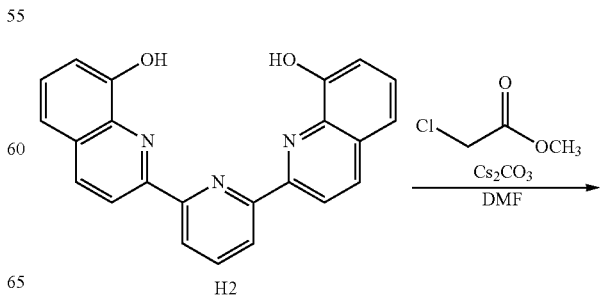

-continued

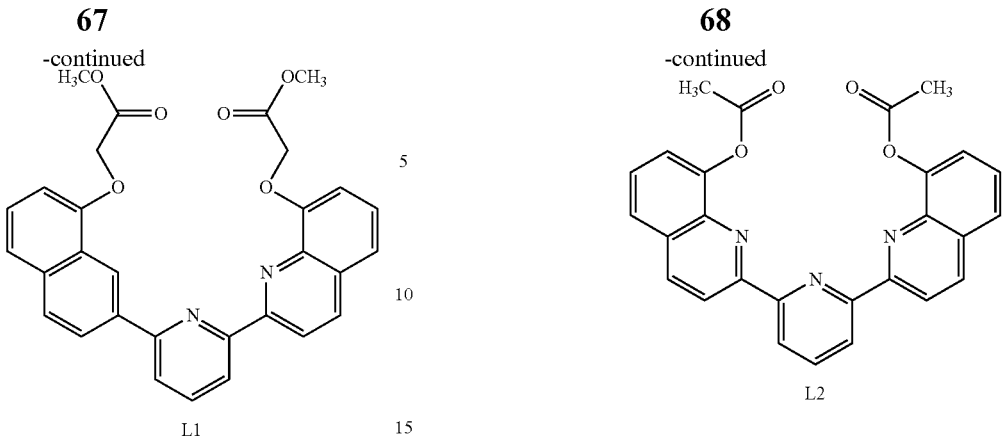

L1

L2

Scaffold H2 was prepared according to the literature. H2 is 2,6-bis[8-hydroxyquinolin-2-yl] pyridine.

Scaffold H2 (0.12 grams, 0.32 mmol), cesium carbonate (0.32 grams, 0.97 mmol), and methyl chloroacetate (77 milligrams, 0.71 mmol) were stirred at room temperature in 10 mL of anhydrous DMF for 2 days. The mixture was vacuum filtered, washed with DMF (2×3 mL), and the filtrate was concentrated in vacuo and dried under vacuum The crude light brown powder collected (0.17 grams) was heated to boiling point in 25 mL of toluene and gravity filtered to remove insoluble particles, which were washed with 5 mL of boiling toluene. The product crystallized as very pale orange-white short needles (81 mg, 50%) from the filtrate after it was stored at −2° C. for 3 days. A second crop (27 mg, 17%) of a tan powder was obtained after partial concentration of the filtrate to 10 mL and storing the solution at −11° C. for 2 days. $^1$H NMR (800 MHz, DMSO-d$_6$) δ 8.94 (d, J=8.5 Hz, 2H, H5), 8.76 (d, J=7.7 Hz, 2H, H7), 8.61 (d, J=8.5 Hz, 2H, H6), 8.31 (t, J=7.7 Hz, 1H, H8), 7.70 (d, J=8.0 Hz, 2H, H4), 7.59 (t, J=7.8 Hz, 2H, H3), 7.25 (d, J=7.7 Hz, 2H, H2), 5.21 (s, 4H, CH$_2$), 3.80 (s, 6H, OCH$_3$). $^1$H NMR (600 MHz, CDCl$_3$) δ 8.88 (d, J=8.5 Hz, 2H, H5), 8.80 (d, J=7.7 Hz, 2H, H7), 8.31 (d, J=8.5 Hz, 2H, H6), 8.06 (t, J=7.7 Hz, 1H, H8), 7.54 (d, J=8.1 Hz, 2H, H4), 7.46 (t, J=7.8 Hz, 2H, H3), 7.13 (d, J=7.5 Hz, 2H, H2), 5.09 (s, 4H, CH$_2$), 3.87 (s, 6H, OCH$_3$). $^{13}$C NMR (150 MHz, CDCl$_3$) δ 169.8 (C=O), 155.5 (2xC), 154.1 (C), 140.2 (C), 138.2 (CH), 137.0 (CH), 129.9 (C), 126.9 (CH), 122.6 (CH), 121.6 (CH), 119.8 (CH), 112.1 (CH), 67.4 (CH$_2$), 52.5 (CH$_3$). HRMS, M+Na$^+$ (abundance/ppm); calculated for [C$_{29}$H$_{23}$N$_3$NaO$_6$]$^+$: 532.1485; measured: 532.1459 (4.9).

Example 7

2,6-bis[8-(acetoxy)quinolin-2-yl]pyridine (L2) was prepared according to the following scheme:

Scaffold H2 (0.30 grams, 0.83 mmol), acetyl chloride (0.58 grams, 7.4 mmol), and pyridine (0.59 grams, 7.4 mmol) were stirred at room temperature in dichloromethane for 2 days. The solution was sequentially washed with 10% hydrochloric acid (3×70 mL), dilute aqueous sodium bicarbonate (3×70 mL), and brine (1×100 mL). After drying the sample over anhydrous sodium sulfate, solvent removal at a rotavap, and drying under reduced pressure for 2 days, 0.35 grams (94%) of a beige powder (L2) was obtained. Some X-ray quality crystals were obtained by dissolving a portion of the crude in a mixture of acetonitrile, methanol, and ethyl acetate and allowing it to evaporate slowly. The crystal structure is shown below. $^1$H NMR (600 MHz, CDCl$_3$) δ 8.87 (d, J=8.6 Hz, 2H, H5), 8.64 (d, J=7.8 Hz, 2H, H7), 8.35 (d, J=8.6 Hz, 2H, H6), 8.02 (t, J=7.8 Hz, 1H, H8), 7.78 (d, J=8.1 Hz, 2H, H4), 7.55 (t, J=7.7 Hz, J'=7.9 Hz, 2H, H3), 7.48 (d, J=7.4 Hz, 2H, H2), 2.62 (s, 6H, CH$_3$). $^{13}$C NMR (150 MHz, CDCl$_3$) δ 170.0 (C=O), 156.0 (C), 155.3 (C), 148.0 (C), 140.7 (C), 138.0 (CH), 137.1 (CH), 129.8 (C), 126.7 (CH), 126.0 (CH), 122.4 (CH), 121.7 (CH), 119.9 (CH), 21.3 (CH$_3$). HRMS, M+Na$^+$ (abundance/ppm), Calculated for [C$_{27}$H$_{19}$N$_3$NaO$_4$]$^+$: 472. 1273, measured: 472.1257 (3.4).

Example 8

2,6-bis[8-((2R)-2-trifluoromethyl-2-methoxy-2-phenylacetoxy)quinolin-2-yl] pyridine (L3) was prepared according to the following scheme:

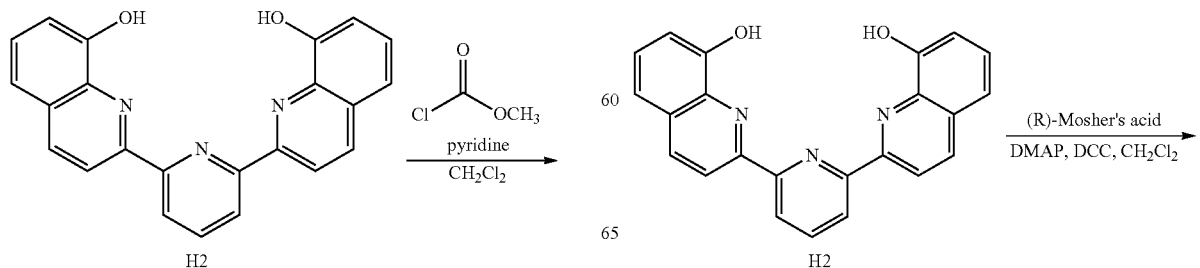

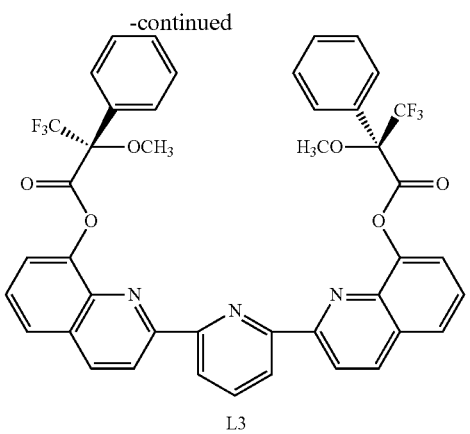

L3

Scaffold H2 (0.23 grams, 0.62 mmol), DMAP (4-dimethylaminopyridine) (14 milligrams, 0.11 mmol), and DCC (N,N'-Dicyclohexylcarbodiimide) (0.29 grams, 1.4 mmol) were added to 10 mL of dry dichloromethane and stirred at room temperature under nitrogen in a 3-necked round-bottomed flask equipped with a rubber stopper, glass stopper, and a condenser with a gas inlet attached. To this suspension was added (R)-Mosher's acid (α-methoxy-α-trifluoromethylphenylacetic acid) (0.33 grams, 1.4 mmol) in 3 mL of dichloromethane via syringe. The syringe was rinsed with dichloromethane (2×4 mL) and the suspension stirred at room temperature. After 3 days, 5 mL of dry chloroform was added. After an additional 4 days, the mixture was filtered, washed with dichloromethane (3×3 mL), and the filtrate was concentrated in vacuo, and dried under vacuum. The crude sample (0.63 grams) was treated with DMAP (13 mg, 0.11 mmol), DCC (0.11 grams, 0.53 mmol), (R)-Mosher's acid (0.10 grams, 0.43 mmol), and 15 mL of dry dichloromethane as before for 3 days. The suspension was vacuum filtered, washed with dichloromethane (3×5 mL). The filtrate was diluted with 40 mL of dichloromethane, washed with water (2×10 mL), dried over anhydrous sodium sulfate, gravity filtered, and concentrated. This crude product (0.76 grams) was recrystallized from 6 mL of toluene. This gave compound L3 as short, white needles (0.36 grams, 73%). $^1$H NMR (800 MHz, DMSO-$d_6$) δ 8.96 (d, J=8.6 Hz, 2H, H5 or H6), 8.78 (d, J=8.6 Hz, 2H, H6 or H5), 8.37 (d, J=7.6 Hz, 2H, H7), 8.17 (dd, J=7.2 Hz, J'=1.6 Hz, 2H), 8.08 (t, J=7.7 Hz, 1H, H8), 7.90 (d, J=7.5 Hz, 4H), 7.77-7.82 (m, 4H), 7.67-7.59 (m, 6H). $^1$H NMR (600 MHz, CDCl$_3$) δ 8.82 (d, J=8.6 Hz, 2H, H5 or H6), 8.37 (d, J=7.8 Hz, 2H, H7), 8.34 (d, J=8.6 Hz, 2H, H6 or H5), 7.97 (d, J=7.5 Hz, 4H, H9), 7.82 (d, J=8.1 Hz, 2H, H4), 7.70 (t, J=7.8 Hz, 1H, H8), 7.56 (t, J=7.7 Hz, J'=7.9 Hz, 2H, H3), 7.44-7.52 (m, 8H, H2, H10, H11), 3.92 (s, 6H, OCH$_3$). $^{13}$C NMR (150 MHz, CDCl$_3$) δ 165.4 (C=O), 156.7 (C), 155.3 (C), 147.0 (C), 140.5 (C), 137.8 (CH), 137.1 (CH), 132.1 (C), 130.1 (CH), 129.9 (C), 128.8 (CH), 128.2 (CH), 126.9 (CH), 126.5 (CH), 126.5 (CF$_3$), 124.6 (CF$_3$), 122.8 (CH), 122.7 (CF$_3$), 121.6 (CH), 120.8 (CF$_3$), 120.3 (CH), 85.7 (C—CF$_3$), 85.5 (C—CF$_3$), 85.3 (C—CF$_3$), 85.1 (C—CF$_3$), 56.2 (CH$_3$). HRMS, M+Na$^+$ (abundance/ppm), Calculated for [C$_{43}$H$_{29}$F$_6$N$_3$NaO$_6$]$^+$: 820.1858, Measured: 820.1824 (4.1).

Example 9

8-butyl-1,15-bis(methoxycarbonylmethoxy)-diquinolino[2,3-c:3',2'-h]-6,7,9,10-tetrahydroacridine (L4) was prepared according to the following scheme:

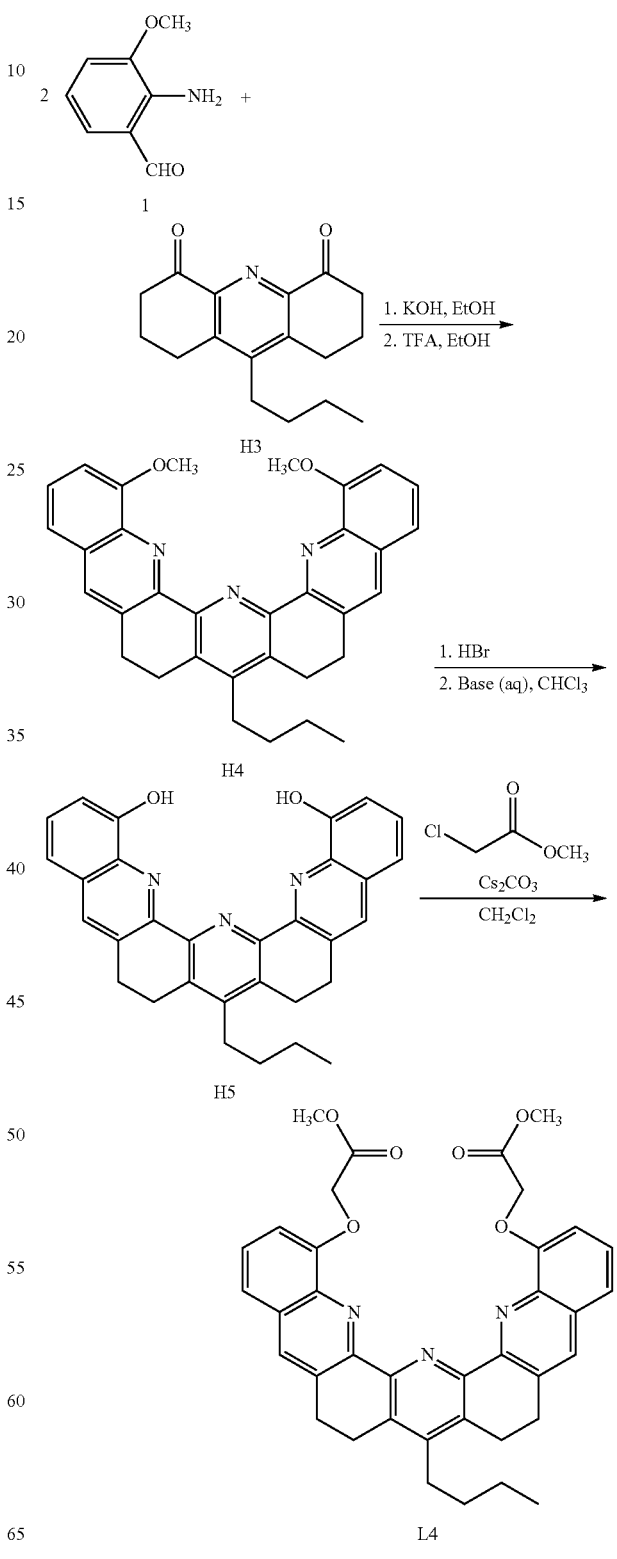

8-Butyl-1,15-dimethoxydiquinolino[2,3-c:3',2'-h]-6,7,9, 10-tetrahydroacridine (H4) was prepared. To a flame-dried 250 mL round bottomed flask equipped with a condenser, stir bar, and nitrogen gas inlet and containing a solution of potassium hydroxide (0.16 grams, 2.8 mmol) in 25 mL of absolute ethanol was added diketone H3 (1.87 grams, 6.9 mmol) dissolved in 10 mL of absolute ethanol followed by aminoaldehyde 1 in 10 mL of absolute ethanol. Reactant containers were rinsed with an additional 50 mL of ethanol and the resulting brown solution was kept in reflux under nitrogen for 7 days. Potassium hydroxide was added in small portions during this period and the reaction monitored by TLC (silica gel; acetonitrile:ammonium hydroxide; 9:1; v/v) until all the aminoaldehyde had been consumed. The total amount of potassium hydroxide used was 2.18 grams (0.039 mol). The solution was concentrated in vacuo and to the oily residue was added 11 mL of TFA, which produced a precipitate. The whole sample was dissolved using chloroform (100 mL) and methanol (25 mL) and washed with water (4×100 mL). Additional chloroform and methanol was used to help dissolve any precipitate that formed during the washing process. The organic layer was then washed with aqueous 0.08 M tris(hydroxymethyl)aminomethane (2×100 mL), dried over a mixture of sodium sulfate and magnesium sulfate. Upon filtration, solvent removal in a rotavap, and overnight drying under reduced pressure 4.39 grams of neutral product H4 was collected. This product contained some impurities but the sample was sufficiently pure so as to be used immediately for the next step. $^1$H NMR (600 MHz, TFA-d) δ 8.97 (s, 2H, H5), 7.94 (t, J=8.2 Hz, J'=8.0 Hz, 2H, H3), 7.81 (d, J=8.3 Hz, 2H, H4), 7.61 (d, J 7.8=Hz, 2H, H2), 4.37 (s, 6H, OCH$_3$), 3.4-3.6 (m, 8H, ring CH$_2$CH$_2$), 3.02 (br t, J=7.2 Hz, 2H, ArCH$_2$), 1.5-1.7 (m, 4H, CH$_2$CH$_2$), 1.05 (t, J=6.9 Hz, 3H, CH$_3$).

Next, 8-butyl-bis(quinoline-1,15-diol)[2,3-c:3',2'-h]-6,7, 9,10-tetrahydroacridine (H5) was prepared. Crude compound H4 (1.13 grams, 2.25 mmol) was boiled in 90 mL of 48% aqueous hydrobromic acid for 29 hours and allowed to cool to room temperature overnight. The crystallized product was collected by vacuum filtration, washed with water (2×5 mL), and dried under reduced pressure overnight to give a brown powder. $^1$H NMR (800 MHz, TFA-d) δ 9.08 (s, 2H, H5)), 8.00 (t, J=7.9 Hz, 2H, H3), 7.94 (d, J=8.2 Hz, 2H, H4), 7.86 (d, J=7.6 Hz, 2H, H2), 3.71 (m, 2H, CH$_2$), 3.67 (m, 2H, CH$_2$), 3.19 (br t, J=7.8 Hz, J'=8.3 Hz, 2H, ArCH$_2$), 1.82 (m, 2H, CH$_2$), 1.78 (m, 2H, CH$_2$), 1.20 (t, J=7.2 Hz, 3H, CH$_3$). $^{13}$C NMR (150 MHz, TFA-d) δ 156.1 (C), 148.0 (C), 147.8 (CH), 146.1 (C), 143.8 (C), 143.0 (C), 134.3 (C), 134.0 (CH), 132.6 (C), 130.4 (C), 122.2 (CH), 120.9 (CH), 32.8 (CH$_2$), 30.5 (CH$_2$), 26.9 (CH$_2$), 25.1 (CH$_2$), 24.6 (CH$_2$), 14.2 (CH$_3$).

The resulting brown powder (0.88 grams) was dissolved in 200 mL of chloroform and 15 mL of methanol and washed with 0.07 M tris(hydroxymethyl)aminomethane (2×75 mL), brine (75 mL), dried over magnesium sulfate, filtered, the solvent removed in a rotavap, and the residue dried under vacuum. This gave 0.66 grams (62%) of H5 as a brown solid sample. $^1$H NMR (250 MHz, DMSO-d$_6$) δ 11.25 (br s, OH), 8.21 (s, 2H, H5), 7.45 (d, J=7.8 Hz, 2H, H3), 7.34 (d, J=7.8 Hz, 2H, H4), 7.05 (d, J=7.5 Hz, 2H, H2), 3.16 (br s, 8H, CH$_2$CH$_2$), 2.86 (m, 2H, ArCH$_2$), 1.51 (m, 4H, CH$_2$CH$_2$), 0.98 (t, J=6.8 Hz, 3H, CH$_3$).

Crude compound H5 (0.26 grams, 0.55 mmol), cesium carbonate (0.18 grams, 0.56 mmol), and methyl chloroacetate (0.12 grams, 1.1 mmol) were stirred under nitrogen at room temperature in 25 mL of anhydrous DMF for one day. Additional drops of methyl chloroacetate were added at intervals until H5 was fully consumed as determined by TLC (silica gel, MeCN:NH$_4$OH, 9:1, v/v). The mixture was then vacuum filtered, washed with 10 mL of a hexane/chloroform solution (9:1, v/v), then with 5 mL of hexane. The filtrate was concentrated in vacuo to give a brown powder (0.25 grams, 75%). The crude can be recrystallized from methanol/ethyl acetate to afford the product L4 as light orange needles. $^1$H NMR (600 MHz, TFA-d) δ 9.04 (s, 2H, H5), 7.9-8.0 (m, 4H, H3, H4), 7.69 (d, J=7.4 Hz), 2H, H2), 5.22 (s, 4H, CH$_2$), 3.73 (s, 6H, OCH$_3$), 3.50-3.65 (m, 8H, ring CH$_2$CH$_2$), 3.07 (br t, J=7.3 Hz, J'=7.6 Hz, 2H, ArCH$_2$), 1.55-1.75 (m, 4H, CH$_2$CH$_2$), 1.07 (t, J=7.1 Hz, J'=6.8 Hz, 3H, CH$_3$). HRMS, M+Na$^+$ (abundance/ppm); calculated for [C$_{37}$H$_{35}$N$_3$NaO$_6$]$^+$: 640.2424; measured: 640.2417 (1.1).

Example 10

Representative complexes of 8,8'-dimethoxy-3,3'-dimethylene-2,2'-biquinoline (D1) were made in solution to obtain NMR spectra.

The following $^1$H NMR spectra were obtained by preparing complexes in situ as follows: 100 µL of the corresponding metal salt in D$_2$O was added to a solution of D1 in CD$_3$CN (0.5 mL), and then mixed to obtain one phase. Final concentrations: [D1]=0.005 M; [M+]=0.05 M (perchlorate salts). Each spectrum was referenced to the middle peak of residual CH$_3$CN (1.94 ppm).

D1+NaClO$_4$. $^1$H NMR (800 MHz, CD$_3$CN/D$_2$O, 0.5:0.01 v/v) δ 3.27 (s, 4H, CH$_2$), 4.07 (s, 6H, OCH$_3$), 7.20 (d, 2H, H2), 7.55 (d, 2H, H4), 7.51 (t, 2H, H3), 8.24 (s, 2H, H5).

Figure 9:
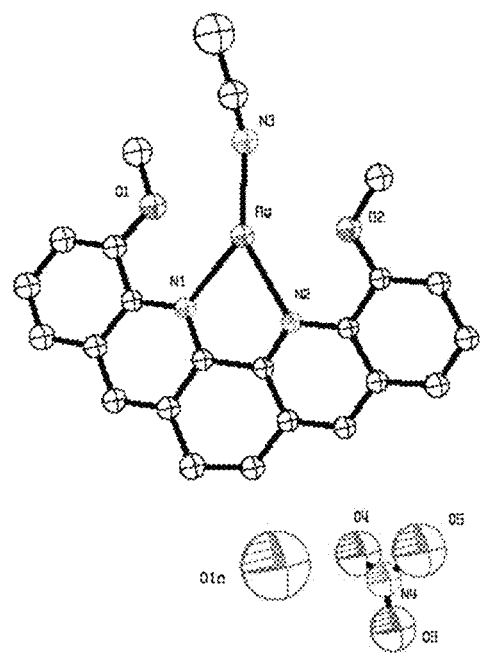
FIG. 9 shows the X-ray crystal structure of the complex $D1.AgClO_4.CH_3CN$. This is a 1:1 complex (ligand:metal).

D1+AgClO$_4$. $^1$H NMR (800 MHz, CD$_3$CN/D$_2$O, 0.5:0.01 v/v) δ 3.22 (s, 4H, CH$_2$), 4.11 (s, 6H, OCH$_3$), 7.24 (d, 2H, H2), 7.49 (d, 2H, H4), 7.58 (t, 2H, H3), 8.26 (s, 2H, H5). This complex is shown in FIG. 9.

Figure 10:
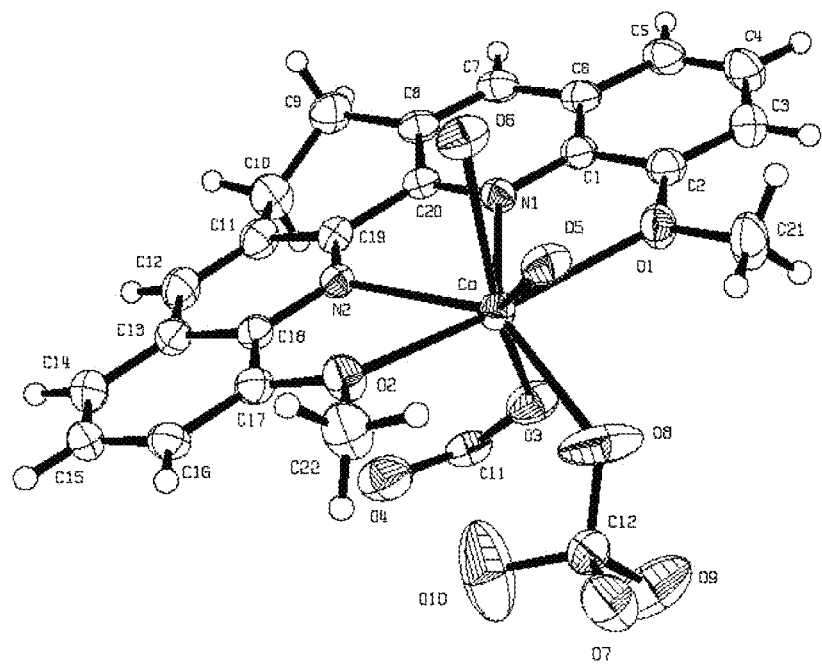
FIG. 10 shows the X-ray crystal structure of the complex $D1.Ca(ClO_4)_2$. This is a 1:1 complex (ligand:metal). Portions of additional perchlorate ions belonging to a nearby complex (not shown) also appear.

D1+Ca(ClO$_4$)$_2$. $^1$H NMR (800 MHz, CD$_3$CN/D$_2$O, 0.5:0.01 v/v) δ 3.34 (s, 4H, CH$_2$), 4.26 (s, 6H, OCH$_3$), 7.39 (d, 2H, H2), 7.64 (d, 2H, H4), 7.66 (t, 2H, H3), 8.41 (s, 2H, H5). This complex is shown in FIG. 10.

Figures 11, 12:
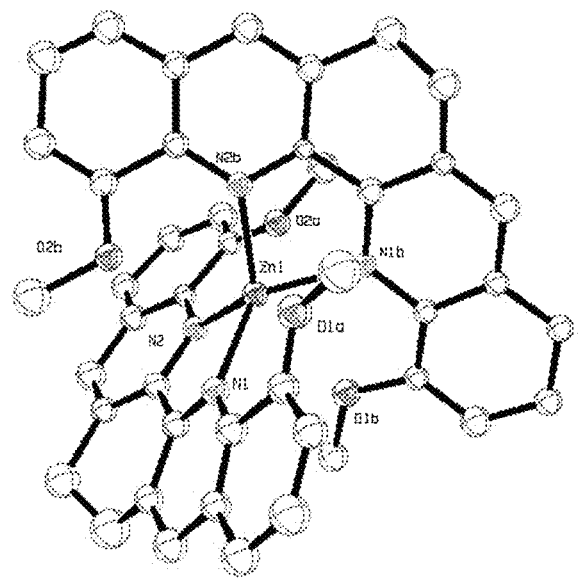
FIG. 11 shows the X-ray crystal structure of the complex $(D1)_2.Zn(ClO_4)_2$. This is a 2:1 (ligand:metal) encapsulating complex. The perchlorate ions have been omitted.
FIG. 12 shows the X-ray crystal structure of the complex $(D1)_2.Cd(ClO_4)_2$. This is a 2:1 (ligand:metal) encapsulating complex. The perchlorate ions are not shown.

D1+Zn(ClO$_4$)$_2$. The following is the data for the 1:1 complex. $^1$H NMR (800 MHz, CD$_3$CN/D$_2$O, 0.5:0.01 v/v) δ 3.43 (s, 4H, CH$_2$), 4.20 (s, 6H, OCH$_3$), 7.41 (d, 2H, H2), 7.68 (d, 2H, H4), 7.74 (t, 2H, H3), 8.63 (s, 2H, H5). The 2:1 (D$_1$:Zn$^{2+}$) complex is also present in the solution, albeit in trace amount, and gives this data: δ 2.97 (s, 6H, OCH$_3$), 3.63 (s, 4H, CH$_2$), 6.96 (d, 2H, H2), 7.57 (t, 2H, H3), 7.70 (d, 2H, H4), 8.84 (s, 2H, H5). The 2:1 encapsulating complex is shown in FIG. 11.

D1+Al(ClO$_4$)$_3$. $^1$H NMR (800 MHz, CD$_3$CN/D$_2$O, 0.5:0.01 v/v) δ 3.39 (s, 4H, CH$_2$), 4.19 (s, 6H, OCH$_3$), 7.41 (d, 2H, H2), 7.62 (d, 2H, H4), 7.73 (t, 2H, H3), 8.64 (s, 2H, H5). Crystals obtained from this sample unexpectedly afforded the protonated compound shown in FIG. 15.

D1+La(ClO$_4$)$_3$. $^1$H NMR (800 MHz, CD$_3$CN/D$_2$O, 0.5:0.01 v/v) δ 3.27 (br s, 4H, CH$_2$), 4.11 (br s, 6H, OCH$_3$), 7.25 (br s, 2H, H2), 7.53 (br s, 2H), 7.63 (br s, 2H), 8.33 (br s, 2H, H5).

(b) The following is the $^1$H NMR spectra obtained after dissolving crystals of the complex in the indicated NMR solvent. The barium complex was too insoluble for analysis. Nickel and copper complexes gave several complexes in solution (with broad signals), which complicated NMR analysis.

D1+KO—CO—CH$_3$. $^1$H NMR (600 MHz, CD$_3$CN) δ 3.12 (s, 4H, CH$_2$), 3.87 (br s, 6H, OCH$_3$), 7.00 (d, 2H, H2), 7.42 (d, 2H, H4), 7.49 (t, 2H, H3), 8.10 (s, 2H, H5). D1+KSCN $^1$H NMR (400 MHz, CD$_3$CN) δ 8.22, 7.57 (m,

2H, H3), 7.51 (dd, J=1.2 Hz, J'=8.4 Hz, 2H, H4), 7.22 (dd, J=1.2 Hz, J'=7.7 Hz, 2H, H2), 4.14 (s, 6H, 2xOCH$_3$), 3.23 (s, 4H, 2xCH$_2$).

D1+Mg(ClO$_4$)$_2$. $^1$H NMR (600 MHz, CD$_3$CN) δ 3.27 (s, 4H, CH$_2$), 4.24 (s, 6H, OCH$_3$), 7.35 (br d, 2H, H2), 7.61 (br d, 2H, H4), 7.68 (br t, 2H, H3), 8.41 (br s, 2H, H5).

D1+Cd(ClO$_4$)$_2$. This is a 2:1 encapsulating complex. $^1$H NMR (600 MHz, CD$_3$CN) δ 2.97 (s, 6H, OCH$_3$), 3.61 (s, 4H, CH$_2$), 7.04 (d, 2H, H2), 7.61 (t, 2H, H4), 7.72 (d, 2H, H3), 8.79 (s, 2H, H5). This complex is shown in FIG. 12.

Figure 13:
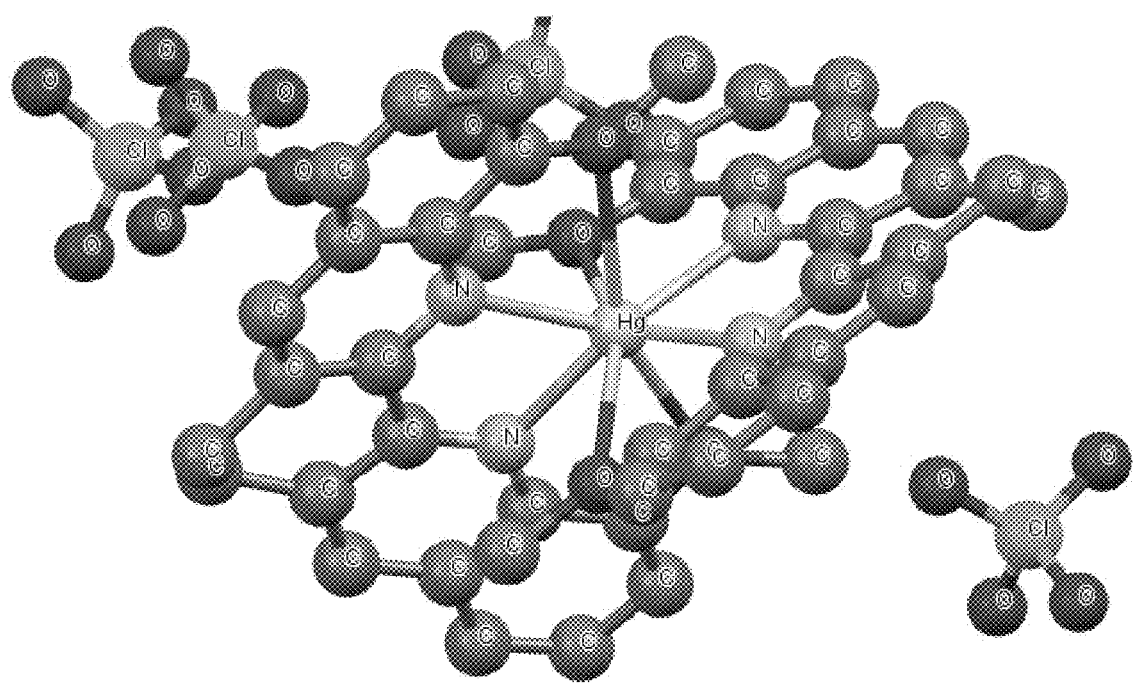
FIG. 13 shows the X-ray crystal structure of the complex $(D1)_2.Hg(ClO_4)_2$. This is a 2:1 (ligand:metal) encapsulating complex. Additional perchlorate ions belonging to a nearby complex (not shown) also appear.

D1+Hg(ClO$_4$)$_2$. This is a 2:1 encapsulating complex. $^1$H NMR (600 MHz, CD$_3$CN) δ 2.92 (s, 6H, OCH$_3$), 3.60 (s, 4H, CH$_2$), 7.01 (d, 2H, H2), 7.64 (t, 2H, H4), 7.72 (d, 2H, H3), 8.81 (s, 2H, H5). This complex is shown in FIG. 13.

D1+AgClO$_4$. $^1$H NMR (800 MHz, CD$_3$CN) δ 3.30 (s, 4H, CH$_2$), 3.98 (s, 6H, OCH$_3$), 7.22 (br d, 2H, H2), 7.54 (d, 2H, H4), 7.61 (t, 2H, H3), 8.26 (s, 2H, H5).

Figure 14:
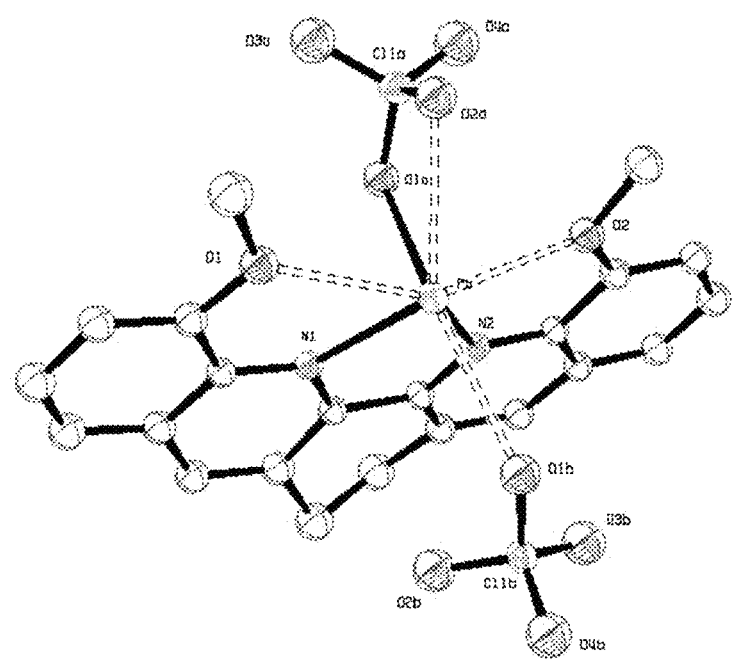
FIG. 14 shows the X-ray crystal structure of the complex $D1.Pb(ClO_4)_2$. This is a 1:1 complex (ligand:metal).

D1+Pb(ClO$_4$)$_2$. $^1$H NMR (600 MHz, CD$_3$CN) δ 3.44 (s, 4H, CH$_2$), 4.38 (s, 6H, OCH$_3$), 7.50 (d, 2H, H2), 7.74 (d, 2H, H4), 7.80 (t, 2H, H3), 8.69 (s, 2H, H5). This complex is shown in FIG. 14.

D1+L$^a$(ClO$_4$)$_3$. $^1$H NMR (600 MHz, CD$_3$CN) δ 3.45 (s, 4H, CH$_2$), 4.24 (s, 6H, OCH$_3$), 7.43 (d, 2H, H2), 7.64 (d, 2H, H4), 7.77 (t, 2H, H3), 8.67 (s, 2H, H5).

D1+Eu(ClO$_4$)$_2$. $^1$H NMR (600 MHz, CD$_3$CN) δ 3.45 (s, 4H, CH$_2$), 4.24 (s, 6H, OCH$_3$), 7.44 (d, 2H, H2), 7.66 (d, 2H, H4), 7.79 (t, 2H, H3), 8.68 (s, 2H, H5).

D1+Gd(ClO$_4$)$_3$. $^1$H NMR (600 MHz, CD$_3$CN) δ 3.41 (br s, 4H, CH$_2$), 4.20 (br s, 6H, OCH$_3$), 7.39 (br s, 2H, H2), 7.60 (br s, 2H), 7.72 (br s, 2H), 8.57 (br s, 2H, H5).

Figure 15:
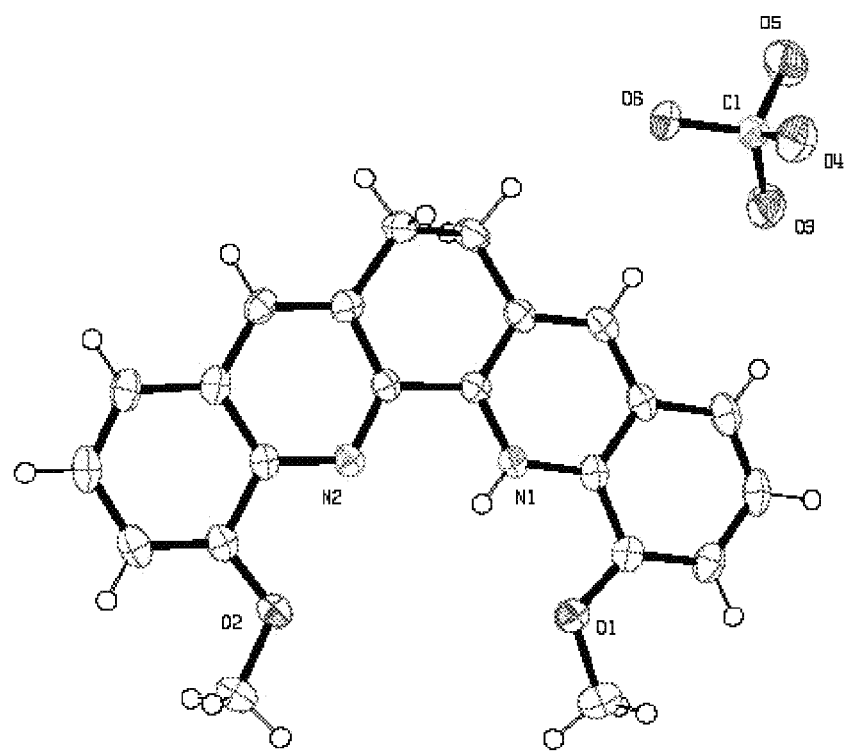
FIG. 15 shows the X-ray crystal structure of the complex $D1.HClO_4$. The D1 compound is monoprotonated.
Figure 16:
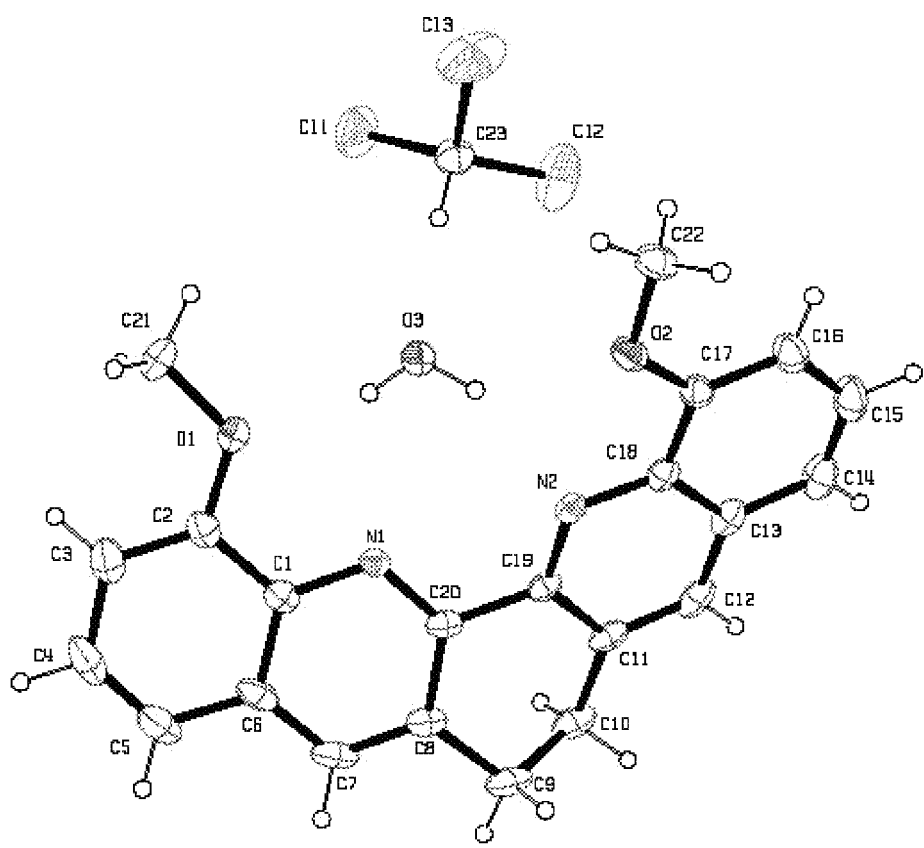
FIG. 16 shows the X-ray crystal structure of the free D1 compound with water and chloroform solvent molecules.
Figure 17:
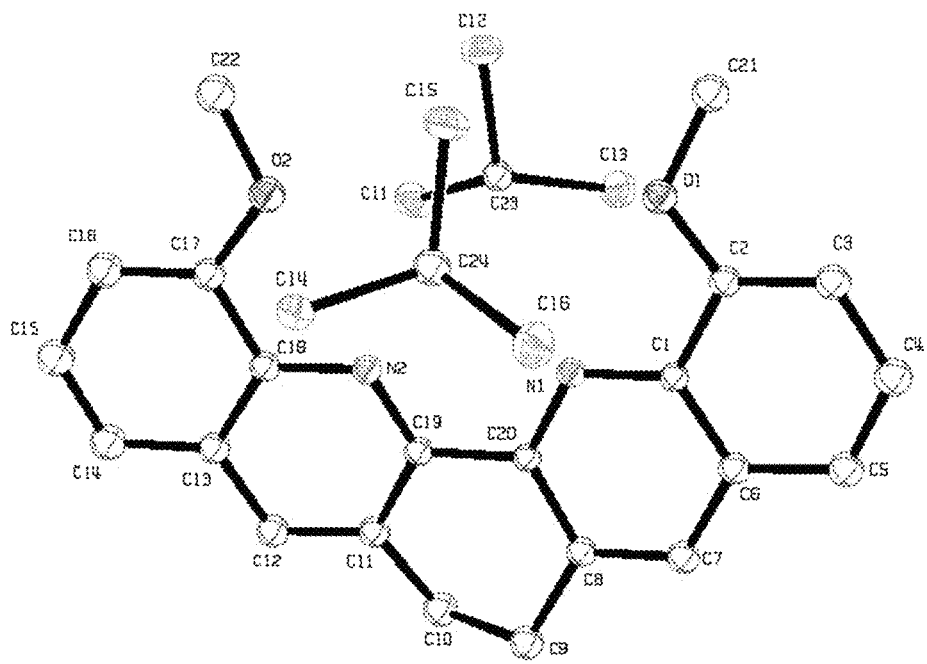
FIG. 17 shows the X-ray crystal structure of the free D1 compound with chloroform solvent molecules.

FIG. 15 is an illustration of the crystal structure of the complex D1.HClO$_4$, and as noted above was unexpectedly crystallized from aluminum perchlorate.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A compound having the structure of Formula (S2):

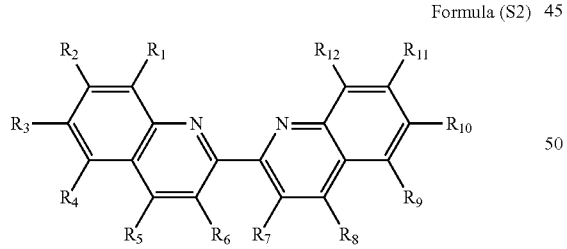

Formula (S2)

wherein R$_1$, R$_2$, R$_3$, R$_4$, R$_5$, R$_6$, R$_7$, R$_8$, R$_9$, R$_{10}$, R$_{11}$, and R$_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; and wherein alternatively R$_6$ and R$_7$ are joined together to form a cyclic ring and together comprise an alkyl or substituted alkyl linkage;

with the proviso that at least one of R$_1$ to R$_6$ is —OR', —SR', —COR', or —NR'$_2$;

and the proviso that at least one of R$_7$ to R$_{12}$ is —OR", —SR", —COR", or —NR"$_2$;

wherein R' and R" either (a) are independently heteroaryl, substituted heteroaryl, heterocyclic, substituted heterocyclic, alkenyl, substituted alkenyl, alkynyl, substituted alkynyl, carboxy, phosphate, a boron-containing group, or a chelating ligand selected from —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, or salts thereof, wherein m and n are independently integers from 0 to 10 and m+n≥1; R is hydroxyl, amino, alkyl, substituted alkyl, aryl, substituted aryl, heteroaryl, substituted heteroaryl, heterocyclic, or substituted heterocyclic, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic, and Z is sulfur or oxygen, or (b) together form a linking moiety, so that the compound is a macrocyclic compound.

2. The compound of claim 1, wherein only one of R$_1$ to R$_5$ is —OR', —SR', —COR', or —NR'$_2$; and only one of R$_8$ to R$_{12}$ is —OR", —SR", —COR", or —NR"$_2$.

3. The compound of claim 1, wherein R$_4$ and R$_9$ are the same, and are not hydrogen or a water-solubilizing group.

4. The compound of claim 1, wherein R' and R" are the same.

5. The compound of claim 1, wherein R$_6$ and R$_7$ are joined together to form a cyclic ring and together comprise an alkyl or substituted alkyl linkage, and wherein R' and R" include an O$^-$ charge; a carboxy group; an amide group; a phosphate (PO$_4$) group; an imide group; a nitrate group; a pyridinone or piperidinone group; or an oxazole group.

6. A compound having the structure of Formula (S2):

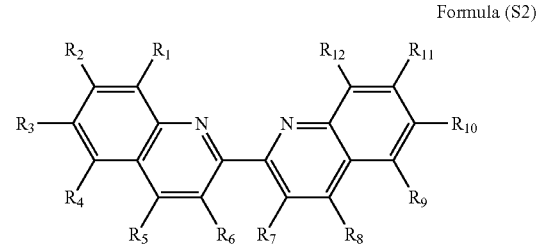

Formula (S2)

wherein R$_1$, R$_2$, R$_3$, R$_4$, R$_5$, R$_6$, R$_7$, R$_8$, R$_9$, R$_{10}$, R$_{11}$, and R$_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; and wherein alternatively R$_6$ and R$_7$ are joined together to form a cyclic ring and together comprise an alkyl or substituted alkyl linkage;

with the proviso that one of R$_1$ to R$_6$ is —OR', —SR', —COR', or —NR'$_2$;

and the proviso that one of R$_7$ to R$_{12}$ is —OR", —SR", —COR", or —NR"$_2$;

wherein R' and R" together form a linking moiety, so that the compound is a macrocyclic compound.

7. A composition comprising a compound having the structure of Formula (S2), wherein the compound is immobilized on a polymer surface or embedded into a polymer matrix:

Formula (S2)

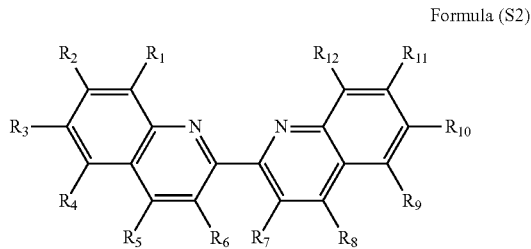

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; and wherein alternatively $R_6$ and $R_7$ are joined together to form a cyclic ring and together comprise an alkyl or substituted alkyl linkage;

with the proviso that at least one of $R_1$ to $R_6$ is —OR', —SR', —COR', or —NR'$_2$;

and the proviso that at least one of $R_7$ to $R_{12}$ is —OR", —SR", —COR", or —NR"$_2$;

wherein R' and R" either (a) are independently heteroaryl, substituted heteroaryl, heterocyclic, substituted heterocyclic, alkenyl, substituted alkenyl, alkynyl, substituted alkynyl, carboxy, phosphate, a boron-containing group, or a chelating ligand selected from —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, or salts thereof, wherein m and n are independently integers from 0 to 10 and m+n≥1; R is hydroxyl, amino, alkyl, substituted alkyl, aryl, substituted aryl, heteroaryl, substituted heteroaryl, heterocyclic, or substituted heterocyclic, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic, and Z is sulfur or oxygen, or (b) together form a linking moiety, so that the monomer is a macrocyclic monomer.

8. A complex comprising a compound of Formula (S2) bound to any metal ion or protonated:

Formula (S2)

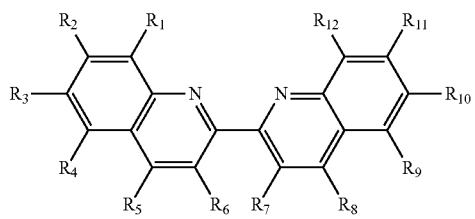

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; and wherein alternatively $R_6$ and $R_7$ are joined together to form a cyclic ring and together comprise an alkyl or substituted alkyl linkage;

with the proviso that at least one of $R_1$ to $R_6$ is —OR', —SR', —COR', or —NR'$_2$;

and the proviso that at least one of $R_7$ to $R_{12}$ is —OR", —SR", —COR", or —NR"$_2$;

wherein R' and R" either (a) are independently substituted heteroaryl, heterocyclic, substituted heterocyclic, alkenyl, substituted alkenyl, alkynyl, substituted alkynyl, carboxy, phosphate, a boron-containing group, or a chelating ligand selected from —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, or salts thereof, wherein m and n are independently integers from 0 to 10 and m+n≥1; R is hydroxyl, amino, alkyl, substituted alkyl, aryl, substituted aryl, heteroaryl, substituted heteroaryl, heterocyclic, or substituted heterocyclic, R$^1$, R$^2$, and R$^3$ are independently hydrogen, hydroxyl, amino, alkyl, substituted alkyl, aryl, substituted aryl, heteroaryl, substituted heteroaryl, heterocyclic, or substituted heterocyclic, and Z is sulfur or oxygen, or (b) together form a linking moiety, so that the compound is a macrocyclic compound.

9. The complex of claim 8, wherein the metal ion is Gd(III), Fe(III), Co(III), Ni(II), Mn(II), Cu(II), Mg(II), Sr(II), Ca(II), Cd(II), Zn(II), Ba(II), K$^+$, Al(III), Pb(II), La(III), Co(II), Hg(II), Eu$^{3+}$, or a paramagnetic metal ion.

10. The complex of claim 8, wherein only one of $R_1$ to $R_5$ is —OR', —SR', —COR', or —NR'$_2$; and only one of $R_8$ to $R_{12}$ is —OR", —SR", —COR", or —NR"$_2$.

11. The complex of claim 8, wherein $R_4$ and $R_9$ are the same, and are not hydrogen or alkoxy.

12. The complex of claim 8, wherein $R_4$ and $R_9$ are the same, and are not hydrogen or a water-solubilizing group.

13. The complex of claim 8, wherein R' and R" are the same.

14. The complex of claim 8, wherein $R_6$ and $R_7$ are joined together to form a cyclic ring and together comprise an alkyl or substituted alkyl linkage, and wherein R' and R" include an O$^-$ charge; a carboxy group; an amide group; a phosphate (PO$_4$) group; an imide group; a nitrate group; a pyridinone or piperidinone group; or an oxazole group.

15. A complex comprising a compound of Formula (B1) or (B2) bound to any metal ion or protonated:

(B1)

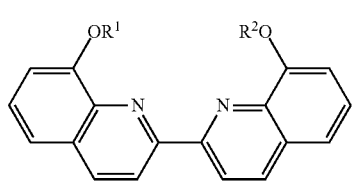

(B2)

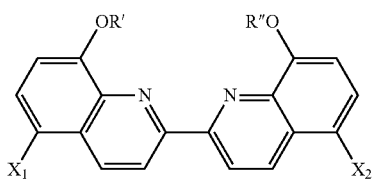

wherein $R^1$ and $R^2$ are independently alkyl or substituted alkyl; R' and R" are independently alkyl, substituted alkyl, aryl, substituted aryl, heteroaryl, substituted heteroaryl, heterocyclic, substituted heterocyclic, alkenyl, substituted alkenyl, alkynyl, substituted alkynyl, aldehyde, carboxy, phosphate, a boron-containing group, or a chelating ligand comprising at least one linking group and at least one heteroatom; and $X_1$ and $X_2$ are independently halogen.

16. A method for forming a metal complex, comprising: contacting a metal ion with a compound having the structure of Formula (S2):

Formula (S2)

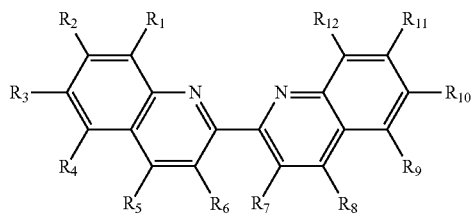

wherein $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, alkoxy, substituted alkoxy, halogen, alkyl, substituted alkyl, aryl, substituted aryl, heteroaryl, substituted heteroaryl, heterocyclic, substituted heterocyclic, alkenyl, substituted alkenyl, alkynyl, substituted alkynyl, hydroxyl, aldehyde, carboxy, ester, sulfonate, sulfonamide, carboxamide, amino, nitro, nitroso, nitrile, azo, phosphate, a boron-containing group, thiol, sulfide, and a water-solubilizing group; and wherein alternatively $R_6$ and $R_7$ are joined together to form a cyclic ring and together comprise an alkyl or substituted alkyl linkage; with the proviso that at least one of $R_1$ to $R_6$ is —OR', —SR', —COR', or —NR'$_2$;

and the proviso that at least one of $R_7$ to $R_{12}$ is —OR", —SR", —COR", or —NR"$_2$;

wherein R' and R" either (a) are independently substituted heteroaryl, heterocyclic, substituted heterocyclic, alkenyl, substituted alkenyl, alkynyl, substituted alkynyl, carboxy, phosphate, a boron-containing group, or a chelating ligand selected from —(CH$_2$)$_n$—CO—OR, —(CH$_2$)$_n$—CO—NR$^1$R$^2$, —(CH$_2$)$_n$—Z—(CH$_2$)$_m$—CO—OR, —(CH$_2$)$_n$—NR$^3$—(CH$_2$)$_m$—CO—OR, or salts thereof, wherein m and n are independently integers from 0 to 10 and m+n≥1; R is hydroxyl, amino, alkyl, substituted alkyl, aryl, substituted aryl, heteroaryl, substituted heteroaryl, heterocyclic, or substituted heterocyclic, $R^1$, $R^2$, and $R^3$ are independently hydrogen, hydroxyl, amino, alkyl, substituted alkyl, aryl, substituted aryl, heteroaryl, substituted heteroaryl, heterocyclic, or substituted heterocyclic, and Z is sulfur or oxygen, or (b) together form a linking moiety, so that the compound is a macrocyclic compound;

wherein the compound forms the metal complex upon binding to the metal ion.

17. The method of claim 16, wherein the compound is contacted with the metal ion in a solution or slurry or as a solid, and further comprising monitoring the solution or slurry or solid to detect a change in the color of light emitted by the compound, such a change indicating that binding has occurred.

18. The method of claim 17, further comprising extracting the metal ion from the solution or slurry or solid.

* * * * *